(12) United States Patent
Sadarangani et al.

(10) Patent No.: US 11,740,702 B2
(45) Date of Patent: Aug. 29, 2023

(54) APPARATUS AND METHODS FOR DETECTING, QUANTIFYING, AND PROVIDING FEEDBACK ON USER GESTURES

(71) Applicant: BIOINTERACTIVE TECHNOLOGIES, INC., Vancouver (CA)

(72) Inventors: Gautam Sadarangani, Burnaby (CA); Zhen Xiao, Surrey (CA); Sohail Sangha, New Westminster (CA); Allan Fernandes, Surrey (CA); Yin He, New Westminster (CA); David Silvester, Vancouver (CA)

(73) Assignee: BIOINTERACTIVE TECHNOLOGIES, INC., Vancouver (CA)

( * ) Notice: Subject to any disclaimer, the term of this patent is extended or adjusted under 35 U.S.C. 154(b) by 0 days.

(21) Appl. No.: 16/763,769

(22) PCT Filed: Nov. 13, 2018

(86) PCT No.: PCT/CA2018/051435
§ 371 (c)(1),
(2) Date: May 13, 2020

(87) PCT Pub. No.: WO2019/095050
PCT Pub. Date: May 23, 2019

(65) Prior Publication Data
US 2020/0371598 A1    Nov. 26, 2020

Related U.S. Application Data

(60) Provisional application No. 62/607,223, filed on Dec. 18, 2017, provisional application No. 62/585,709, filed on Nov. 14, 2017.

(51) Int. Cl.
*G06F 3/01* (2006.01)
*A61B 5/0295* (2006.01)
(Continued)

(52) U.S. Cl.
CPC ............ *G06F 3/017* (2013.01); *A61B 5/0295* (2013.01); *A61B 5/1125* (2013.01); *A61B 5/225* (2013.01);
(Continued)

(58) Field of Classification Search
CPC .......... G06F 3/017; G06F 1/163; G06F 3/016; G06F 3/0346; A61B 5/0295; A61B 5/1125; A61B 5/225; A61B 5/4528; A61B 5/681
See application file for complete search history.

(56) References Cited

U.S. PATENT DOCUMENTS

| | | | |
|---|---|---|---|
| 5,930,741 A * | 7/1999 | Kramer | .................. G06F 3/011 340/573.7 |
| 9,575,560 B2 * | 2/2017 | Poupyrev | ................ G01S 13/89 |

(Continued)

FOREIGN PATENT DOCUMENTS

| | | |
|---|---|---|
| CN | 101410098 A | 4/2009 |
| WO | WO-2017050784 A1 | 3/2017 |
| WO | WO-2019095050 A1 | 5/2019 |

OTHER PUBLICATIONS

European Patent Application No. 18879879.7 European Search Report dated Jul. 15, 2021.
(Continued)

*Primary Examiner* — Grant Sitta
(74) *Attorney, Agent, or Firm* — Wilson Sonsini Goodrich & Rosati

(57) ABSTRACT

Methods and apparatus related to wearable devices (150) worn at a location on a user's body, which in response to execution of processor-executable instructions (120) detect for the user pose or motion and pose at location proximate to or more distally disposed to the wearable device (150). The apparatus (100) includes a wearable user interface device. The wearable device (150) via an associated pro-
(Continued)

cessor (104) detects, at least, volume changes in a user's limb. The wearable device (150) generates gesture information from, at least one of, myographic force data, proximity data, and inertial measurement data. The wearable device (150) may be included in a larger apparatus (100). The wearable device (150) or larger apparatus (100) may include methods of operation in which at least one processor (105) generates gesture and/or extremity information and takes at least one tangible action based on the information.

51 Claims, 29 Drawing Sheets

(51) Int. Cl.
  A61B 5/11 (2006.01)
  G06F 3/0346 (2013.01)
  A61B 5/22 (2006.01)
  A61B 5/00 (2006.01)
  G06F 1/16 (2006.01)
(52) U.S. Cl.
  CPC ............ *A61B 5/4528* (2013.01); *A61B 5/681* (2013.01); *G06F 1/163* (2013.01); *G06F 3/016* (2013.01); *G06F 3/0346* (2013.01)

(56) References Cited

U.S. PATENT DOCUMENTS

| 2012/0087216 | A1 | 4/2012 | Keung et al. | |
|---|---|---|---|---|
| 2014/0240103 | A1 | 8/2014 | Lake et al. | |
| 2014/0368474 | A1* | 12/2014 | Kim | A61B 5/681 |
| | | | | 345/179 |
| 2015/0301606 | A1* | 10/2015 | Andrei | G06F 3/011 |
| | | | | 345/156 |
| 2015/0378433 | A1* | 12/2015 | Savastinuk | G06F 3/011 |
| | | | | 345/156 |
| 2016/0202759 | A1* | 7/2016 | Choi | A61B 5/221 |
| | | | | 345/156 |
| 2016/0252607 | A1* | 9/2016 | Saboo | G01S 7/415 |
| | | | | 342/107 |
| 2016/0292497 | A1* | 10/2016 | Kehtarnavaz | G06K 9/00355 |
| 2017/0046931 | A1* | 2/2017 | Hartweg | A47F 7/024 |
| 2017/0165481 | A1 | 6/2017 | Menon | |
| 2017/0259428 | A1* | 9/2017 | Assad | G16H 40/67 |
| 2017/0285744 | A1* | 10/2017 | Juliato | G06F 3/014 |
| 2017/0285756 | A1* | 10/2017 | Wang | G06F 3/0346 |
| 2017/0332946 | A1* | 11/2017 | Kikkeri | A61B 5/1127 |
| 2018/0143686 | A1* | 5/2018 | An | G06F 3/015 |
| 2018/0157330 | A1* | 6/2018 | Gu | G06F 3/017 |
| 2018/0329050 | A1* | 11/2018 | Amihood | G01S 13/04 |
| 2018/0348339 | A1* | 12/2018 | Lien | G01S 7/023 |
| 2018/0348353 | A1* | 12/2018 | Lien | H01Q 3/40 |
| 2020/0204541 | A1* | 6/2020 | Nair | G01S 13/34 |
| 2020/0393890 | A1* | 12/2020 | Hayashi | G06F 1/3265 |

OTHER PUBLICATIONS

PCT/CA2018/051435 International Search Report and Written Opinion dated Feb. 7, 2019.

Xiao, Z. Detecting upper extremity activity with force myography. [Thesis] Simon Fraser University; retrieved from https://summit.sfu.ca/item/17686 (2017).

\* cited by examiner

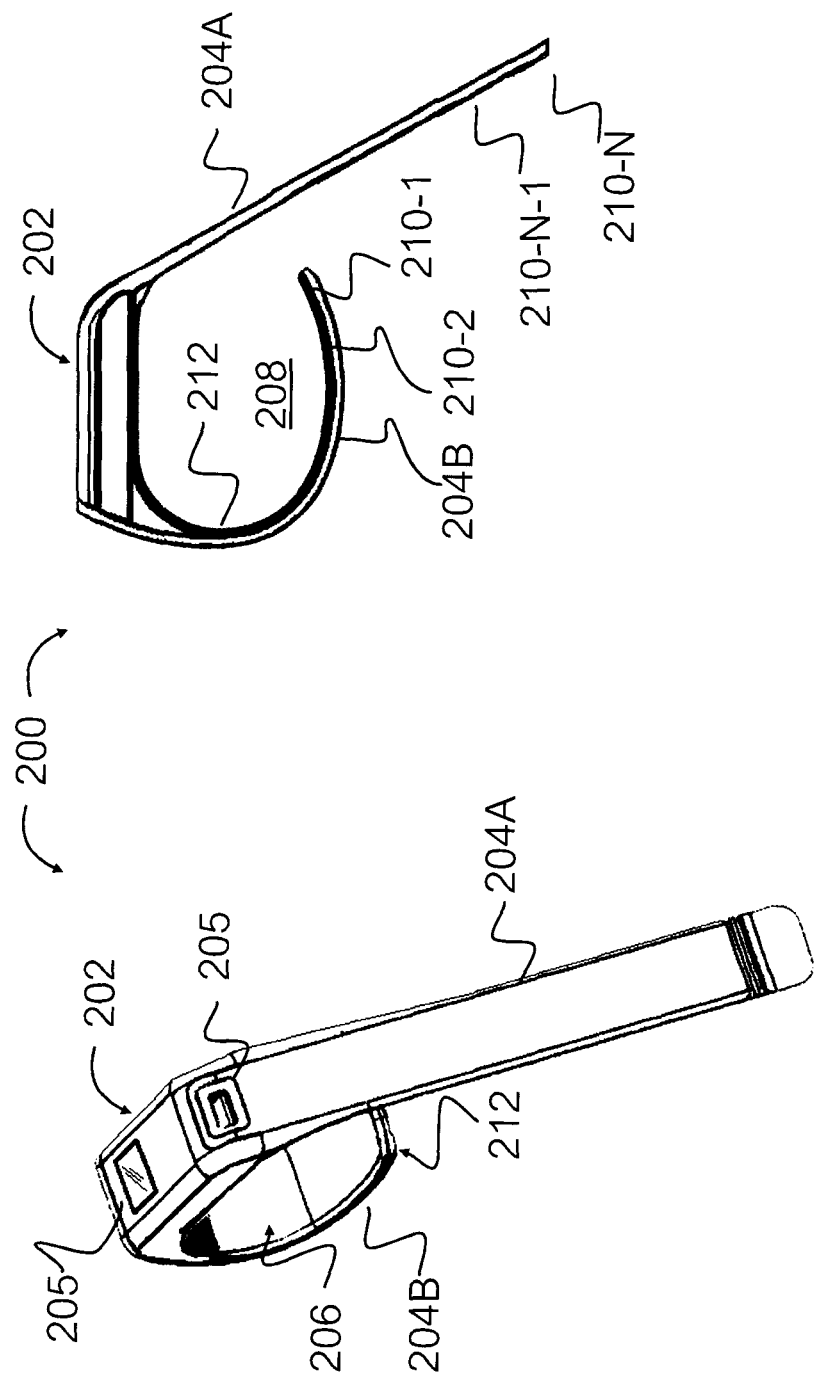

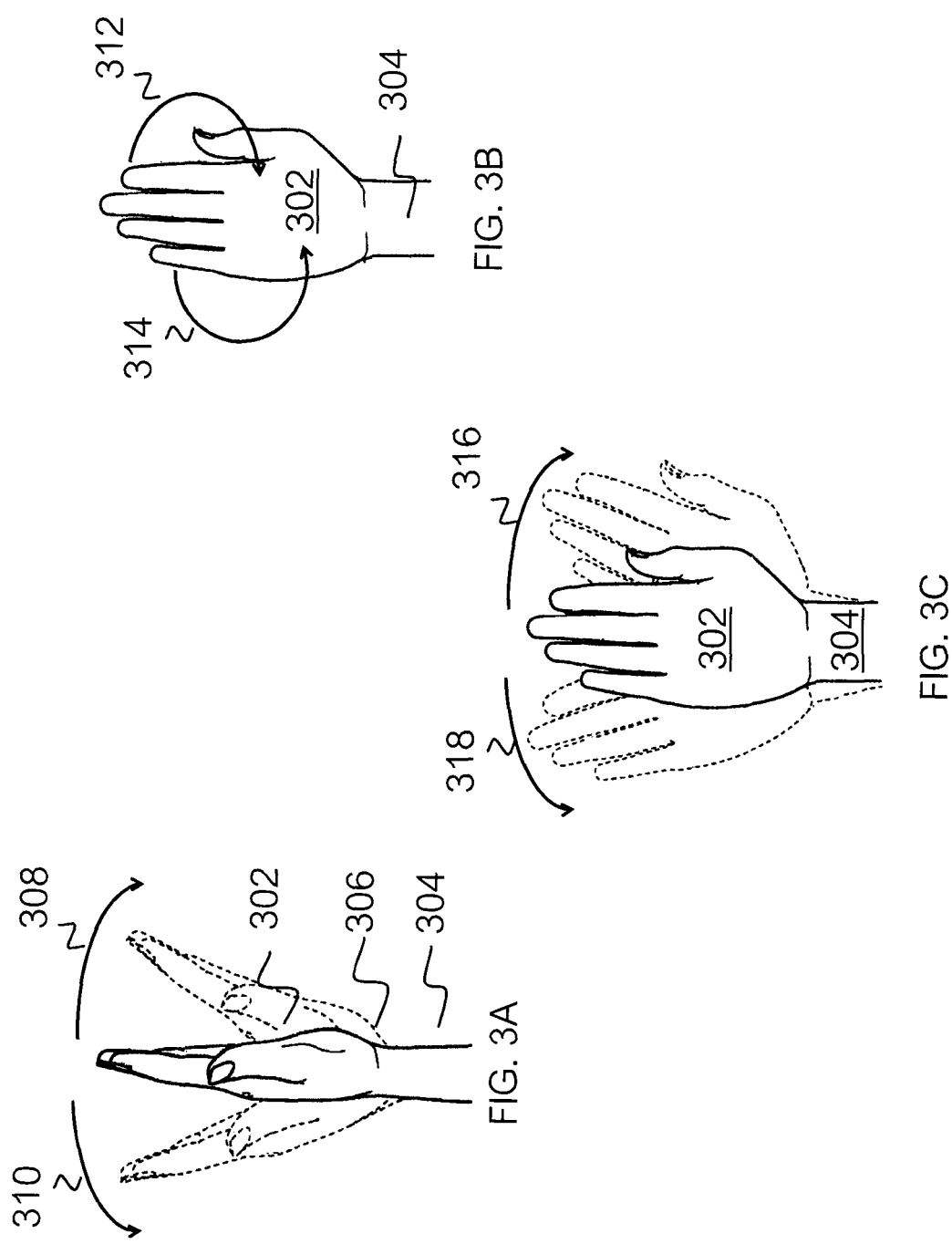

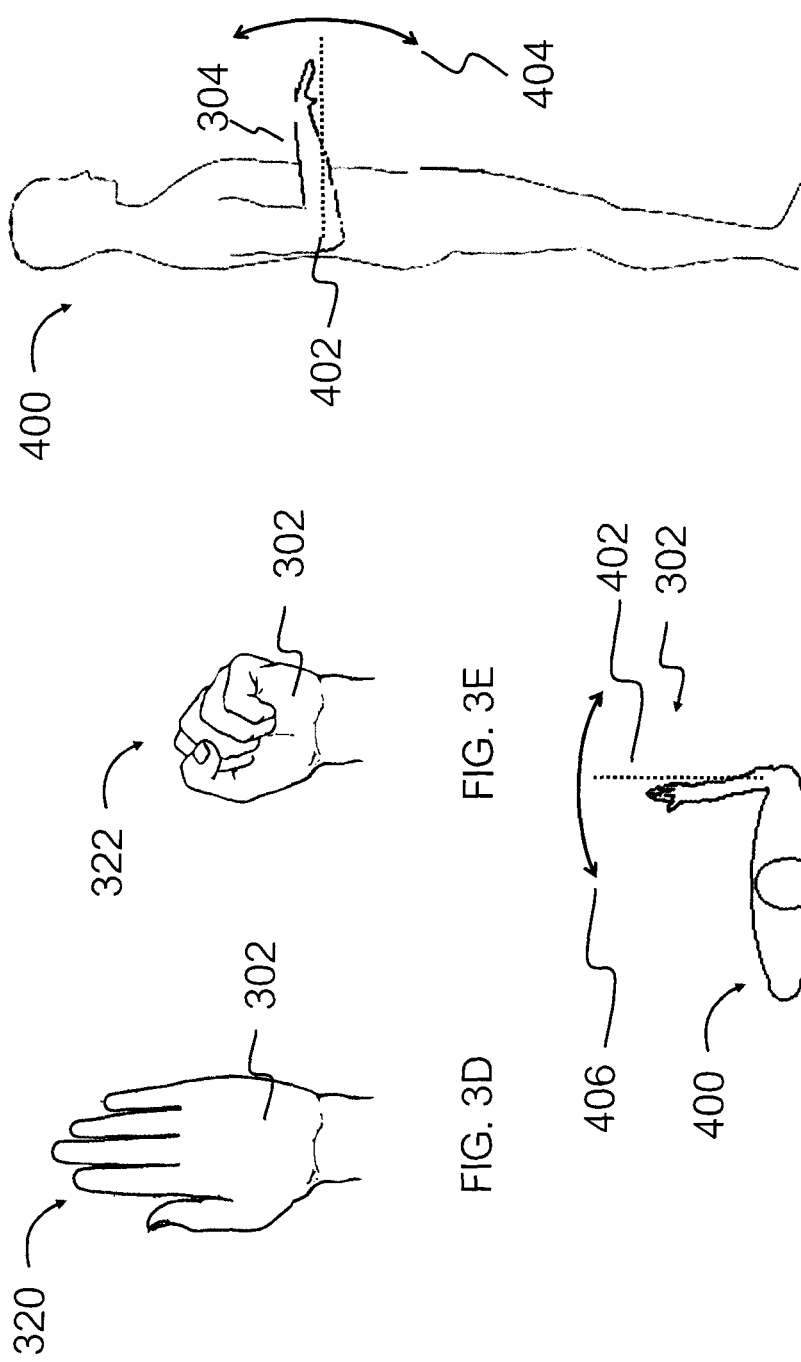

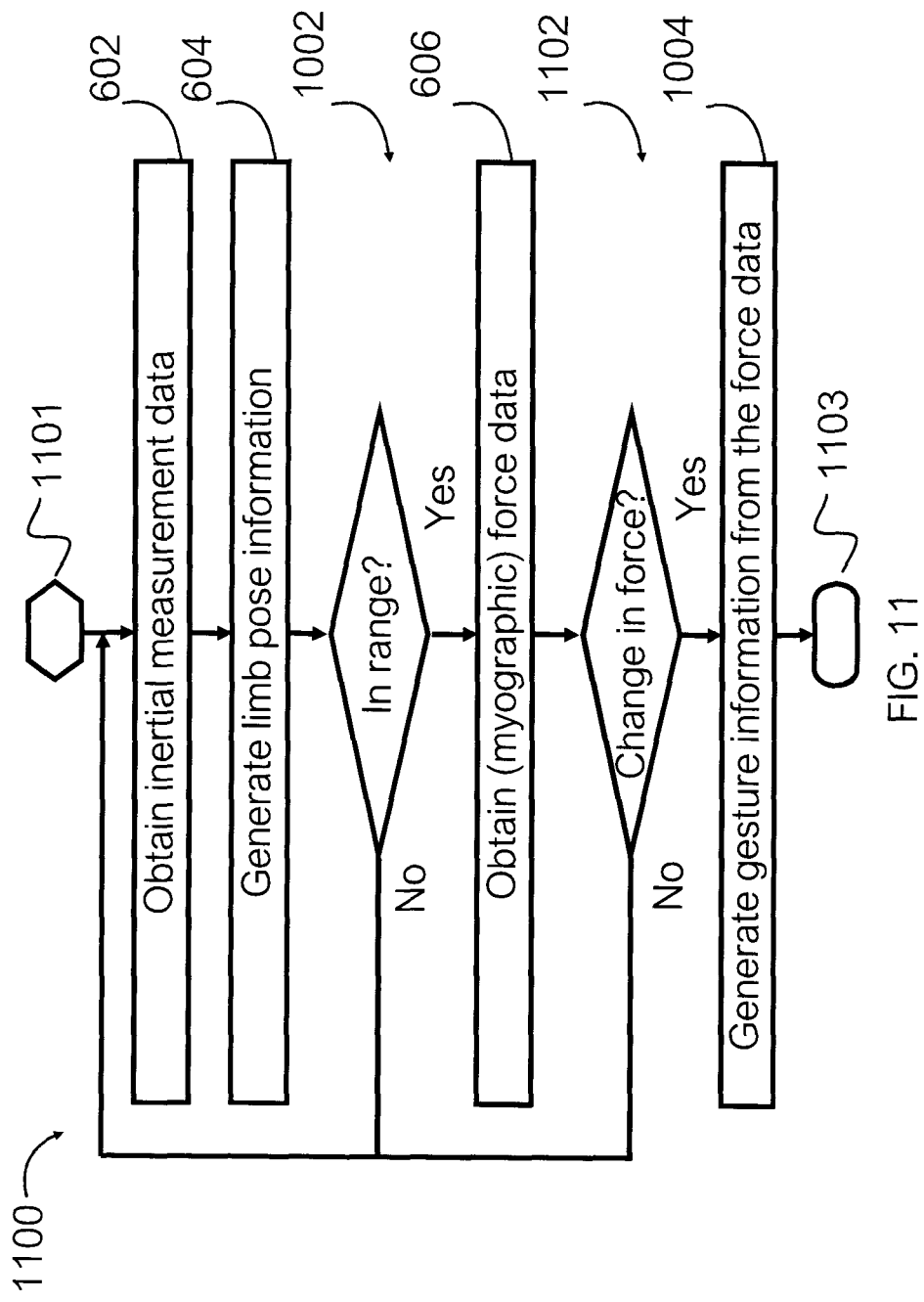

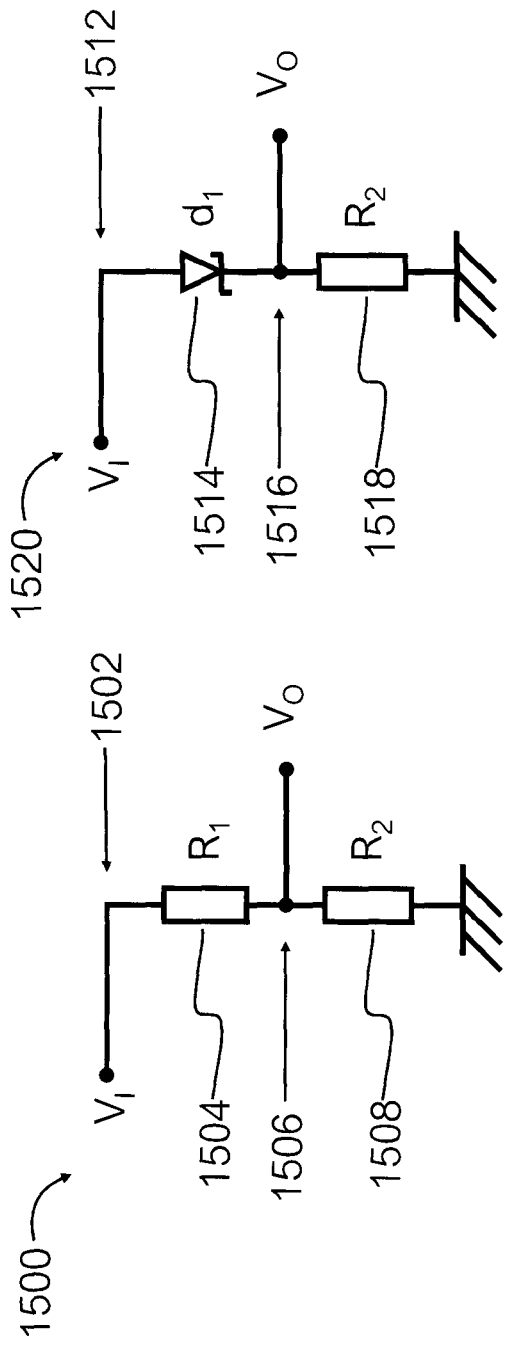
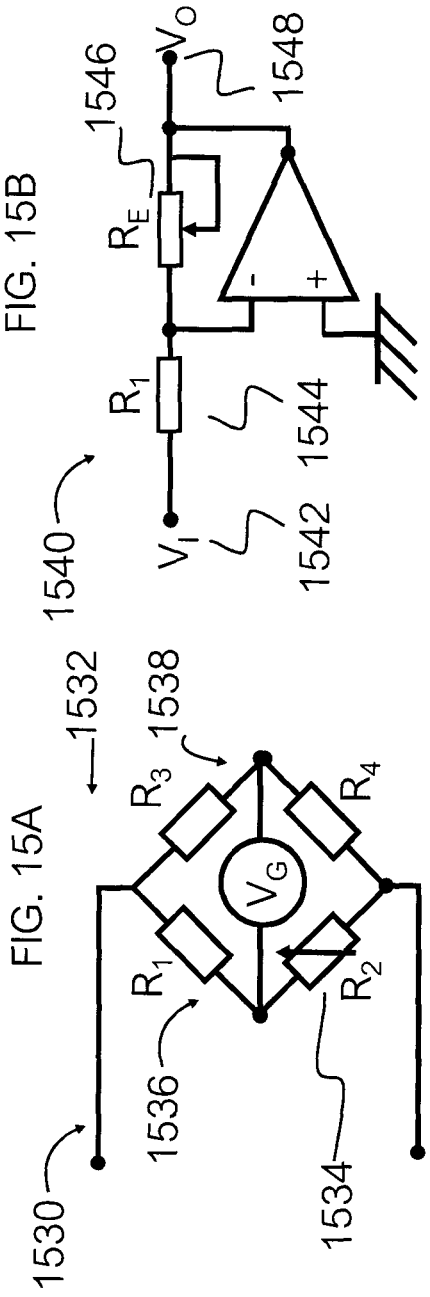
FIG. 15A
FIG. 15B
FIG. 15C
FIG. 15D

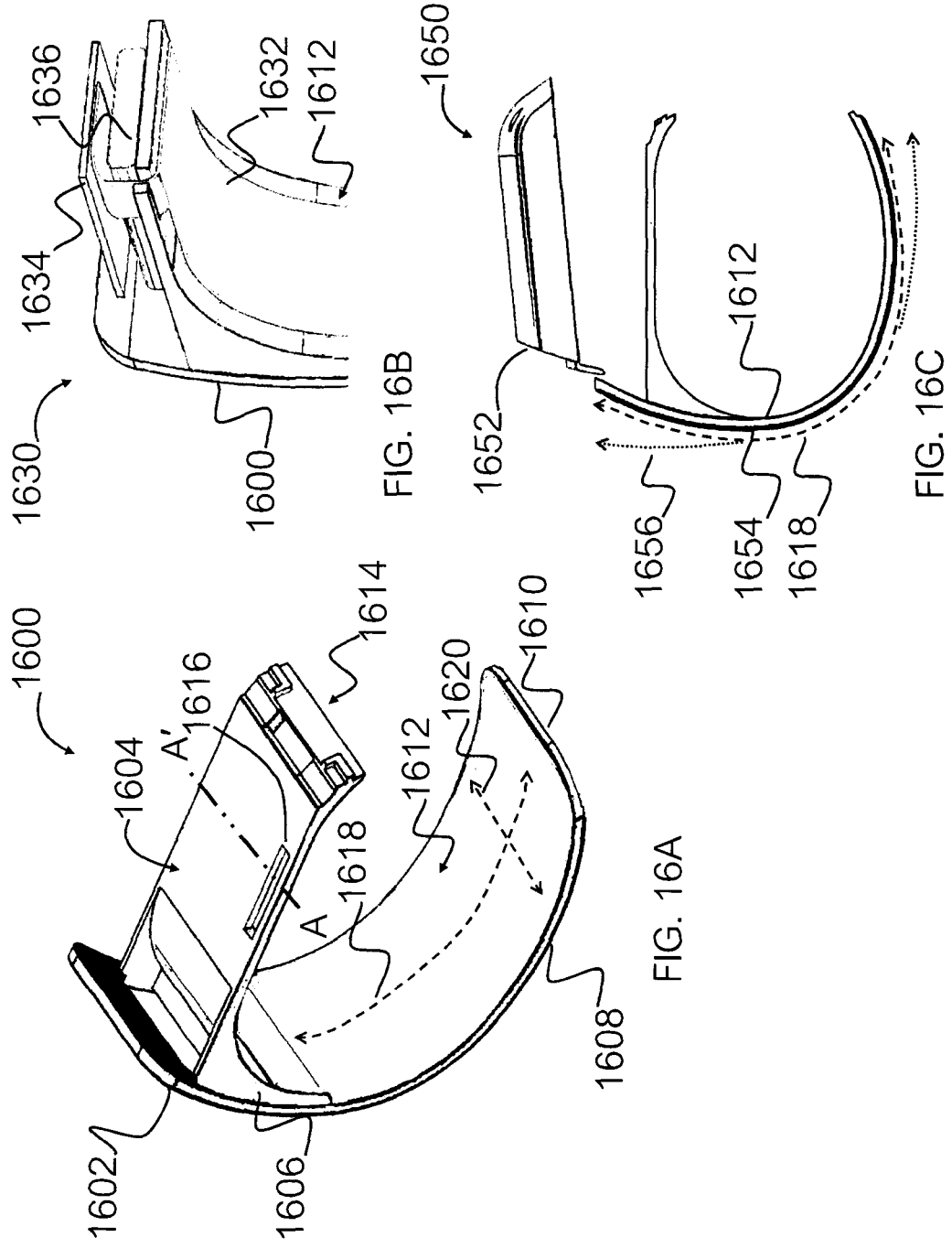

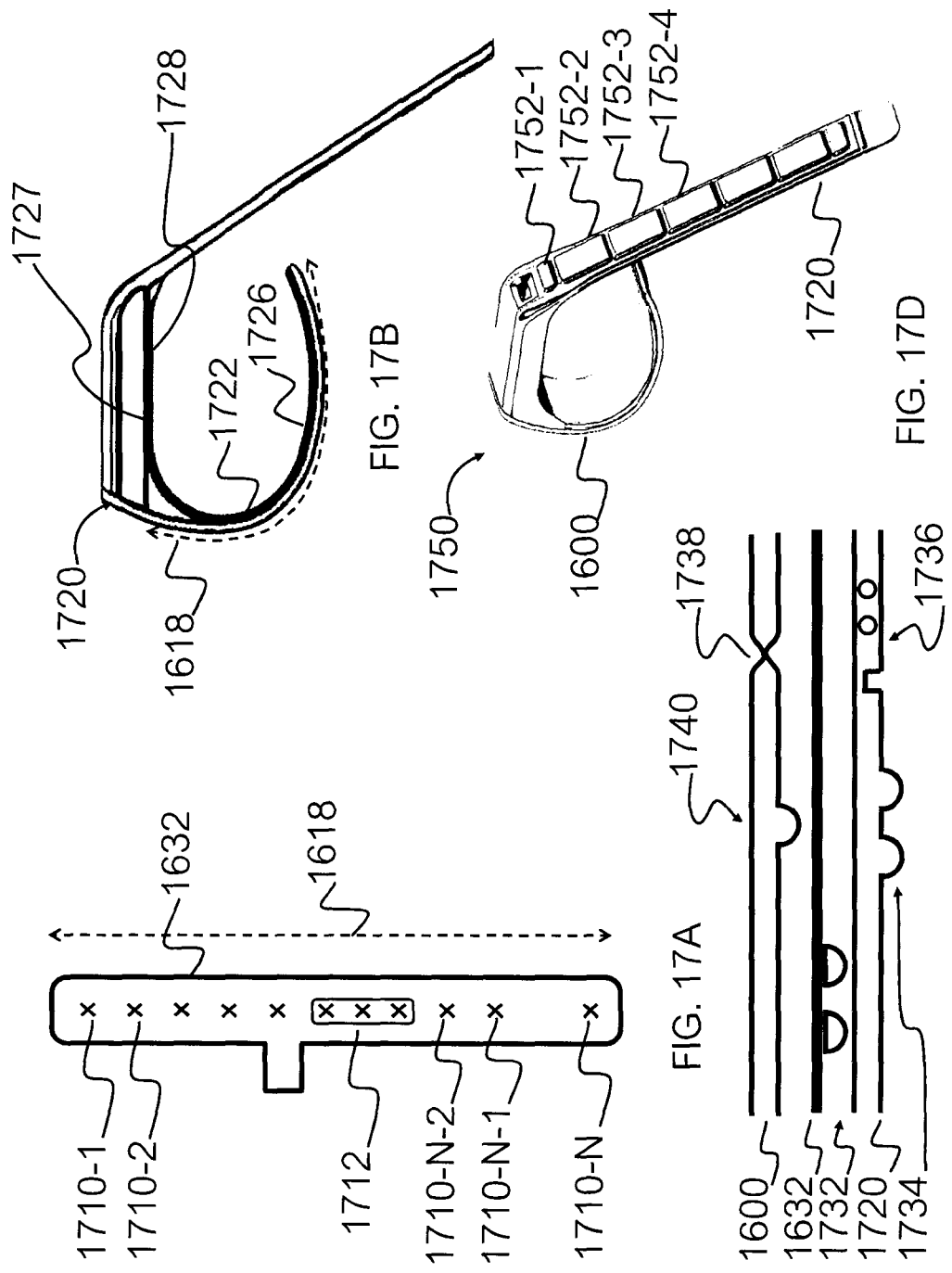

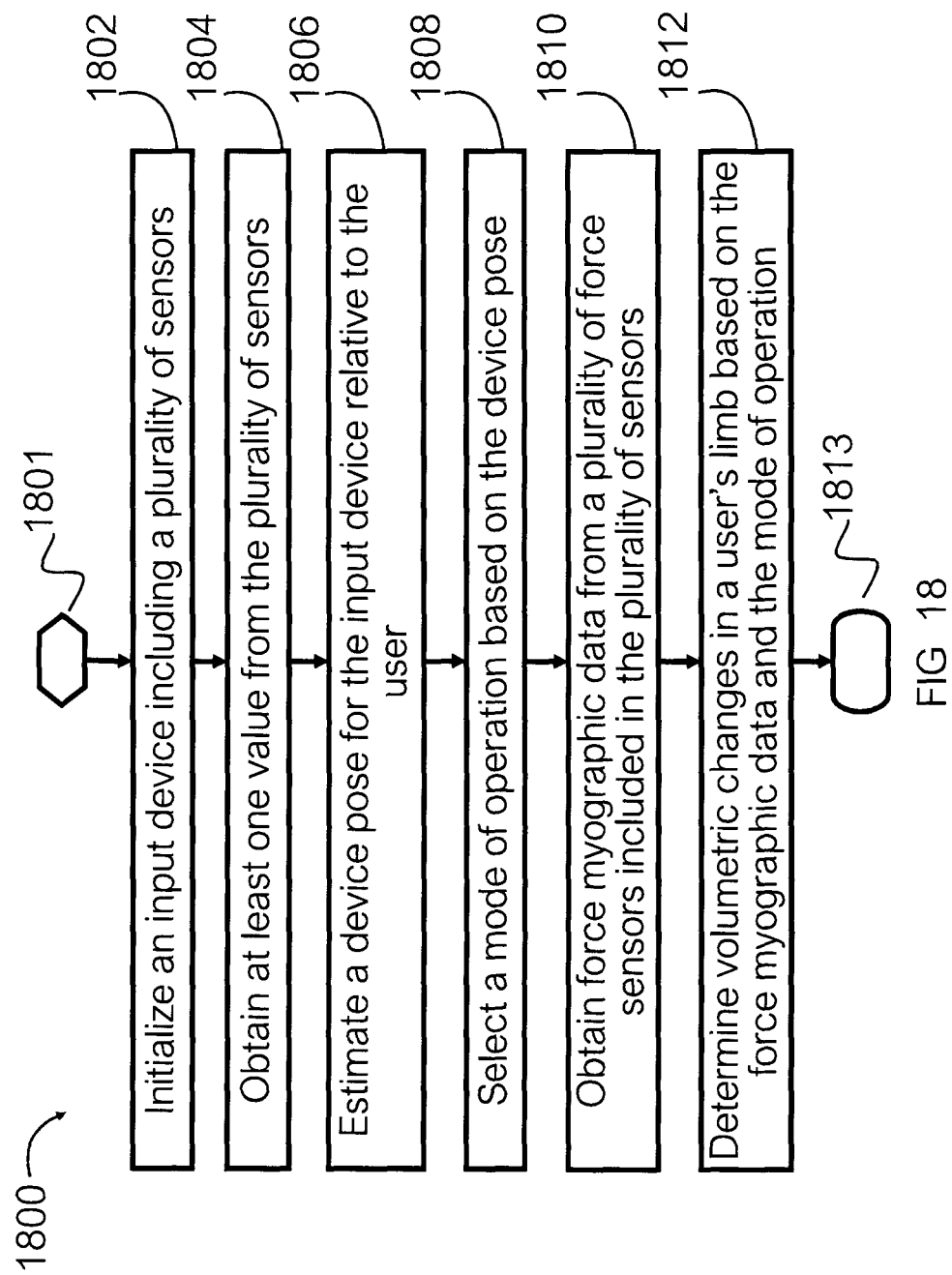

at least one processor to
obtain the data and provide a useful output.
APPARATUS AND METHODS FOR DETECTING, QUANTIFYING, AND PROVIDING FEEDBACK ON USER GESTURES

RELATED APPLICATIONS

This application is a U.S. National Phase of International Application No. PCT/CA2018/051435 filed on 13 Nov. 2018, which claims priority from U.S. Provisional Patent Application No. 62/585,709 filed on 14 Nov. 2017 and U.S. Provisional Patent Application No. 62/607,223 filed on 18 Dec. 2017, the contents of both are hereby incorporated by reference in their entireties.

TECHNICAL FIELD

This disclosure relates generally to input devices and more particularly to wearable devices worn by a user. More specifically, the wearable devices, in response to execution of processor-executable instructions, detect user gestures (e.g., pose, motion, or combinations thereof) of the body part proximate, or more distally disposed, to the wearable device as well as provide for monitoring and analysis of the body part.

BACKGROUND

A user interface device or interface device is a hardware component, or system of components, which allows a user to interact with a processor-based device, e.g., a computer, a phone. Interface devices may be divided into input, output, and hybrid devices. Input devices include components, or systems of components, that in response to user action create processor-readable data. These components, or systems, may include one or more buttons, keyboard, microphone, touch surface, and mouse. Output devices receive processor-readable data, and in response, create user interpretable (e.g., readable) output, or the like. These devices or components include displays, speakers, and haptic displays. A hybrid device includes input components and output components, e.g., touch screen.

An interface device may receive input from an extremity of user's body, e.g., hand, foot, tongue. However, input may be received from a more proximal location, such as, a wrist, forearm, or ankle. One method to detect input from a more proximal location on a user's body is to measure signals that move muscles and tendons, or the signals generated from the motion of the same. Such methods include myographic methods. Myographic methods include measurement, observation, or recordation of muscular contractions and relaxations. Two known myographic methods are electromyography (EMG) and force myography (FMG).

Electromyographic methods include measurement of electrical activity of one or more muscles via electrodes placed on the body, e.g., in or on limb. The electrodes may be surface electrodes (e.g., placed on skin) for so called sEMG method, or in vivo, e.g., placed in the musculotendinous complex. The latter is an invasive method. In EMG, a circuit is coupled to the electrodes and electrical potential therein changes in response to muscle movement. For example, electrodes on a surface of a limb measure voltage changes in response to movement of the underlying musculotendinous complex.

Force-myographic methods process signals from force (e.g., force, pressure, strain) sensors proximate to a body part, e.g., limb. Force myography (FMG) is also known as, creating muscle pressure maps, topographic force maps, and residual kinetic images. FMG measures localized volumetric changes in a limb, which can be indicative of the state of the muscles (e.g. recruitment, lactic acid build-up) within the limb, and the state of the tendons (e.g. position, elongation, tension) within the limb.

BRIEF SUMMARY

According to a first aspect of the invention there is provided an apparatus including: at least one peripheral device worn by a subject-user and having one or more sensors; at least one processor for receiving and processing data from the one or more sensors; a peripheral device interface communicatively coupling the at least one peripheral device with the at least one processor; at least one tangible computer-readable storage device communicatively coupled to the at least one processor and which stores processor-executable instructions which, when executed by the at least one processor, cause the at least one processor to obtain the data and provide a useful output.

According to a second aspect of the invention there is provided an apparatus including: a band; an inertial sensor physically coupled to the band; a plurality of force sensors physically coupled to the band; at least one processor communicatively coupled to the inertial sensor and the plurality of force sensors; and at least one nontransitory processor-readable storage device communicatively coupled to the at least one processor, which stores processor-executable instructions which, when executed by the at least one processor, cause the at least one processor to: receive a first set of inertial measurement data from the inertial sensor; generate limb pose information from the first set of inertial measurement data, wherein the limb pose information represents a pose of a limb of a user that wears the band; receive a set of force data from the plurality of force sensors, wherein the first set of force data represents volumetric properties of the limb proximate to the band; generate, from the first set of force data, extremity pose information, wherein the extremity pose information represents pose of an extremity of the user more remotely disposed than the band; and generate gesture information from the limb pose information, and the extremity pose information.

According to a third aspect of the invention there is provided a method of monitoring and analyzing an extremity of a subject-user by way of an apparatus including at least one processor, at least one inertial sensor in communication with the at least one processor, a plurality of force sensors in communication with the at least one processor, and a band physically coupled to the plurality of force sensors and the at least one inertial sensor, the method including: receiving, by the at least one processor, a first set of inertial measurement data from the inertial sensor; generating, by the at least one processor, limb pose information from the first set of inertial measurement data, wherein the limb pose information represents a pose of a limb of a user that wears the band; receiving, by the at least one processor from the plurality of force sensors, a first set of force data which represents volumetric properties the limb proximate to the band; generating, by the at least one processor from the first set of force data, extremity pose information which represents pose of an extremity of the user more remotely disposed than the band; and generating, by the at least one processor, gesture information from the limb pose information, and the extremity pose information.

According to a fourth aspect of the invention there is provided a method of monitoring and analyzing an extremity of a subject-user by way of an apparatus including at least one processor in communication with a plurality of sensors that comprise a plurality of force sensors, the method including: obtaining, by the at least one processor, at least one value from the plurality of sensors; estimating, by the at least one processor; a device pose for the input device relative to a user; selecting, by the at least one processor, a mode of operation of the plurality of sensors and the at least one processor based on the device pose; obtaining, by the at least one processor, force myographic data from the plurality of force sensors; and determining, by the at least one processor, volumetric changes in a limb of the user based on the force myographic data and the mode of operation.

According to a fifth aspect of the invention there is provided a method of monitoring and analyzing an extremity of a subject-user by way of an apparatus including at least one processor, at least one wearable device which when worn by a first user is disposed near a joint, and wherein the at least one processor and the wearable device are in communication, the method including: causing, by the at least one processor, to be presented to the first user, direction information that represents one or more poses or one or more change in poses for the joint; obtaining, by the at least one processor, pose data for the joint; generating, by the at least one processor, gesture data from the pose data; and quantifying, by the at least one processor, performance of the first user at the one or more poses or one or more change in poses for the joint.

According to a sixth aspect of the invention there is provided a method of monitoring and analyzing an extremity of a subject-user by way of an apparatus including a wearable device including a plurality of sensors, and wherein, when worn by a first user, is disposed near a joint, and at least one processor in communication with the wearable device the method including: obtaining, by the least one processor, via the plurality of sensors, pose data for the joint; generate, by the least one processor, gesture data from the pose data; quantifying, by the least one processor, a gesture for the user; obtaining, by the least one processor, feedback threshold data; determining, by the least one processor, if feedback should be provided to user per the feedback threshold data; and if feedback should be provided, causing, by the least one processor, a feedback signal to be sent to the wearable device.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Apparatus and methods in accordance with the present invention are described in greater detail herein with reference to the following figures in which:

FIG. 2A is a perspective view illustrating an exemplary wearable device as an example of a peripheral device shown in FIG. 1;

FIG. 2B is an elevation view illustrating the exemplary peripheral device shown in FIG. 2A;

FIGS. 3A through 3E are schematic diagrams illustrating a human forearm and hand in a plurality of poses;

FIGS. 4A and 4B are schematic diagrams illustrating a pose for a human forearm;

FIGS. 7 through 14 are flow-diagrams illustrating additional implementations of methods in accordance with the present invention;

FIGS. 15A through 15D are schematic diagrams illustrating portions of one or more measurement circuits and sensors applicable to the present invention;

FIGS. 16A and 16B are a perspective views illustrating an exemplary semi-rigid web that may be included in the inventive apparatus;

FIG. 16C is an elevation view illustrating an exemplary semi-rigid web that may be included in the inventive apparatus;

FIG. 17A is a schematic view illustrating a plurality of force sensors applicable to the present invention;

FIG. 17B is an elevation view illustrating a flexible web that may underlie at least a part of the web shown in FIGS. 16A through 16C;

FIG. 17C is a schematic view illustrating a plurality of features that may be included in or proximate to the exemplary semi-rigid web or a flexible web;

FIG. 17D is an elevation view illustrating a flexible web and a semi-rigid web having a link like structure;

FIGS. 18 through 22 are flow-diagrams of implementations of methods in accordance with the present invention;

DETAILED DESCRIPTION

Figure 1:
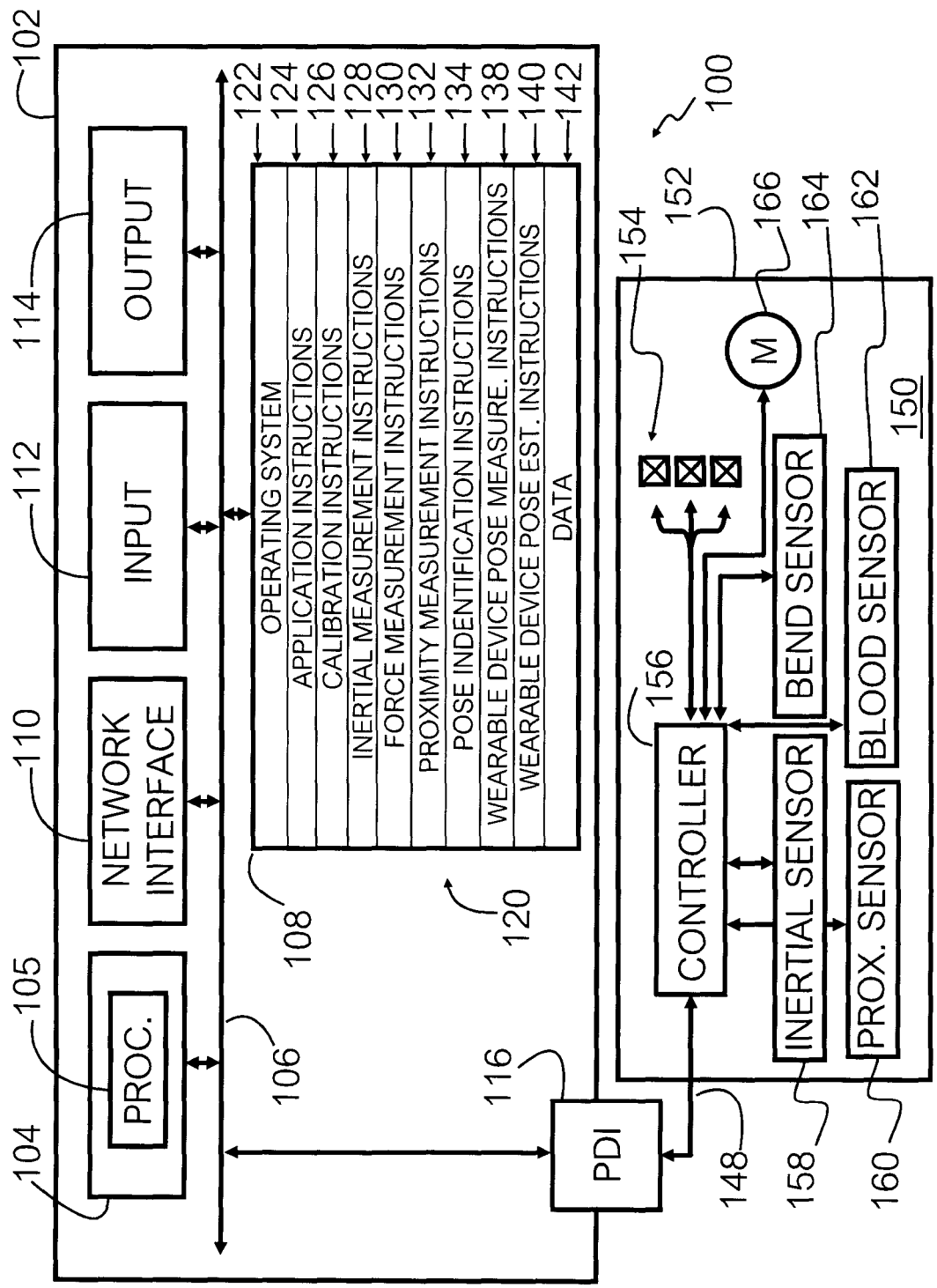
FIG. 1 is a schematic diagram illustrating an apparatus in accordance with the present invention including a digital computer and a peripheral device.

In general, the present invention provides apparatus and methods related to wearable devices with practical applications in the gaming, artificial intelligence, and medical arts. A wearable device in accordance with the invention operates in response to execution of processor-executable instructions so as to detect and quantify user gestures (e.g., pose, motion, or combinations thereof) of the user's body part proximate, or more distally disposed, to the wearable device as well as provide for monitoring and analysis of the given body part or other connected body parts. Examples of body part monitoring and analysis are provided herein below and may include implementations such as, but not limited to, detection of a user-subject's hand grip-strength, tendon monitoring such as tendon tension, elongation, contraction, positioning, muscle monitoring such as muscle movement, recruitment, volume, wrist, forearm, or hand tracking, and/ or any other user physicality. Although an exemplary embodiment of a wearable device is shown and described herein in the form of a wrist band, it should be readily apparent that the inventive wearable device may take other forms without straying from the intended scope of the present inventive methods and apparatus.

Disclosed herein are apparatus and methods with practical application in computing including user input, and display of information. The present disclosure includes methods and apparatus that, in part, detect, quantify, or otherwise classify gestures (e.g., motion and/or pose) of a user of a wearable device. A gesture is one or more poses or changes in pose of one or more parts of a body. Detection includes detecting a motion, i.e., change in pose. Quantification includes assigning a qualitative or quantitative measure to the pose or change in pose. Classification includes where a machine (e.g., processor-based device) receives feature values or characteristics for one or more objects and identifies which group or class the one or more objects belong to. For example, receiving processor readable-information created by one or more sensors may be in response to the movement of an overall limb of a subject-user, the movement of an extremity of the subject-user's limb, and/or the movement (e.g., torsional rotation) of a joint between the limb and the extremity. Combinational poses of these limb, joint, and/or extremity movements form pose data and thereby create a given gesture. That is, a gesture can be defined as one or more poses or the transition between poses. Classification may include a train time or phase in which feature values are associated with classes, e.g., supervised training where the machine learns association from feature values to known class labels or unsupervised training where the machine learns patterns or structure in a plurality of feature values. Other variants of training are possible. At run time after a suitable train, or train and validate phase(s), the machine (e.g., a processor-based device executing processor-executable instructions based on, in part, the train phase) identifies classes for feature values. The classification has two levels including detecting a gesture and grading the gesture against some feedback threshold. The classification by the machine is ideally robust to allow for a wide plurality of input to be accurately mapped to the correct classes. However, in force myography many factors make classification fragile. This disclosure includes methods and apparatus which obtain force myographic data, combine the force myographic data with other data (i.e., sensor fusion: processing data received from sensors of different types), and detects, quantifies, or grades user gestures based in part on the force myographic data or the other data.

In one illustrative implementation of the invention, this disclosure includes apparatus and methods which obtain force myographic data from a user's wrist and forearm for, at least, a user's wrist, hand, or fingers when the user's forearm in a range of poses. That is, to create more robust classifications, use pose as a precondition to classification by the methods and apparatus disclosed herein. Feature values from a plurality of force sensors (e.g., myographic data) may be affected by many factors including intra-user and inter-user factors. These include: tightness of band, fatigue of user, location of band, inter user characteristics, and the like. As such, classification may not be robust. However, if the pose of the user's forearm is within a range of predefined poses then classification of wrist or wrist and finger poses is easier. Such predefined poses may be any set of anatomical variations which are effectively a continuously variable range. The one or more forearm or wrist poses may be called a gesture and used as an input for a processor-based device.

This disclosure includes apparatus and methods that may classify force myographic data for a user's wrist, hand, or fingers based on input from a plurality of force sensors and at least one proximity sensor. Identification of a pose of an extremity based on a first sensor type (e.g., force) is not always possible or desirable. That is, the pose is possibly in two or more classes. Data from a second sensor type (e.g., proximity) may be used to disambiguate classification into the two or more classes. This may also include sensors such as luminosity sensors which may detect, for example, the shadow of the wrist.

Proximity sensing may be accomplished via line-of-sight or non-line-of-sight methods. Line-of-sight methods may include, those such as, but not limited to, time-of-flight measuring, luminosity and/or shadow sensing, or cameras. Non-line-of-sight methods may include capacitive sensing. The advantage of non-line-of-sight methods lends this technology to continuous, ubiquitous monitoring in unconstrained environments. Moreover, multi-modal approaches will have better accuracy. Within line-of-sight methods, the different technologies have different sensing areas. For example, cameras, or several strategically placed time-of-flight sensors would be able to monitor/identify individual digits on an extremity. There are instances where it may be preferred to combine two line-of-sight methods. For instance, time-of-flight and luminosity may be a preferable proximity sensor combination for situations where it is desired to remove confounding readings from objects that are within range, but are not the extremity. For instance, if the given time-of-flight sensor detects an object in range, but the luminosity sensor is low, such may be indicative of the user having the wearable device within their pocket, or on a table, as opposed to a relevant body part itself being in front of the sensor.

This disclosure includes apparatus and methods which classify one or more poses of a user's limb after receipt of sensor data that show the user's extremity is in a range of predetermined extremity poses. The sensor data may be force myographic data or proximity data for, at least, a user's wrist, hand, or fingers. The one or more poses, given receipt of force myographic data, may be an input for a processor-based device. That is, in some implementations, the force myographic data is a pre-condition to classify pose of a limb. For example, if the pose of the user's hand or wrist is within a range of predefined poses then classification of arm or forearm poses is easier.

This disclosure includes apparatus and methods that may process FMG data instead of, or in addition to, electromyographic (EMG) data. EMG does not allow a machine to monitor the state of tendons and ligaments. EMG data also has low signal to noise ratios and practical disadvantages related to skin impedance and suitable electrodes. FMG involves the detection of changes in the shape of skin that overlies a musculotendinous complex. A change in volume of a body part indicates a change in state of the musculotendinous complex, including, but not limited to, changes in state of muscles, tendons, and ligaments. The musculotendinous complex may be on many locations on a body and is not limited to limbs, muscle groups of a particular size, and the like. Additionally, when compared to EMG, FMG advantageously requires less complex or costly signal acquisition systems, devices, and methods. Examples, of force sensors include force sensitive resistors. The force sensors in combination with a reference body (e.g., frame or band) measure changes in volume of musculotendinous complex, e.g., limb, forearm. For example, force sensors may measure localized changes in the musculotendinous complex. In some implementations, force sensors measure a plurality of localized changes in the musculotendinous complex.

This disclosure includes apparatus and methods which obtain force myographic data obtained from force sensors and other data obtained from at least one other sensor. This disclosure includes methods and apparatus which improve acquisition and use of force myographic data obtained from a user (e.g., operator, patient, wearer). Feature values from a plurality of force sensors (e.g., myographic data) may be affected by many factors including intra-user and inter-user factors. These include: pose of the device (e.g., tightness of band), fatigue of user, location of band, inter user characteristics, and the like. As such, classification may not be robust. However, if one or more attributes of how the device is being worn by the user (e.g., pose of device) are determined then classification of extremity pose is easier. See, for example, FIG. 18 and FIG. 21. If a controller (e.g., processor) obtains one or more attributes of how the device is being worn by the user the controller may select a mode of operation for the device to compensate, e.g., compensate when the pose device is off nominal. See for example, FIG. 18. Additionally, or alternatively, the controller may adjust the pose of the device. See for example, FIG. 1 and FIG. 22.

FIG. 1 illustrates apparatus 100 in accordance with the present invention including one or more specialized devices to process information. Apparatus 100 includes a digital computer 102 communicatively coupled to other devices and systems. Digital computer 102 includes control subsystem 104 including at least one processor 105, communicatively coupled to at least one bus 106. Digital computer 102 further includes at least one tangible non-transitory computer- and processor-readable storage device 108, a network interface subsystem 110, user input subsystem 112, output subsystem 114, and a peripheral device interface subsystem 116, all communicatively coupled to bus(s) 106. Apparatus 100 further includes a peripheral device 150. In the context of the present application, the peripheral device is a wearable device (e.g., wrist band) intended for attachment to an extremity (e.g., any part of any limb such as, but not limited to, a wrist) of a user. Though any particular form of wearable device may be provided without straying from the intended scope of the present invention, the exemplary embodiment discussed herein will be limited only for purposes of clarity in illustration to a band worn on a wrist of a subject-user. For purposes of the present description, it should be understood that a subject-user includes any individual wearer of any type of peripheral device in accordance with the present invention including, but not limited to, a band worn on a wrist.

The at least one processor 105 may be any logic processing unit, such as one or more digital processors, microprocessors, central processing units (CPUs), graphics processing units (GPUs), application-specific integrated circuits (ASICs), programmable gate arrays (PGAs), programmed logic units (PLUs), digital signal processors (DSPs), network processors (NPs), and the like.

Network interface subsystem 110 includes communication circuitry to support bidirectional communication of processor-readable data, and processor-executable instructions. Network interface subsystem 110 may employ communication protocols (e.g., FTP, HTTPS, SSH, TCP/IP, SOAP plus XML) to exchange processor-readable data, and processor-executable instructions over a network or non-network communication channel (not explicitly illustrated) such as, Internet, a serial connection, a parallel connection, ETHERNET®, wireless connection, fiber optic connection, combinations of the preceding, and the like. In some implementations, apparatus 100 is operated as a distributed system.

User input subsystem 112 includes one or more user interface devices such as keyboard, pointer, number pad, touch screen, or other interface devices for a user, e.g., human operator. User input subsystem 112 may include peripheral device 150. In some implementations, user input subsystem 112 includes one or more sensors for digital computer 102. The one or more sensors provide information characterizing or representing the environment or internal state of digital computer 102. Further, output subsystem 114 includes one or user interface devices such as, display, lights, speaker, and printer. In some implementations, input subsystem 112 and output subsystem 114 are included in the peripheral device 150.

Storage device(s) 108 include at least one nontransitory or tangible storage device. Storage device(s) 108 may, for example, include one or more volatile storage devices, for instance random access memory (RAM); and one or more non-volatile storage devices, for instance read only memory (ROM), flash memory, magnetic hard disk, optical disk, solid state disk (SSD), and the like. A person of ordinary skill in the art will appreciate that storage may be implemented in a variety of ways, such as, read only memory (ROM), random access memory (RAM), hard disk drive (HDD), network drive, flash memory, other forms of computer- and processor-readable storage media, and/or a combination thereof. Storage may be read-only or read-write. Further, modern computer systems may conflate volatile storage and non-volatile storage, for example, caches, solid-state hard drives, in-memory databases, and the like.

Storage device(s) 108 includes or stores processor-executable instructions and/or processor-readable data 120 associated with the operation of apparatus 100. Execution of processor-executable instructions and/or processor-readable data 120 causes the at least one processor 105, and/or control subsystem 104, to carry out various methods and actions, for example, via network interface subsystem 110, or peripheral device interface subsystem 116. Processor-executable instructions and/or processor-readable data 120 may, for example, include a basic input/output system (BIOS) (not explicitly illustrated), an operating system 122, peripheral drivers (not explicitly illustrated), application instructions 124, calibration instructions 126, inertial measurement instructions 128, force measurement instructions 130, proximity measurement instructions (132), (limb) pose identification instructions 134, capacitor measurement instructions (not explicitly illustrated), device pose measurement instructions 138, device pose estimation instructions 140, and processor readable data 142.

Exemplary operating system 122 include LINUX®, and WINDOWS®. Application instructions 124 include processor-executable instructions that, when executed, cause apparatus 100 to perform one or more actions associated with an application, e.g., perform computations on digital computer 102 based on processor readable data from peripheral device 150. Application instructions 124 may obtain (e.g., receive) processor-readable input information including inputs via peripheral device 150 and other processor-executable instructions, such as, pose identification instructions 134.

Calibration instructions 126 include processor-executable instructions, that, when executed by a processor (e.g., processor(s) 105) cause the processor to calibrate and store the calibrated values for peripheral device 150. Components included in or on peripheral device 150 may have parameters with inter-component variation, temporal variation, variation from ideal or expected values, or the like. Calibration instructions 126, when executed by a processor, test and, as needed, correct these inter-component variation, temporal variation, and/or variation from expected or ideal component parameters.

It should be readily apparent that although processing (i.e., via processor 105) is shown in FIG. 1 as being distinct from the peripheral device 105, the present invention may be implemented where the entire apparatus will a single integration; i.e. all processing, input and feedback from/to the user will take place an integrated wearable device.

Inertial measurement instructions 128, force measurement instructions 130, proximity measurement instructions (132), and device pose measurement instructions 138, when executed by a processor (e.g., processor(s) 105) cause the processor to receive and process data from one or more respective sensors. Inertial measurement instructions 128 when executed by a processor cause the processor to identify a pose of an inertial sensors, such as, an inertial sensor included in peripheral device 150. Examples of inertial sensors and operation of the same are discussed herein in relation to, at least, FIGS. 1, 2A through 2D, 6, and 10 through 12.

Force measurement instructions 130 when executed by a processor cause the processor to obtain (e.g., receive) data from a plurality of force sensors and measure physical characteristics of one or more musculotendinous complexes via myographic methods. Examples of force sensors and operation of the same are discussed herein in relation to, at least, FIGS. 1, 2A through 2D, 6, 9A through 9C, 12, 15, 17, 18, and 21.

Figure 16D:
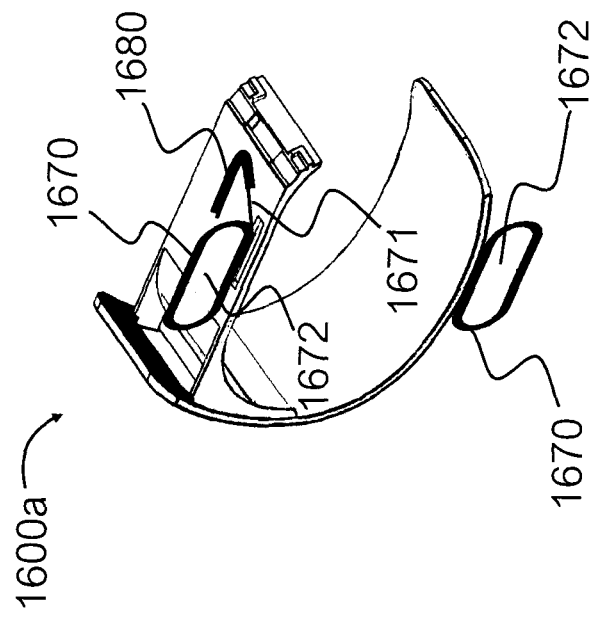
FIG. 16D is an alternative embodiment to FIG. 16A.

Proximity measurement instructions 132 when executed by a processor cause the processor to receive data from one or more proximity sensors and identify, in part, a pose of a user's extremity. The proximity measurement instructions 132 may, when executed, perform a range measurement, e.g., time of flight measurements, count of return pulses. Examples of proximity sensors and operation of the same are discussed herein in relation to, at least, FIGS. 1, 2A through 2D, 10, and 11. The proximity measurement instructions 132 may invoke the capacitor measurement instructions (not explicitly illustrated). Capacitance may be utilized to detect proximity by any suitable manner. One preferable manner of capacitive proximity sensing may involve sensing change in capacitance as a user's extremity is brought into close proximity with the capacitive sensor. In such manner, the apparatus may include (as shown by the wearable device 1600a in FIG. 16D) a shielded wire with an exposed end 1671 to form an antenna which brings the sensing area close to the user's body part. Such wire would be shielded along its length 1680 with any suitable electromagnetic shielding material except for a loop 1670 to focus sensitivity. The loop 1670 may be any suitable shape and not intended to be limited to the oval shape as shown. Such sensitivity may be enhanced with copper tape 1672 (or any suitable conductive material) wherein loop size and copper tape are adjustable to tradeoff between increased sensitivity versus an acceptable sensing range.

Pose identification instructions 134 when executed by a processor cause the processor to identify a pose of one or more parts of a user's body, such as, a limb or an extremity. The pose identification instructions 134 may identify a pose, a change in pose, quantify the degree of a pose (e.g., joint angle) or change in pose, and the like for one or more parts of the body (i.e., limb, joint, and/or extremity). The pose identification instructions 134 may receive processor-readable data from the output of the inertial measurement instructions 128, force measurement instructions 130, proximity measurement instructions 132, or capacitor measurement instructions (not explicitly illustrated). The pose identification instructions 134 may generate processor-readable information that further processor-executable instructions may interpret as an input (e.g., command) for digital computer 102, or peripheral device 150. For example, pose identification instructions 134 may provide input to application instructions 124. Examples of pose identification are discussed herein in relation to, at least, FIGS. 6, and 9 through 12.

Capacitor measurement instructions (not explicitly illustrated) when executed by a processor cause the processor to identify one or more capacitance values for one or more capacitors in apparatus 100. For example, the capacitor measurement instructions may detect a change in capacitance when there is a change in the ambient environment to the peripheral device 150. For example, a user passes one or more parts of the body near a capacitor or capacitive sensor included in peripheral device 150. The capacitor(s) or capacitive sensor(s) may detect the presence of a hand when a wrist is in flexion or extension.

Device pose measurement instructions 138 when executed by a processor cause the processor to obtain data from one or more sensors for a pose of a wearable device relative to a user's body. Pose is an attribute of a body which may include one or more of position, orientation, arrangement, and the like, relative to a reference frame, or another body. Device pose may include device tightness on a limb, gap between device and limb, proximity to center of body (e.g., more proximal, more distal), rotational position of device on limb, and the like. The device pose measurement instructions 138 may, when executed, measure physical quantities relating to where a wearable device sits on a limb, tightness of the device about the limb, and the like. Examples of one or more sensors and operation of the same are discussed herein relation to, at least, FIGS. 1, 2A through 2D, and 17.

Device pose estimation instructions 140 when executed by a processor cause the processor to estimate (e.g., identify, calculate) a pose of a wearable device relative to a user's body. The device pose estimation instructions 140 may invoke the device pose measurement instructions 138. The device pose estimation instructions 140 may process photoplethysmographic data, deflection data, myographic force data, or the like obtained from one or more sensors, e.g., by executing device pose measurement instructions 138.

Data 142 may include processor-readable information or data used, obtained, created, or updated by the operation of apparatus 100. For example, one or more logs from digital computer 102 and peripheral device 150. Data 142 may include processor-readable data including parameters used in the operation of apparatus 100. Data 142 may include processor-readable data associated with (e.g., created by, referred to, changed by) a processor executing processor-executable instructions, such as, application instructions 124, calibration instructions 126, inertial measurement instructions 128, force measurement instructions 130, proximity measurement instructions 132, capacitor measurement instructions (not explicitly illustrated), (limb) pose identification instructions 134, device pose measurement instructions 138, device pose estimation instructions 140, or the like.

Peripheral device interface (PDI) subsystem 116, at least, communicatively couples control subsystem 104 and peripheral device 150 by a wired or unwired network or non-network communication channel 148 disposed between digital computer 102 and peripheral device 150. Apparatus 100 may employ protocols such as BLUETOOTH® or WI-FI® in operation of communication channel 148. Communication channel 148 may operate in accordance with BLUETOOTH LOW ENERGY protocol under one or more profiles that specifies aspects of how peripheral device 150 works. Suitable profiles include Heart Rate Profile (HRP) or Human Interface Device over Generic Attribute Profile (HoGP). In some implementations, peripheral device 150 may include an electrical connector which may be part of a wired connection to digital computer and/or to other devices, e.g., by using suitable cables and physical connectors.

Peripheral device 150 includes a device body 152, for example, device body 152 includes a case or head physically coupled to a band, e.g., flexible strap. For example, the band may be rotatably connected to the head via one or more pins or flexibly connected via shared material in or on head and band. Peripheral device 150 includes a plurality of force sensors 154 physically coupled to device body 152 and communicatively coupled to a controller 156. Peripheral device 150 may include an inertial sensor 158 communicatively coupled to controller 156. In various implementations, peripheral device 150 includes a proximity sensor 160 communicatively coupled to controller 156. Peripheral device 150 may include a blood sensor 162 or a bend sensor 164 communicatively coupled to controller 156. In various implementations, peripheral device 150 includes an actuator 166 communicatively coupled to controller 156 and physically (e.g., connected, removably coupled) to device body 152.

Controller 156 may be any logic processing unit, described above. In various implementations, controller 156 includes communication circuitry that may form part of communication channel 148. In some implementations, controller 156 may be a microcontroller comprising a CPU, memory, input components, output components, and the like. The components may include voltmeters or analog to digital converters. The controller 156, in some implementations, samples signals from one or more sensors at a rate of tens of Hertz. The controller 156 may be a CYBLE-214015-01 microcontroller available from Cypress Semiconductor Corp., of San Jose, Calif., US.

Controller 156 is communicatively coupled to one or more of plurality of force sensors 154, inertial sensor(s) 158, proximity sensor(s) 160, and other sensors or components physically coupled to peripheral device 150. Peripheral device 150 may include one or more additional electrical components communicatively coupled to the controller 156 and one or more sensors, e.g., plurality of force sensors 154. The additional electrical components may include a voltage divider circuit, Wheatstone bridge, low pass filter, and the like. See FIG. 15 which illustrates such various ancillary electrical components.

The plurality of force sensors 154 may include one or more force sensors, pressure sensors, strain sensors, or a mix. In some implementations, the plurality of force sensors 154 includes one or more load cell, piezo-resistive sensor, piezo-electric sensor, and capacitive sensor. In some implementations, a force sensor in the plurality of force sensors 154 includes an instrument that acts as a transducer which in response to a force, e.g., push or pull, converts the force into a signal, e.g., time varying voltage in a circuit. A force sensor included in the plurality of force sensors 154 may include one or more mechanical components that in response to an applied force provide an action that may be used to create an output signal for the force sensor. A load cell is a transducer that is used to create an electrical signal whose magnitude is directly proportional to the force being measured and offer higher accuracy and linear output. For example, a load cell includes a combination of mechanical components (e.g., elastic diaphragm) and force measuring components. Examples of mechanical components includes fluid bladders, elastomeric material, and springs. The various load cell types include hydraulic, pneumatic, and strain gauge. In some implementations, the plurality of force sensors 154 includes a force sensitive resistor; an electrical component that in response to an applied force changes electrical impedance (e.g. resistance and/or reactance). Commercial and bespoke force sensitive resistors (e.g., TPE-500 series, Flexiforce, FSR®) are available from Tangio Printed Electronics of North Vancouver, BC, CA; Teksmay, Inc., South Boston, Mass., US; and Interlink Electronics, Inc., Westlake Village, Calif., US.

Proximity sensor(s) 160 may be physically coupled to device body 152, e.g., connected to head or band. The proximity sensor 160 may be oriented in a distal direction to capture motion of an extremity (e.g., foot, hand, toe, digit) relative to a more proximal body part (e.g., wrist, ankle). Proximity sensor(s) 160 may include a camera or a time of flight sensor. A camera, and associated processor executable instructions executed by a suitable control system may image the extremity and detect changes in the pose of the extremity relative to another point on the body, e.g., limb. A time of flight sensor measures the distance between sensor and target (i.e., extremity) by time of flight of a signal propagating in an environment, e.g., infrared pulses, sound pulses. In some implementations, a time of flight sensor measures the magnitude of the return from the target, e.g., counts number of pulses returned, where distance is inversely correlated with magnitude. An exemplary proximity sensor 160 is a VL6180X proximity sensor available from stMicroelectronics Naamloze Vennootschap, Geneva, GE, CH. Proximity sensor(s) 160 may include one or more capacitive sensor(s).

The inertial sensor(s) 158 may include one or more attitude sensors, accelerometers, compasses, gyroscopes, magnetometers, pressure sensors, and the like. Inertial sensor(s) 158 may be an inertial measurement unit (IMU) sensors, such as a six, nine, or ten axis IMU sensors. The inertial sensor(s) 158 in response to motion provides a signal which represents pose (e.g., location or orientation) or rate of change of pose (e.g., velocity or angular velocity) with regard to the inertial sensor(s) 158 and any connected body (e.g., peripheral device 150). The inertial sensor(s) 158 may be a MPU-9250 IMU sensor from InvenSense Inc. of San Jose, Calif., US.

In some implementations, peripheral device 150 includes one or more capacitors or capacitive sensors (not explicitly illustrated). The controller 156 may execute capacitor measurement instructions (not explicitly illustrated) to detect a change in capacitance for one or more capacitors included in peripheral device 150. In some implementations, the proximity sensor(s) 160 include one or more capacitive sensors.

The blood sensor(s) 162 may include one or more pulse oximeters, photoplethysmograph, and the like. Blood sensor(s) 162 may include one or more light sources (e.g., LED) of the same or differing wavelengths that emit light against the body of the wearer (e.g., user) and receive reflected or transmitted light back by one or more detectors. Some blood sensor(s) 162 include a red LED (e.g., with wavelength 600 nm, 620-645 nm, or 660 nm) and include an infrared LED (e.g., with wavelength 850 nm or 940 nm) to measure the disparate absorption and transmission of oxy-hemoglobin and deoxyhemoglobin as described in expired U.S. Pat. No. 4,880,304. Some blood sensor(s) include two or three LEDs emitting similar wavelengths (e.g., 780 nm, 785 nm, and 808 nm) that will scatter in the body to a similar extent reducing need for calibration. The optical detector may be a MAX86140 integrated circuit available from Maxim Integrated Products Inc. of San Jose, Calif., US. The optical detector may include a BPW34 photodiode available from Vishay Intertechnology, Inc., Malvern, Pa., US.

The bend sensor(s) 164 may include one or more bend or deflection sensors. Bend sensor(s) 164 may include a body and a variable resistor that changes resistance as the body bends (e.g., deviates, deflects) from an initial pose. An example of a bend sensor is a 2.2" 10 kOhm flex sensor available from Spectra Symbol Corp., Salt Lake City, Utah, US. In some implementations, bend sensor(s) 164 includes one or more force sensors and one or more bodies. Bend sensor(s) 164 may include a conductive or optical bend sensor. The bend sensor 164 may be oriented with respect to a first spatial extent, and in response to deviation from the first spatial extent generates a bend signal.

Peripheral device 150 may include one or more actuators 166. The actuator(s) 166 may include one or more motors (M), electro-activated components (not explicitly illustrated), and the like, which when activated adjust the pose of peripheral device 150 relative to a user's body. For example, such actuator(s) may act to selectively constrict or slacken around a limb. Motors may include linear electric motors and rotatory electric motors. Electro-activated components included electro-activated polymers that contract in response to an applied electric current. The one or more actuator(s) 166 may be coupled to one or more bodies or members that allow the controller 156 to cause, via the peripheral device 150 to constrict or relax around a user's limb.

In some instances, the wrist band in accordance with the present invention may also be supplemented by external sensors that may include: IMU sensors placed on the fingers or hand for detecting the orientation of the proximal phalange of a finger or fingers, IMU sensors placed on the fingers or hand for detecting the orientation of the dorsal part of hand, or force sensors mounted on the palmar side of the hand to detect palmar interaction with objects.

Peripheral device 150 or digital computer 102 may be coupled to one or more ancillary sensors (not explicitly shown). The ancillary sensors may be integrated with or separated from peripheral device 150, e.g., worn at a more distal location and be additional to sensors within the peripheral device 150. An example of an additional ancillary sensor is an inertial sensor placed perhaps on a user's fingers which may include one or more attitude sensors, accelerometers, compasses, gyroscopes, magnetometers, pressure sensors, and the like. Inertial sensor(s) may be an IMU sensor. In some implementations, a user may wear inertial sensor(s) in one or more fingers. The inertial sensor(s) may be worn on the dorsal side of a hand or caudal side a foot. In the present wrist band embodiment of the present invention, ancillary sensors are preferably provided to detect the difference in attitude and heading reference system (AHRS) angle estimates for a knuckle IMU versus a band IMU—and hence to detect the angles made by the wrist joint—for assessment, and also to train and/or identify relations between other sensors within the band or other ancillary sensors and this angle measurement, such that prediction of angles may continue when the ancillary IMU on the knuckle has been removed.

Inertial sensor(s) may also provide ancillary data to other sensors, e.g., force sensors 154. The ancillary data, provided by the inertial sensor(s) may provide information on the pose, or change in pose, of one more parts of the body, e.g., parts placed distal to location for force sensors 154. Use of the ancillary data is described herein at least in relation to FIGS. 9A through 9C.

In some other instances, cases the ancillary sensors may not be an active sensor, but rather may instead be a beacon. For instance, a strong magnet on the finger as an ancillary element, and a magnetometer within the wrist band. The reverse may also be true, an ancillary sensor, and a beacon on the band. Furthermore, as noted above, the signals derived from the combination of the wrist worn and ancillary sensor/beacon may be used: 1) Directly—e.g. tactile force measurement, wrist angle quantification or 2) Indirectly—to derive relationships between signals on the band and tactile force or signals on the band and wrist angles.

An additional example of an ancillary sensor is a force sensor which may include one or more sensors described herein. Force sensor may be worn on the palmar side of a hand or plantar side a foot. The force sensor when worn on the palmar side of hand may provide data on interaction with an item. Force sensor(s) when worn on the plantar side of foot may provide information on user's gait or balance.

In some implementations, peripheral device 150 includes one or more tangible storage devices which stores processor-executable instructions and/or processor-readable data associated with the operation of peripheral device 150. The processor-executable instructions and/or processor-readable data stored in peripheral device 150, may include processor-executable instructions and/or processor-readable data found in processor-executable instructions and/or processor-readable data 120. For example, peripheral device 150, may include a basic input/output system (BIOS) (not explicitly illustrated), an operating system 122, peripheral drivers (not explicitly illustrated), application instructions 124, calibration instructions 126, inertial measurement instructions 128, force measurement instructions 130, proximity measurement instructions 132, pose identification instructions 134, capacitor measurement instructions (not explicitly illustrated), and data 142.

FIG. 2A is a perspective view illustrating an exemplary wearable device 200, an implementation of the peripheral device 150. FIG. 2B is an elevation view illustrating the wearable device 200. In some implementations, wearable device 200 is sized and shaped like wristwatch including at least two parts with a watch head 202 physically coupled to a band (collectively 204A and 204B).

In various implementation, watch head 202 includes a display 205 where a user may review information presented by wearable device 200. Examples of the display 205 includes lights, screen, touch screen, and/or haptic display. In some implementations, watch head 202 includes one or more input component (not explicitly illustrated) where the user may provide information to wearable device 200 and communicatively coupled devices, e.g., components in apparatus 100. The one or more input component may include buttons, touchscreen, components described in FIG. 1, or the like. In some implementations watch head 202 or a band (collectively 204A and 204B) include a haptic display component such as device that stimulates somatic receptors including rumble motors and kinesthetic actuators.

In various implementations, head 202 includes a controller, power source, and one or more sensors, such as, an inertial measurement unit, or a proximity sensor. The head 202 may be disposed on the outside or the inside of the subject-user's wrist. In some implementations, wearable device 200 includes two or more heads. A first head may include sensors and circuitry described herein and a second head may include the same or at least one other device like a watch (e.g., time keeper circuitry and display), smart watch (e.g., processor-based device and display) integrated with or separable from the invention. In some implementations, wearable device 200 includes an interface that allows temporary, or reversible, mechanical and communicative coupling with a smart watch. Such coupling may be achieved with the use of mating connectors, magnets, Velcro®, or the like. A first head may include one or more sensors and circuitry described herein, and the second head may include one or more sensors of the same or a different type. The head 202 or at least one head if two more heads are included in wearable device 200, may be disposed or designed to be disposed to measure position of an extremity more accurately. Head 202 if disposed on the interior of the wrist and includes a proximity sensor may be more suitable to measure flexion than if disposed on the exterior of the wrist. In some implementations, a plurality of proximity sensors are spaced a part on band (collectively 204A and 204B). In some implementations, a plurality of proximity sensors are spaced evenly apart along a portion or portions of the band (collectively 204A and 204B) or all around the band (collectively 204A and 204B). One or more proximity sensors in the plurality of proximity sensors may be at the distal side of band (collectively 204A and 204B) to have a better view of any distal extremity.

In some implementations band (collectively 204A and 204B) includes a first part of band 204A and a second part 204B. Band (collectively 204A and 204B) may include a flexible material which complies when bent around part of a body (e.g., a wrist five to nine inches in circumference) and a hardness which transmits force with immaterial (e.g., minimal, measurable) attenuation or loss. For example, device 200 may include a material having a Shore hardness sufficient to transmit force. In some implementations, band (collectively 204A and 204B) includes a material with Shore Hardness between about 40 to about 80 on the Shore A scale.

The band (collectively 204A and 204B) may include a thermoplastic like Acrylonitrile Butadiene Styrene (ABS) or nylon. The band (collectively 204A and 204B) may include thermoset material like silicone. In some implementations, the band includes Thermoplastic Elastomer (TPE) such as a Thermoplastic Olefin (TPO) or Thermoplastic Urethane (TPU).

The first part of band 204A may have a different length to the second part of band 204B. The band (collectively 204A and 204B) defines an interior surface 206. The interior surface 206 defines an opening, passage, or void 208 to receive a part of a human body, e.g., the forearm. It should be noted that void 208 may be provided in different shapes and sizes depending upon the user and target limb. Further, void 208 may be customizable by way of 3D printing or casting so as to ensure conformance to the target limb. The second part of band 204B, interior surface 206, and void 208 defines a c-shaped and semi-rigid opening that allows a user to don the wearable device 200 with one hand, and with minimal effort. The semi-rigid second part of band 204B allows the user to hook the device 200 on a limb (e.g., forearm at wrist). The first part of band 204A may include a first part of a fastener, e.g., material including loops of VELCRO®, frame and prong of a buckle, or magnet. The second part of band 204B may include a second part of a fastener, e.g., material including hooks of VELCRO®, defined holes or apertures for the prong of the buckle, or ferromagnetic metal. The user may fasten device 200 to a limb via the fastener.

Wearable device 200 includes a plurality of force sensors 210. The plurality of force sensors 210 may be disposed on or in the band (collectively 204A and 204B). For example, the plurality of force sensors 210 are disposed proximate (e.g., shy, or proud) to interior surface 206. In some implementations, the plurality of force sensors 210 have a spatial extent. Plurality of force sensors 210 may be enumerated 210-1, 210-2, . . . , 210-N-1, 210-N. Plurality of force sensors 210 may include one or more sets of sensors. A first set of force sensors included in the plurality of force sensors 210 may be disposed in or on the first part of band 204A; and a second set of force sensors in or on the second part of band 204B. A first set of force sensors may have a first sensitivity; and a second set of force sensors may have a second sensitivity.

Wearable device 200 includes a frame 212 which may overlie, underlie, encapsulate, extends cooperatively with, be bonded to, or be physically coupled to the device 200. In some implementations, the band (collectively 204A and 204B) includes the frame 212. The second part of the band 204B may include the frame. Frame 212 may be a semi-rigid (e.g., stiff, resilient) body that provides a reference position for a force sensor. The semi-rigid body may also be formed to provide support to the subject-user, for example, for correcting posture or reducing pressure on the limb to assist with the recovery from, or prevention of, repetitive strain injuries, tendinopathies and other musculoskeletal symptoms and injuries. In some instances, the semi-rigid body may also be customized to the unique needs of an individual subject-user and fabricated using 3-D printing or casting. Some or all of the plurality of force sensors 210 may underlie frame 212. That is, underlie the interior surface (side of void 208) of frame 212. Herein, as a default, inward toward the body of a user is associated with the down direction and outward from the body of a user is associated with the up direction, thought in some contexts or express statements this convention will alter. Frame 212 may include one or more materials that are semi-rigid, such as, metal (e.g., steel) or plastic (e.g., polycarbonate, Acrylonitrile Butadiene Styrene (ABS)). Also, in some implementations frame 212 is made of a material that is firm, but still flexible so as to enable gripping onto a user's limb. Examples of such materials include metal tape formed as a bistable prestressed shell or spring, like what is used to form a tape measurer.

Figures 2C, 2D:
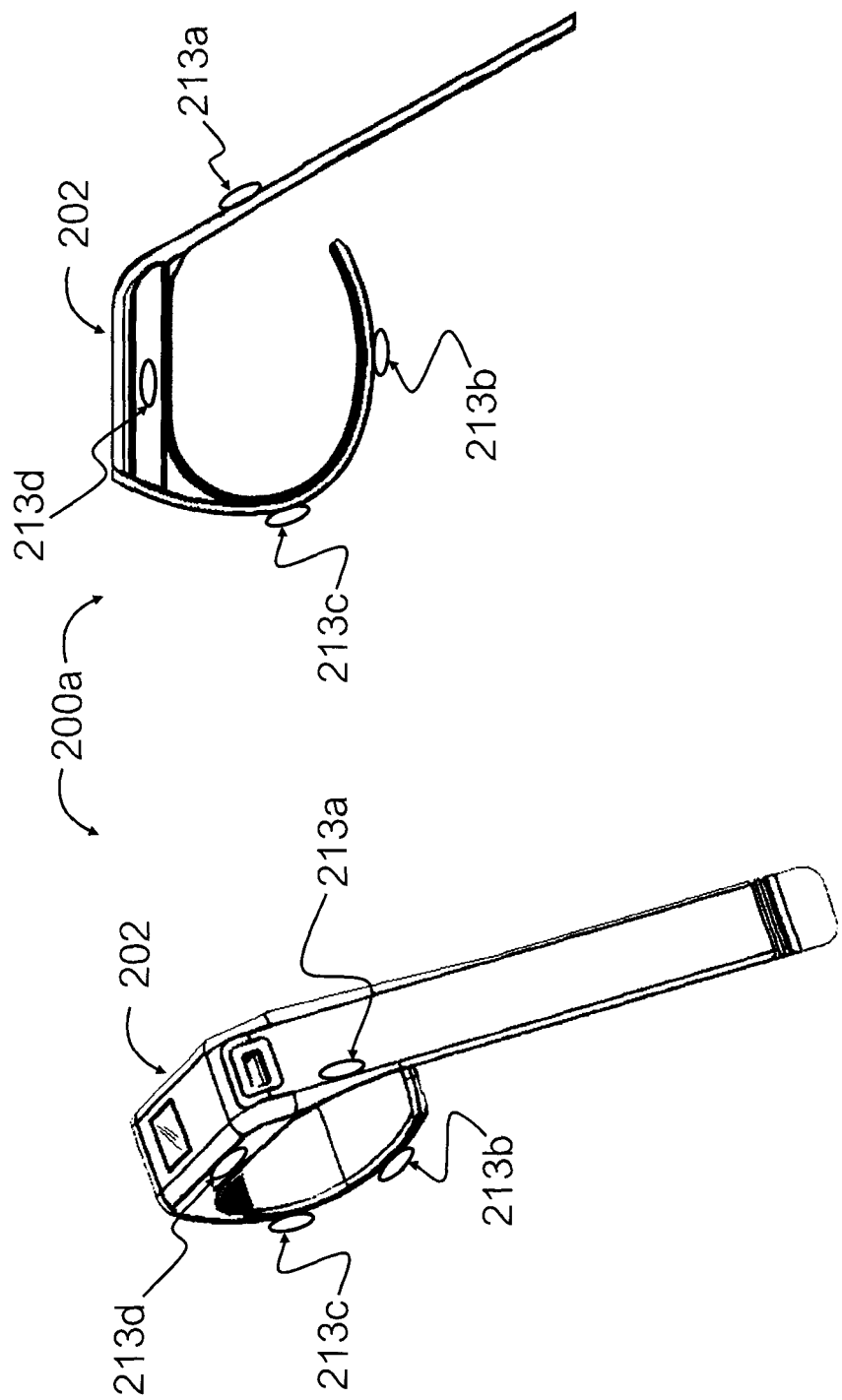
FIG. 2C is a perspective view illustrating another exemplary wearable device as an example of a peripheral device shown in FIG. 1.
FIG. 2D is an elevation view illustrating the exemplary peripheral device shown in FIG. 2C.

FIGS. 2C and 2D are substantially similar to FIGS. 2A and 2B except that the wearable device 200a shown additionally includes four proximity sensors 213a, 213b, 213c, and 213d each located on an extreme edge of the band relatively equidistant from one another. While four sensors are shown, it should be understood that more or less than four are possible. In other configurations, two sensors may be placed on top and two on bottom, but oriented in a manner to be able to track radial and ulnar deviation as well in addition to flexion and extension. While sensors 213a, 213b, 213c, and 213d may be used to provide a true indicator of proximity of the hand when wearable device 200a is placed on a wrist, susceptibility to confounding factors, such as some other object coming in to proximity with the band, is possible. In such instance, FMG may be used as a secondary signal to disambiguate the primary signal coming from the proximity sensors 213a, 213b, 213c, and 213d. It should be noted that strategically placed proximity sensors may also detect the opening/closing of the hand, and the movement of the thumb, or other digits.

FIG. 3A is a schematic diagram illustrating a part of a human body including a hand 302 and a forearm 304. The hand 302 is joined to the forearm 304 by a wrist 306 which while often characterized as one joint includes a plurality of joints disposed around and between bones in the forearm (i.e., radius and ulna) and hand (i.e., carpels). The wrist 306 includes a plurality of muscles and tendons. Wrist 306 is capable of, at least, three movements: flexion and extension; supination and pronation; ulnar deviation and radial deviation. Pose, or change in pose, of wrist 306 may be quantified angle of the wrist with respect to fore arm. Occurrence of a change in pose may be done via classification of angle above a threshold. Hand 302 and forearm 304 are illustrated in a plurality of poses in FIG. 3A, FIG. 3B, and so on. Some poses are illustrated with stippled lines but the part of a human body, e.g., hand 302 and forearm 304 are not called out to avoid cluttering the drawing. Some poses for hand 302, forearm 304, and wrist 306 are shown in two figures. In some implementations, supination and pronation are associated with forearm 304.

FIG. 3A schematically illustrates flexion 308 and extension 310. Flexion 308 describes motion of the palm of hand 302, a left hand, towards the forearm 304. Extension 310 describes motion of back of hand 302 towards forearm 304.

FIG. 3B illustrates motions of supination 312 and pronation 314. Supination 312 describes rotating the forearm 304 in the direction consistent with from a palm down to a palm up position, i.e., clockwise if viewed from proximal side of wrist. Pronation 314, describes rotation of the forearm in the direction consistent with a palm up to down, i.e., counterclockwise.

FIG. 3C illustrates ulnar deviation and radial deviation, also known as, ulnar flexion and radial flexion. Motion 316 shows ulnar deviation or a bend of the wrist to side of the little finger and ulnar bone. Motion 318 shows radial deviation, a bend of the wrist to side of the thumb and radial bone.

FIGS. 3D and 3E illustrate hand 302 at rest and as a fist, respectively. In FIG. 3D, pose 320 shows an initial position of hand 302 and in FIG. 3E pose 322 shows hand 302 in a fist. The coordinated movement to make a fist involves a number of muscles that operate in combination or sequence. When hand 302 transitions from pose 320 to pose 322, or the reverse a change in the volume of wrist 304 occurs.

The above described motions may be performed in combination. For example, a hand and forearm may begin a neutral point with the forearm outstretched and palm down. The user may supinate per motion 312 to palm facing sideways. Herein, said forearm and hand (e.g., forearm 304 and hand 302) are described as being in the side pose. The user may then do flexion 308 or extension 310 motions. One or more poses or changes in pose are considered a gesture, and with respect to a hand sometimes known as a grasp type. A pose of a hand may be quantified by the degree to codify different gestures, for example, hand is 75% open, fully opened, or 0% opened, i.e., a fist. Even if one exerts no additional force, the act of opening or closing the hand changes the FMG signal which may therefore be detected. The act of opening or closing the hand also can change the proximity signal which may therefore be detected. In some instances, a pose of a hand may be quantified by grip force exerted by the hand, which would affect the FMG signal which may therefore be detected.

Detecting grasp types may be determined by looking at a combination of the FMG, proximity, IMU, and environmental signals. Depending on the situation, the primary signal may be FMG, IMU, or proximity, with the remaining being secondary signals. Proximity may be the primary signal in cases where cameras or multiple IR proximity sensors are used, in which case each individual digit of the hand may be tracked separately. Tracking the degree or relative amount associated with a gesture would involve monitoring the same signals but additionally deciding what the minimums and maximums ranges for the gesture are.

As an exemplary case of tracking degree of completion, the present invention may monitor the hand to detect a 0 to 100% range of hand fully closed to hand fully opened. Initial calibration of the FMG and proximity signals for the 0% and then 100% range would be accomplished with subsequent mapping of the difference between those signals across the range. Any ambiguities would need to be removed which may include those such as: the wrist moving into flexion, extension, or radial/ulnar deviation as the signals would change; the forearm moving into pronation, supination as the signals would change; the translational movement of the arm and/or body as the signals would change; and drift in the sensors. The latter ambiguity may be handled by performing recalibration based on the context of use—e.g., if the present invention is used as part of game-play, the game-play would indicate when certain gestures or positions have been achieved, so that the calibration may be reset.

Although examples of the disclosure, including here at FIGS. 3A through 3E, are primarily with respect to a device attached to a human user's forearm and may primarily illustrate motions of the user's complete forearm and wrist. However, it should be readily apparent that device may be used by an amputee (missing by accident, surgery, or congenital, one or more members, such as, finger, hand, wrist, forearm), or on and for different body parts, for example, ankle, foot, or knee. The device may be used by a non-human natural being or robotic being.

FIG. 4A and FIG. 4B are schematic diagrams illustrating a pose for a human forearm relative to body of human 400. In FIG. 4A, human 400 includes an arm including a forearm 304. Forearm 304 is outstretched and described relative to axis 402 parallel to floor and parallel to sagittal or parasagittal planes (see FIG. 4B). Human 400 may wear (e.g., physically coupled and upon) on wrist 304 a wearable device, such as, wearable device 200.

Forearm 304 may be in a predetermined range of poses. An example of a predetermined range of poses includes poses like those shown in FIG. 4A and FIG. 4B, that is, forearm 304 outstretched. In some implementations, the predetermined range of poses includes forearm 304 parallel to axis 402. The forearm 304 may be in the predetermined range of poses when not parallel to axis 402. In some implementations, forearm 304 is in the predetermined range of poses when forearm 304 pitches up and down (i.e., displaced by motion 404) by up to 15 degrees relative to axis 402. In some implementations, the forearm 304 is in the predetermined range of poses where forearm 304 is held at an angle within 30 degrees of up or down pitch.

In some implementations, forearm 304 is in the predetermined range of poses when in a static pose abducted by up to 90 degrees relative to axis 402. That is, brought closer to body along motion 406. In some implementations, forearm 304 is in the predetermined range of poses when adducted by up to 45 degrees relative to axis 402.

Figures 5A, 5B:
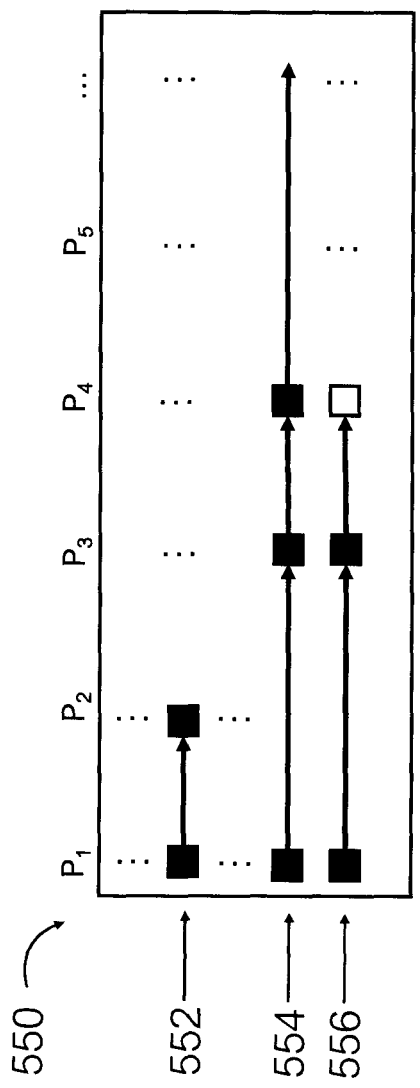
FIG. 5A is a schematic diagram illustrating gestures against force sensor data and proximity sensor data given a limb pose.
FIG. 5B is a schematic diagram illustrating gestures against limb pose given at least force sensor data.

FIG. 5A includes a table 500 for a given pose, such as, shown and described in FIGS. 4A and 4B. Table 500 includes a header row 502 comprising a plurality force sensor labels, e.g., $FS_1$, $FS_2$, . . . $FS_N$. The plurality of force sensor labels may be associated with a plurality of force sensors that are spatially distributed. Table 500 may be used in the spatial analysis of force values. A plurality of force sensor values may be associated with the plurality of force sensor labels in header row 502. For example, rows 504 through 510 include a plurality of force sensor values that show increase (+) in force, no change (0), and decrease (−) in force to a previous value (e.g., value of previous time step) or aggregate value (e.g., average). Header row 502 may further include one or more proximity sensor labels, e.g., $PS_1$. A plurality of proximity sensor values may be associated with the one or more proximity sensor labels in header row 502. Example sensor values include below low threshold (bt), in range (numeric value), above upper threshold (aT), null value (NaN), and not relevant. The sensor values may be numeric values.

A processor may use table 500 to select a gesture, such as, gestures shown in table 500 under a label gesture in header row 502. A processor may use data received from force sensors (e.g., force sensor values) to select a gesture. Some rows of table 500 have a unique gesture associated with a unique set of force values. See, for example, row 504 or row 510. Some rows of table 500 have two or more gestures associated with a unique set of force values. See, for example, row 506 and row 508. A processor may use proximity sensor values to select a gesture. Selection of gestures is described herein, at least, in relation to FIG. 6, FIGS. 9A through 9C, et seq.

FIG. 5B is a schematic diagram illustrating gesture against pose given at least force sensor data. A user wearing a wearable device may assume a gesture that creates force myographic data and then assume one or more poses. A processor-based device may select (e.g., ascertain, fix, determine) a pose based on a plurality of inputs. Examples of methods in which a processor may use FIG. 5B are shown and described in relation to, at least, FIG. 13 and FIG. 14.

A processor-based device may generate gesture information from limb pose data if extremity pose information represents the user's extremity is in a second acceptable range of extremity poses. Table 550 includes rows that corresponds to extremity poses in the second acceptable range of extremity poses. The second acceptable range of extremity poses may include a plurality of discreet poses.

FIG. 5B includes a table 550 which allows a wearable device to select gesture, given a user starts in a predefined extremity pose that creates force myographic data. The predefined extremity pose may include those shown and described in FIGS. 3A through 3E. Table 550 includes a plurality poses, e.g., $P_1$, $P_2$, ... $P_N$. A user may adopt a gesture for an extremity including one shown in FIGS. 3A through 3E. The user may then move their limb to a variety of poses such as, neutral pose shown by FIGS. 4A and 4B; arm raise (e.g., one-handed fist salute); arm at side (e.g., mountain pose in yoga) . . . etc. One or more poses may be recognized as an input value. As well, one or more poses may be associated with a command. Row 552 includes a transition from a first pose to a second pose. Row 554 shows a transition from the first pose $P_1$ to a third pose $P_3$ to a fourth pose $P_4$ and so on (not explicitly illustrated). Row 556 shows a transition from the first pose $P_1$ to a third pose $P_3$ with an optional transition to a fourth pose $P_4$ and so on (not explicitly illustrated).

A variety of methods of monitoring and analyzing a body part including extremities of a subject-user will now be discussed.

Figure 6:
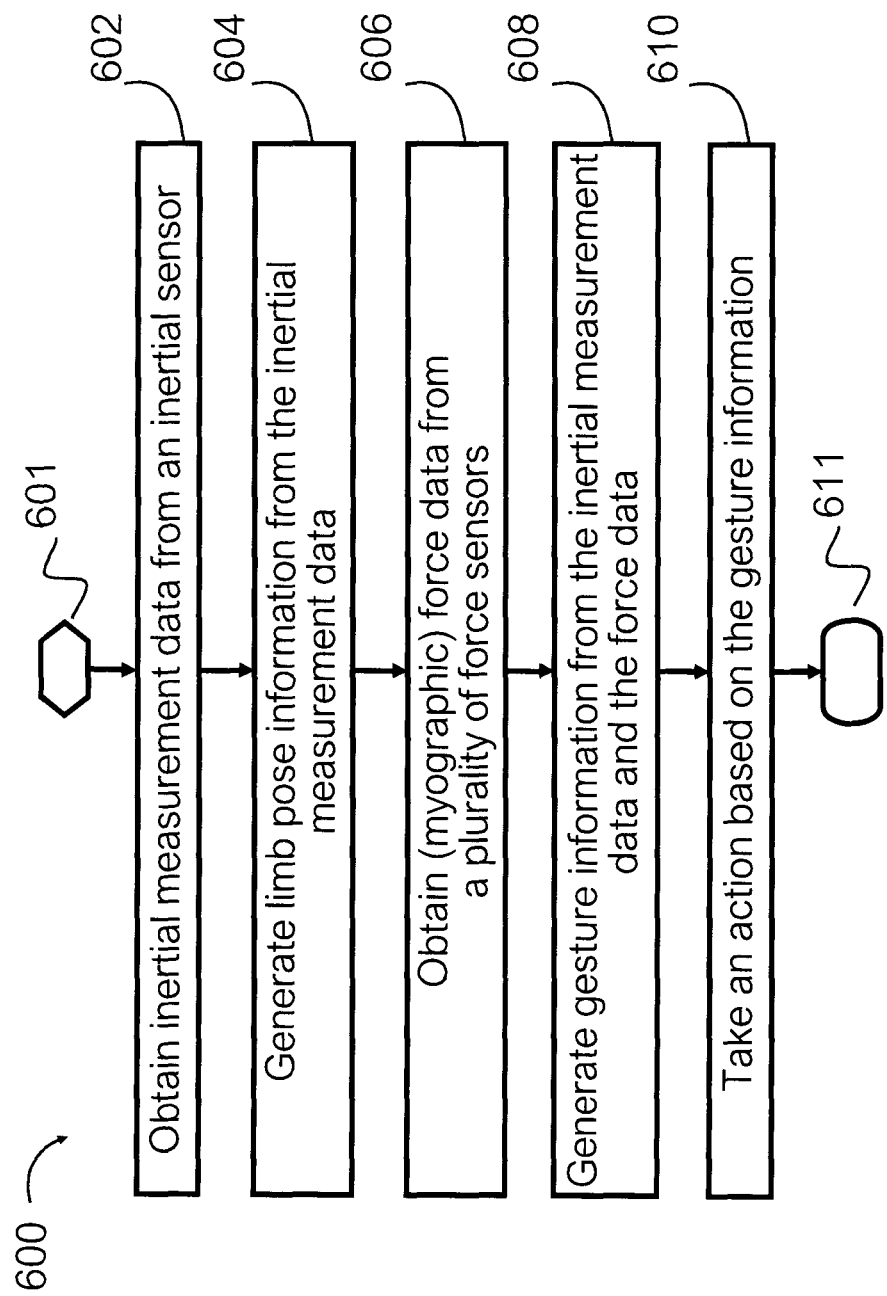
FIG. 6 is a flow-diagram illustrating an example inventive method related to the apparatus shown in FIGS. 1 and 2.

FIG. 6 illustrates an example method 600 (including, for example, acts 602, 604, etc.) of operation for a wearable device, such as, peripheral device 150, or wearable device 200. For method 600, as with other methods taught herein, the various acts may be performed in a different order than that illustrated and described. As well, the acts may be performed in parallel or overlapping sequential operation by different circuitry, e.g., parallel processors. Additionally, the methods may omit some acts, and/or employ additional acts. One or more acts of method 600 may be performed by or via one or more circuits, for instance, one or more hardware processors. In some implementations, method 600 is performed by a controller, e.g., control subsystem 104 of apparatus 100, controller 156 of peripheral device 150.

Method 600 may begin at 601 by invocation from a controller. At 602, the controller receives inertial measurement data from one or more inertial sensors. For example, the controller receives processor-readable data from inertial sensor 158 that represents pose of a user's limb. For example, the inertial measurement data includes forearm pose information which represents a pose of a forearm of a user. At 604, the controller generates limb pose information from the inertial measurement data. For example, the controller, at 604, may convert a gravity vector into forearm pose information. It should further be understood that the forearm angle may be estimated using the gravity vector from an accelerometer provided in the band or, alternatively, may be measured using an attitude and heading reference system (AHRS). An AHRS consists of sensors on three axis that provide attitude information for roll, pitch, and yaw.

At 606, the controller, obtains (e.g., accesses, gets, receives) force data from the plurality of force sensors. The force data is processor-readable data that represents myographic information. In some implementations, the force data is processor-readable information that includes a plurality of force values. The force values may correspond to forces exerted by a part of a user's body against a reference body (e.g., frame 212, band (collectively 204A and 204B), web 1600 of FIG. 16A). In some implementations, the force data represents volumetric properties for the limb near to where a user wears a wearable device.

In some implementations, the force data are processor-readable information that includes a plurality of force values. The plurality of force values may be values for one time or a series of values over a period. The controller may, at 606, detect if a change occurs in the force values over time. Further examples of temporal analysis of force data is described herein, at least, in relation to FIG. 12A.

At 608, the controller generates gesture information from the force data and the inertial measurement data. The controller at 608 may execute one or more sets of processor-executable instructions, such as, inertial measurement instructions 128, force measurement instructions 130, and pose identification instructions 134. The controller may generate the gesture information if the inertial data shows a limb is in a predefined range of limb poses. For example, see, at least, FIGS. 5A, 8, and 10 to 12A and 12B. The controller may generate the gesture information if the force data shows the extremity is in a predefined range of extremity poses. For example, see, at least, FIG. 5B and FIG. 13.

At 608, the controller may generate extremity pose information from the force data. At 608, the controller may generate gesture information from a first set of information including the force data or the extremity pose information; and a second set of information including the inertial measurement data, or the limb pose information.

At 610, the controller takes an action, or causes and action to be taken, based on the gesture information. The controller may send a command to a processor-based device, update a processor-readable storage device, or another physical or tangible act. Examples of a controller actions are described herein, at least, in relation to FIG. 14.

At 611, method 600 ends until invoked again. In some implementations, method 600 repeats until termination. Further examples of methods of operation are shown and described herein in relation to, at least, FIGS. 7 through 14. Acts shown and described in method 600, or another method, may be included in other methods with appropriate changes unless the context dictates otherwise.

Figure 7:
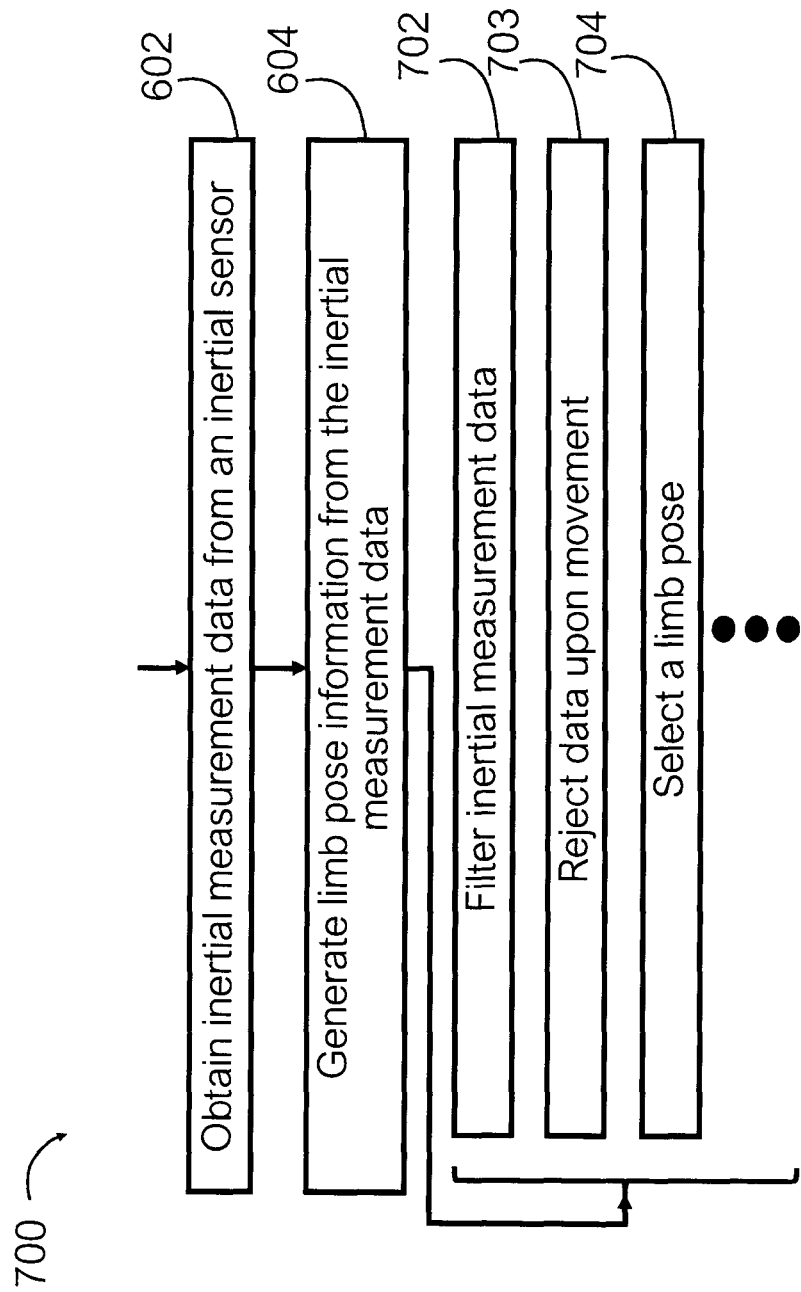

FIG. 7 is a flow diagram illustrating method 700 which includes one or more acts that may be included in act 602 or act 604. Method 700 may include one or more of act 702, act 703, or act 704 as part of act 602 or act 604. At 602, the controller receives inertial measurement data from one or more inertial sensors. At 604, the controller generates limb pose information from the inertial measurement data.

At 702, the controller filters the inertial measurement data. For example, the controller applies a low pass filter to inertial measurement data as part of act 604. In some implementations, the inertial measurement data includes output from an accelerometer on three axes. Each axis described may be sampled at time t and the inertial measurement data may be denoted as a vector:

$$A(t)=\{a_x(t),a_y(t),a_z(t)\} \quad (1)$$

The inertial measurement data may be filtered by a low pass filter:

$$B(t)=LP(A(t)) \quad (2)$$

The low pass filter may be described mathematically as:

$$LP(x_n) = \frac{(t_n - t_{n-1})x_n + Sx_{n-1}}{S + (t_n - t_{n-1})} \quad (3)$$

Where, S is the low pass filter strength, a higher value produces increased sluggishness in the change from $t_{n-1}$ to $t_n$. The difference from $t_{n-1}$ to $t_n$ is a sample rate. In some implementations, the sample rate is between 20 Hz and 50 Hz, e.g., 30 Hz or 50 Hz.

At 704, the controller rejects data upon movement. For example, the controller rejects force data upon movement of a forearm. The controller may create a plurality of indication values and reject data associated with motion values above a threshold. The motion indication values may include the product of acceleration data per Eqn. (1) and the time derivative (e.g., first order difference) of the acceleration data. The motion indication values may also include the product of acceleration data and the time derivative of the acceleration data where one or more of the following is applied to the acceleration data or the time derivative of the acceleration data: offset adjustment, low pass filtering, and vector norm.

At 706, the controller selects a limb pose. The controller may select a limb pose via a look up function:

$$\text{Orientation}(B(t)) = \quad (4)$$
$$\begin{cases} \text{unknown, if conditions for flat AND side are false} \\ \text{flat, } 7000 < Norm(B(t)) < 9000 \text{ AND } 7000 < b_z(t) < 9000 \\ \text{side, } 7000 < Norm(B(t)) < 9000 \text{ AND } -9000 < b_y(t) < -7000 \end{cases}$$

Where Norm(X) is a vector norm, such as, Euclidean norm, weighted Euclidean norm, or the like. Flat and side are orientations of a forearm corresponding to pronated and mid-prone.

Figure 8:
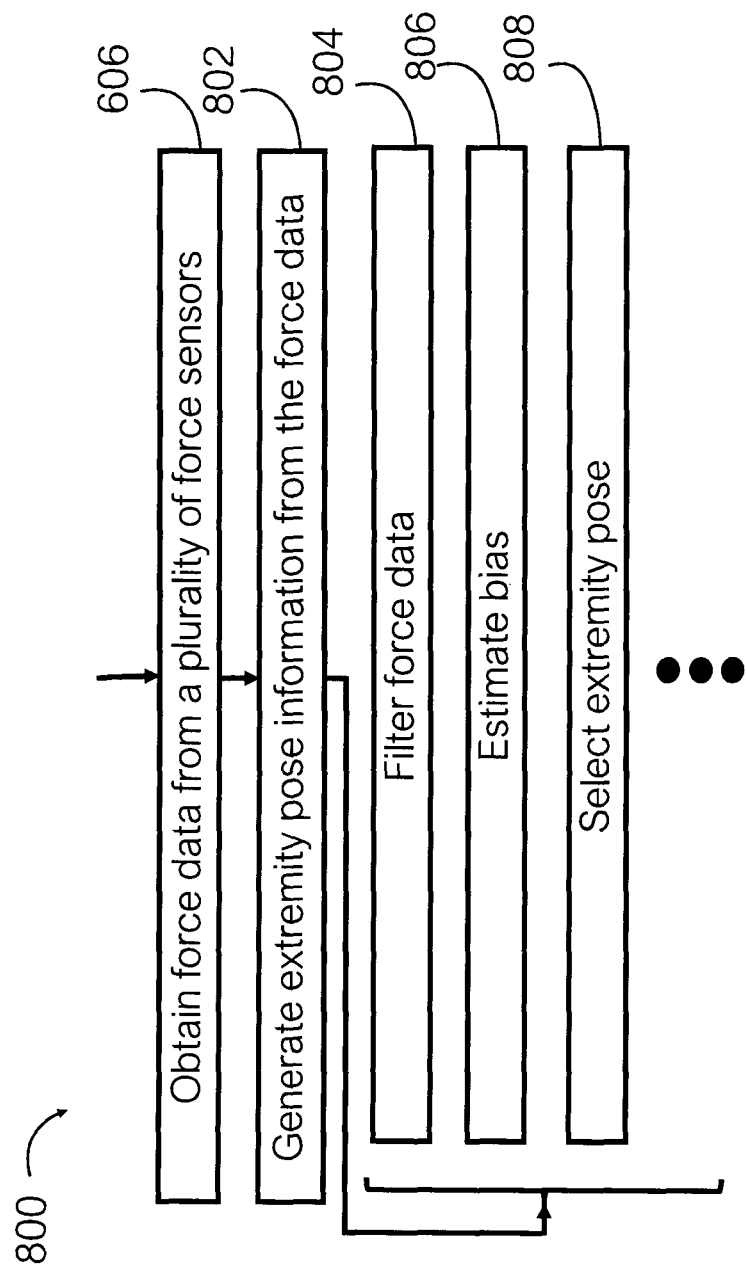

FIG. 8 is a flow diagram illustrating method 800 which includes task that may be included in act 606 or act 608. Method 700 may include act 804, act 806, or act 808 as part of act 606, act 608, or act 802. At 606, the controller receives force data from the plurality of force sensors. At 802, the controller generates extremity pose information from the force data.

At 804, the controller filters the force data. For example, the controller filters the force data received at 606. The force data may be represented as a plurality of force values sampled at time t and may be more particularly represented by a vector F(t) where each component of the vector denotes the individual force at a force sensor, e.g., $$F(t)=\{f_1(t), f_2(t), \ldots, f_n(t)\} \quad (5)$$

The controller may filter the force data F(t) using one or more filters to reduce noise, condition the force data, and the like. For example, the controller may apply a spike filter which in response to being applied removes the spikes resulting from faulty hardware, and a low pass filter that in response to be applied removes inherent noise. For example, $$G(t)=\{g_1(t), g_2(t), \ldots, g_n(t)\} \quad (6)$$

$$G(t)=LP(SF(F_i(t))) \quad (7)$$

The spike filter may be described mathematically as:

$$SF(x_n) = \begin{cases} x_n, & ||x_n - x_{n-1}| < x_0 \\ x_{n-1}, & ||x_n - x_{n-1}| \geq x_0 \end{cases} \quad (8)$$

Where, $x_0$ is a predefined threshold. An examples of a low pass filter is described above at Eqn. (3).

At 804, the controller may filter an aggregate of the force data. The controller may calculate a net pressure value m(t) as an aggregate of the data received from the force sensors at 606. An example of a net pressure value is the root of the mean of the squares of the forces measured on each force sensor. The controller at 804 may filter the net pressure value via a low pass filter such as described above at Eqn. (4).

At 806, the controller may estimate bias in the force data. The controller may estimate bias and remove slowly varying parts of the aggregate force value. The biased aggregated force value may be:

$$m_{bias}(t)=DZ(m(t)-LP(m(t))) \quad (9)$$

Where DZ(x) is a filter such as:

$$DZ(x) = \begin{cases} 0, & x < x_0 \\ x, & x \geq x_0 \end{cases} \quad (10)$$

Where $x_0$ is a threshold.

The controller may remove an initial value from the aggregate force value.

$$m_{IB}(t)=m(t)-m_{offset} \quad (11)$$

Where $m_{offset}$ is an offset value received prior to act 602.

At 808, the controller may select an extremity pose. In some implementations, the gesture is selected based on the bias aggregate force value and the initial value from the aggregate force value. In the wrist band implementation presuming the hand remains static, the controller may select an extremity pose based on three volume values:

$$\text{Volume}(m_{bias}, m_{IB}) = \qquad (12)$$
$$\begin{cases} \text{rest}, & \text{if conditions for high AND low are false} \\ \text{high}, & (m_{bias} > 0.1) \text{ AND } \left(m_{IB} > \frac{\max(m_{IB})}{2}\right) \\ \text{low}, & (m_{bias} < -0.1) \text{ AND } (m_{IB} < \min(m_{IB}) + 10) \end{cases}$$

Where rest is no or little change in volume, high is an increase in volume and corresponds to wrist extension, and low corresponds to wrist flexion. The minimum and maximum values may be a predefined value or dynamically updated. The volume values may be replaced by flexion and extension values.

At 808, the controller may generate extremity pose information. That is processor readable information which represents pose of an extremity more distally disposed to a wearable device. For example, a wrist or set of fingers when the wearable device is on the forearm.

Returning to method 600, at 608 the controller may select a gesture based on, at least, the force data. For example, the controller selects a gesture based on the limb pose described in relation to act 706 and Eqn. (4); and the volume values described in relation to act 808 and Eqn. (12). The controller may select a gesture based on a look up function for a right hand:

$$G(\text{pose, volume}) = \begin{cases} \text{up} \mid \text{pose} = \text{flat \& volume} = \text{high} \\ \text{rest} \mid \text{pose} = \text{flat \& volume} = \text{rest} \\ \text{down} \mid \text{pose} = \text{flat \& volume} = \text{low} \\ \text{right} \mid \text{pose} = \text{side \& volume} = \text{high} \\ \text{rest} \mid \text{pose} = \text{side \& volume} = \text{rest} \\ \text{left} \mid \text{pose} = \text{side \& volume} = \text{low} \end{cases} \qquad (13)$$

The gesture may include flat rest—wrist is straight, hand is open, palm of hand is parallel to the ground; side rest—wrist is straight, hand is open, palm of hand is perpendicular to the ground; up—wrist is extended, hand is open, wrist is in "flat" orientation; down—wrist is flexed, hand is open, wrist is in "flat" orientation; right (or side up or left)—wrist is extended, hand is open, wrist is in "side" orientation; and left (or side down or right)—wrist is flexed, hand is open, wrist is in "side" orientation. The labels left and right interchange with the location of the wearable device but labels side up and side down do not. A user may wear more than one wearable device and hence, combinations of gestures between the two or more devices may be used to issue control signals.

Figure 9A:
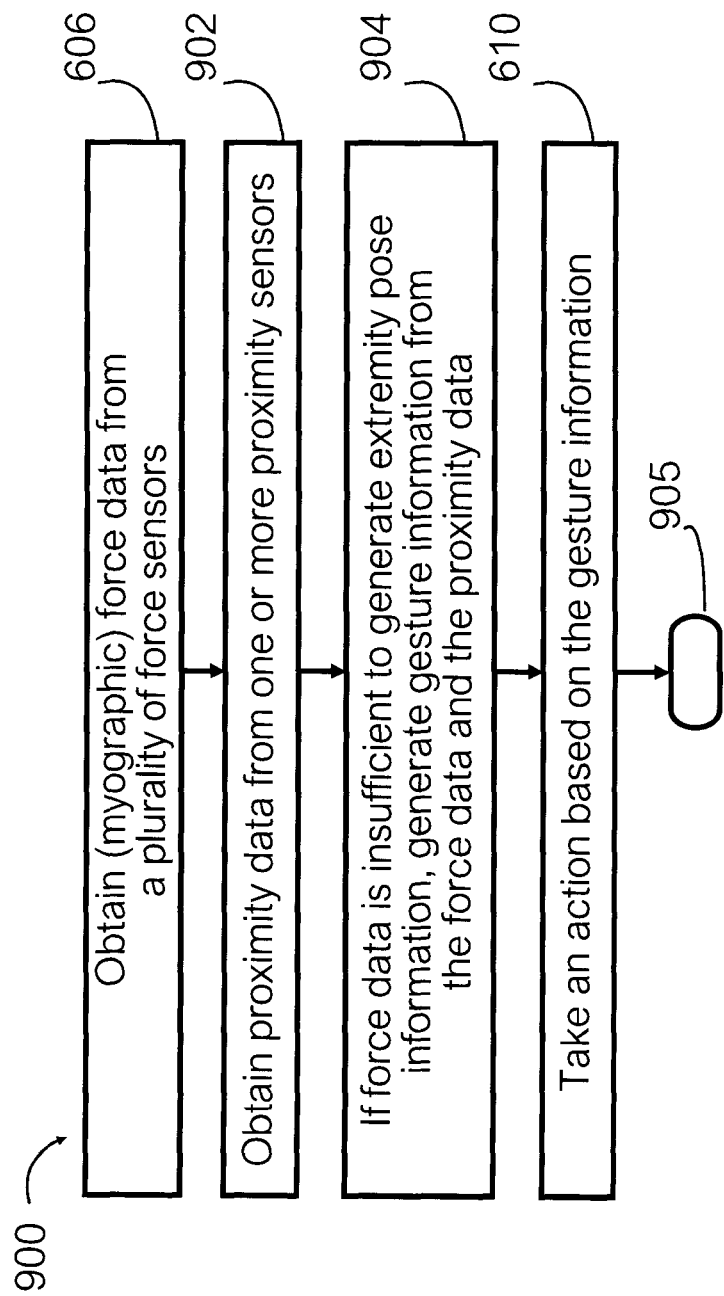

FIG. 9A illustrates method 900 being an example of a method of operation for a wearable device, such as, peripheral device 150, wearable device 200. In method 900, a controller receives proximity data and generates gesture information based, in part, on the proximity data.

Method 900 may begin after invocation by a controller. Method 900 may begin after one or more acts including those described in FIG. 6.

At 802, the controller generates extremity pose information from the force data. At 606, the controller, obtains (e.g., receives) force data from a plurality of force sensors, e.g., obtains data representing myographic information from a limb.

At 902, the controller receives proximity data from one or more proximity sensors. For example, the controller receives processor-readable distance information from a time-of-flight sensor physically coupled to a wearable device. The controller may receive proximity data from one or more capacitors or capacitive sensors. The sensor may be oriented perpendicular to the band and may look in a distal direction toward the hand. The proximity data may be received from a proximity sensor included in a wearable device, e.g., proximity sensor(s) 160 in peripheral device 150. The proximity sensor may be on the outside of the wrist to detect extension, inside of the wrist to detect flexion, or either side depending on the sensor and associated processor-executable instructions.

At 904, if the force data is insufficient to generate extremity pose information, the controller generates extremity pose information from the force data and the proximity data. For example, the controller generates extremity pose information from the force data received at act 606 and the proximity data received at 902. The controller, at 904, may execute proximity measurement instructions 132, and pose identification instructions 134. The proximity measurement instructions 132 may differentiate between rest, flexion, and extension, or in some implementations, between extension and other states. In instances where line-of-sight proximity sensors are used, proximity measurement instructions 132 measure if the line of sight of a proximity sensor is occluded or blocked by the hand. The proximity measurement instructions 132 may apply a threshold function to the proximity data including rejecting distances too close and too far.

At 610, the controller takes an action, or causes and action to be taken, based on the gesture information. Examples of a controller actions are described herein, at least, in relation to FIG. 14.

At 905, method 900 ends until invoked again.

Figure 9B:
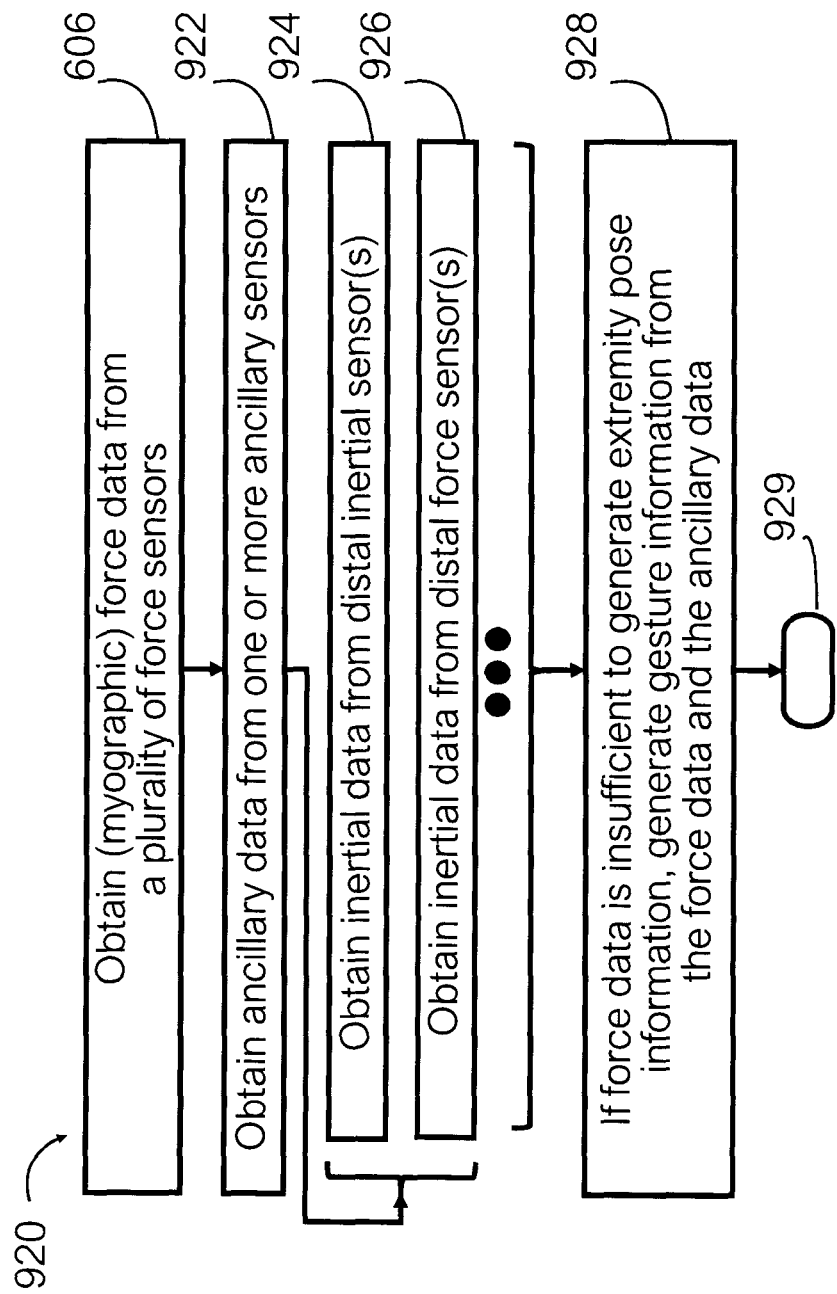

FIG. 9B illustrates method 920 being an example of a method of operation for a wearable device. In method 920, a controller obtains ancillary data and generates gesture information based, in part, on the ancillary data. The ancillary data may include proximity data (c.f., method 900 in FIG. 9A), inertial data from one or more distally disposed sensors, or force data from one or more distally disposed sensors.

Method 920 may begin after invocation by a controller. At 606, the controller, obtains (e.g., receives) force data from a plurality of force sensors.

At 922, the controller obtains ancillary data from one or more ancillary sensors. For example, the controller obtains processor-readable return intensity information from a time-of-flight sensor physically coupled to a wearable device (not explicitly illustrated). Alternatively, or additionally, at 924, the controller obtains inertial data from one or more distally disposed inertial sensors. For example, the user may wear an inertial measurement unit, e.g., inertial sensor 168, on a more distal location such as on his or her hand or finger (e.g., on at distal end of at least one finger). The distally disposed inertial sensors may measure absolute or relative pose of the hand or first phalange of at least one finger. This measurement could be relative to the wrist bands IMU or could be absolute, i.e. relative to the global reference frame.

Alternatively, or additionally, at 926, the controller obtains inertial data from one or more distally disposed force sensors. For example, the user may wear a force sensor on the palmar side of his or her hand, e.g., force sensor 170. The force sensor on the palmar side of hand may measure interaction with an item. The user may wear distally disposed force sensor(s) on the plantar side of foot to measure interaction with ground, e.g., support analysis of gait or balance.

At 928, if the force data is insufficient to generate extremity pose information, the controller generates extremity pose information from the force data and the ancillary data. For example, the controller generates extremity pose information from the force data received at act 606 and the ancillary data received at 922. The controller, at 928, may execute force measurement instructions 130, proximity measurement instructions 132, pose identification instructions 134, or the like. The controller uses the ancillary data to disambiguate the force data.

At 929, method 920 ends until invoked again.

Figure 9C:
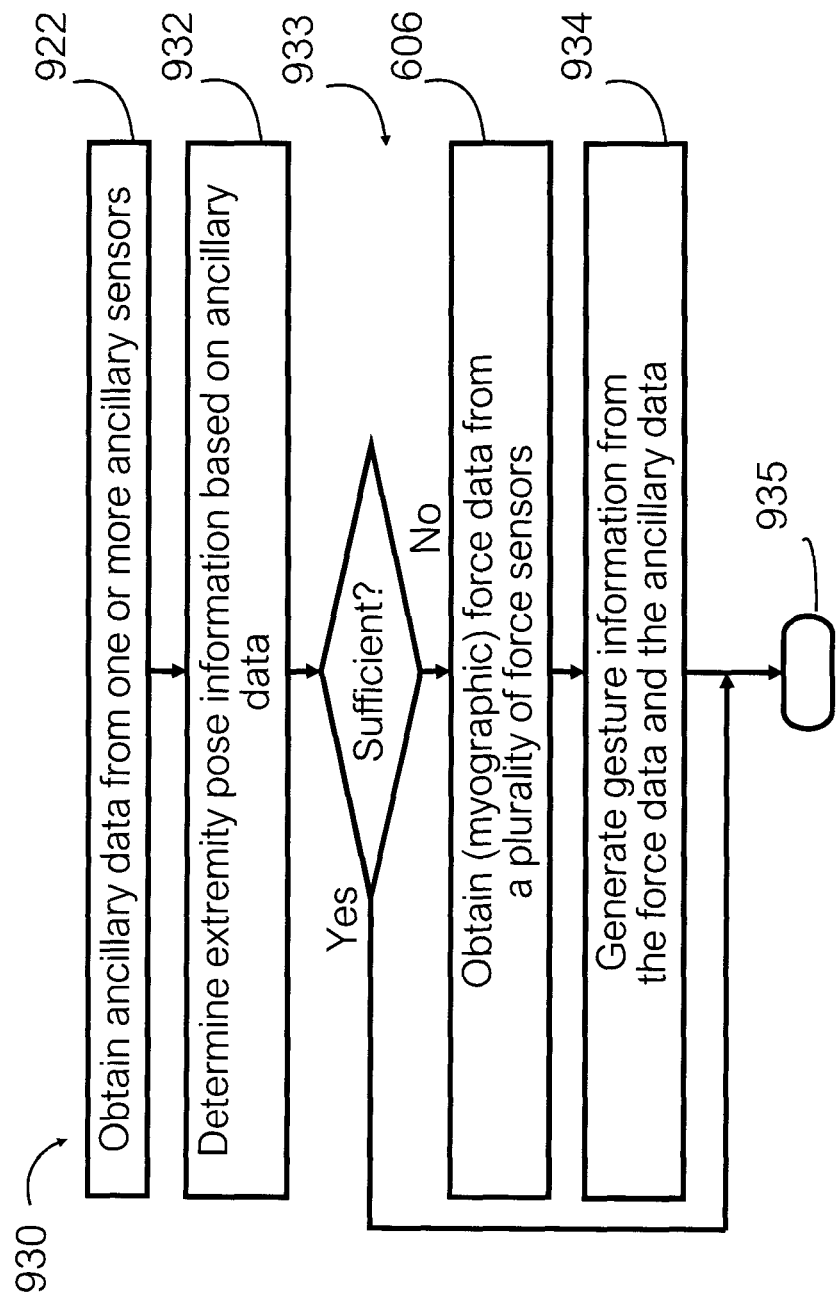

FIG. 9C illustrates method 930 bring an example of a method of operation for a wearable device. In method 930, a controller obtains ancillary data and generates gesture information based, in part, on the ancillary data. In contrast to method 920, the force data is used to disambiguate the ancillary data.

Method 930 may begin after invocation by a controller.

At 922, the controller obtains ancillary data from one or more ancillary sensors.

At 932, the controller determines a pose based on the ancillary data. If the ancillary data is sufficient, e.g., 933-Yes, method 930 may end. If the data is insufficient, e.g., 933-No, processing continues. Though not shown, an alternative condition may be evaluated whereby it would be determined whether sufficient data is present so as to train the device to use just the signals from sensors on the band, or signals from other ancillary sensors.

At 606, the controller, obtains force data from a plurality of force sensors.

At 934, the controller generates extremity pose information from the ancillary data, and the force data. For example, the force data, e.g., myographic force data, is used to disambiguate the ancillary data, e.g., proximity data, inertial data, force data.

At 935, method 930 ends until invoked again.

Figure 10:
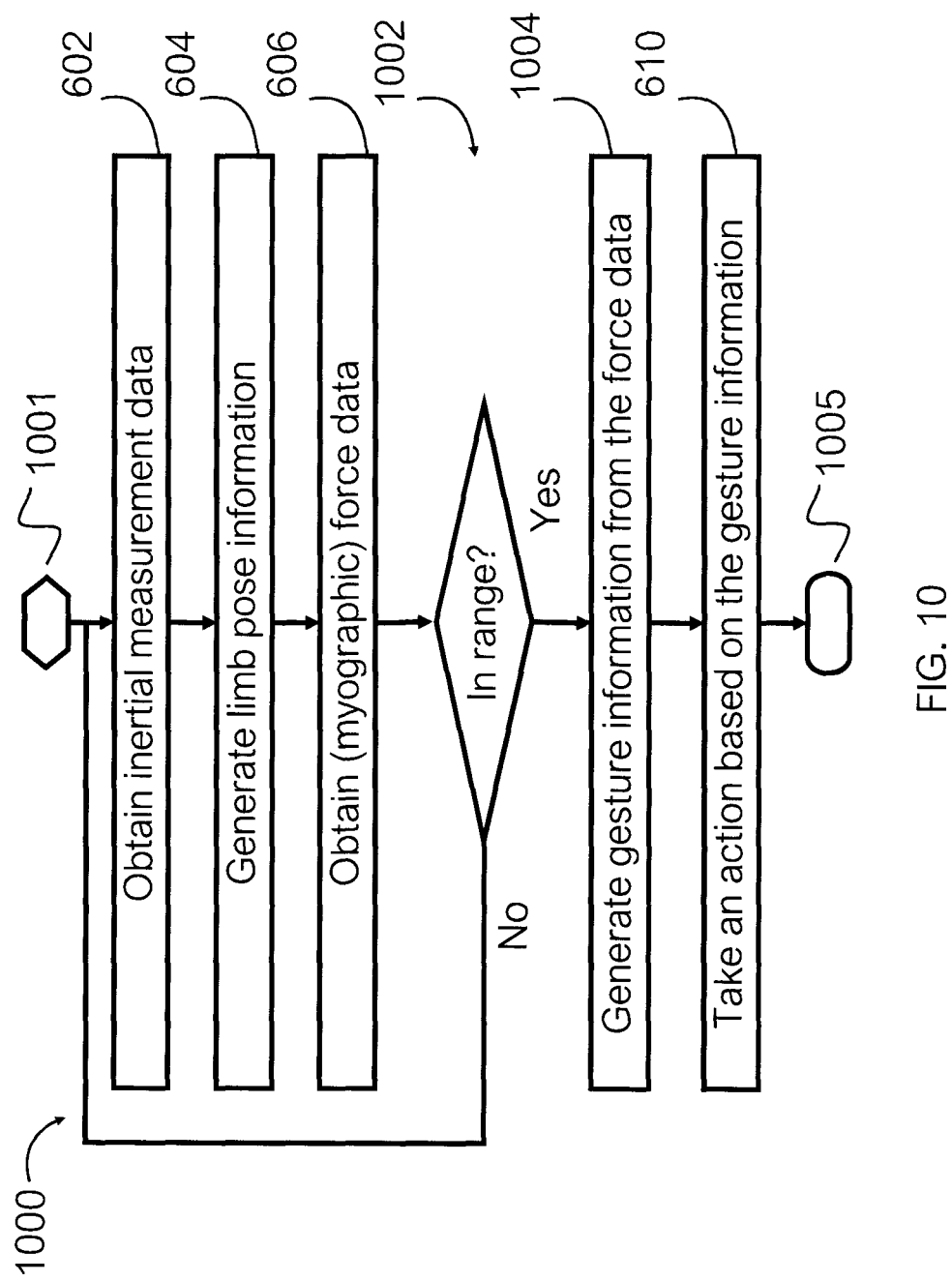

FIG. 10 illustrates method 1000 being an example of a method of operation for a wearable device, such as, peripheral device 150, wearable device 200. In method 1000, a controller generates gesture information from force data received from a wearable device on a user's limb, when a user's limb is within a predetermined range of poses. Examples of predetermined range of poses are shown and described within, at least, FIG. 4A and FIG. 4B.

Method 1000 starts at 1001.

At 602, the controller receives inertial measurement data from one or more inertial sensors. At 604, the controller generates limb pose information from the inertial measurement data. For example, the controller, at 604, may convert a gravity vector into forearm pose information. At 606, the controller receives force data from the plurality of force sensors. The force data is processor-readable data that represents myographic information.

At 1002, the controller checks if the limb associated with the wearable device is within a predetermined range of poses. The predetermined range of poses may include an acceptable range of poses. For example, for an arm the predetermined range of poses may include an arm hanging at rest beside a body, an outstretched arm with a level forearm, and the like. The pose of a limb may be a precondition to classification of myographic data.

If the limb is within a predetermined range of poses, 1002-Yes, then at 1004, the controller generates processor-readable gesture information from the force data. If the limb is not within a predetermined range of poses, 1002-No, then method 1000 continues at 602 in method 1000.

At 610, the controller takes an action, or causes and action to be taken, based on the gesture information. Examples of a controller actions are described herein, at least, in relation to FIG. 14.

At 1005, method 1000 ends.

FIG. 11 illustrates method 1100 being an example of a method of operation for a wearable device, such as, peripheral device 150, wearable device 200. In method 1100, a controller generates gesture information from force data collected from a wearable device on a user's limb. The controller generates gesture information after the controller detects a change in force data and/or when a user's limb is within a predetermined range of poses.

Method 1100 starts at 1101, e.g., after invocation by a controller. Method 1100 may follow one or more acts described herein.

At 602, the controller receives inertial measurement data from an inertial sensor included in a wearable device. At 604, the controller generates limb pose information from the inertial measurement data.

At 1002, the controller checks if the limb associated with (e.g., limb device is affixed to) the wearable device is within a predetermined range of poses. If the limb is not within a predetermined range of poses, 1002-No, then method 1100 continues at 602 after 1101.

If the limb is within a predetermined range of poses, 1002-Yes, then at 606, the controller receives force data from the plurality of force sensors. In some implementations, the controller receives force data from the plurality of force sensors before the controller checks if the limb is within a predetermined range of poses (see, for example, FIG. 10) or before the controller receives inertial measurement data.

At 1102, after the controller has received force data, the controller checks for at least one change (e.g., temporal change) in the force data. For example, the controller may look for a difference in a signal received from one or more sensors, a difference in an aggregate value derived from a plurality of signals, or the like. The difference may be over one period (e.g., time-step) or a plurality of periods (e.g., contiguous samples, non-contiguous samples).

If the controller does not detect at least one change in the force data, 1102-No, then method 1100 continues at 602 after 1101. If the controller detects at least one change in the force data, 1102-Yes, at 1004, the controller generates processor-readable gesture information from the force data.

At 1103, method 1100 ends until invoked again.

Figure 12A:
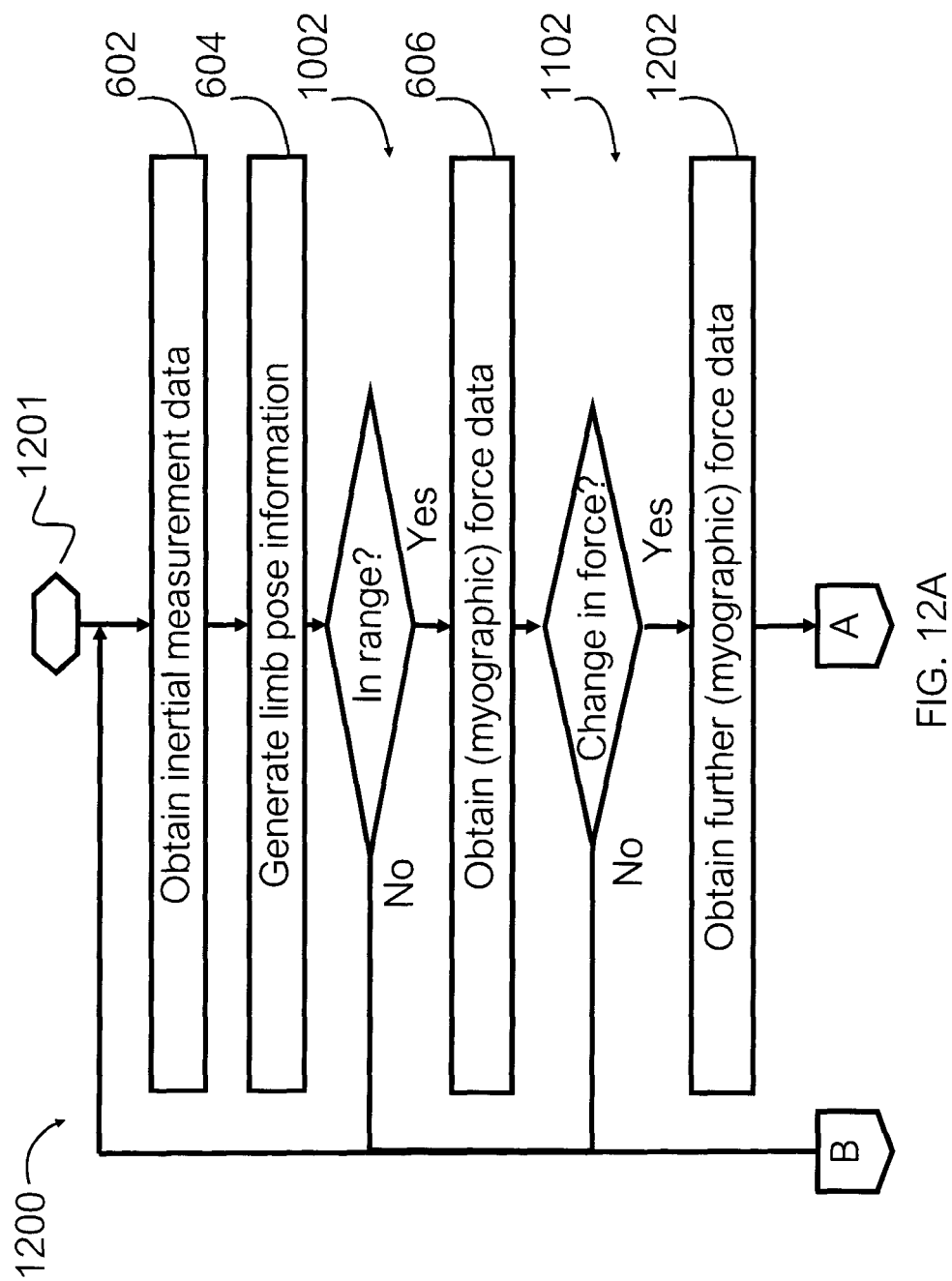
Figure 12B:
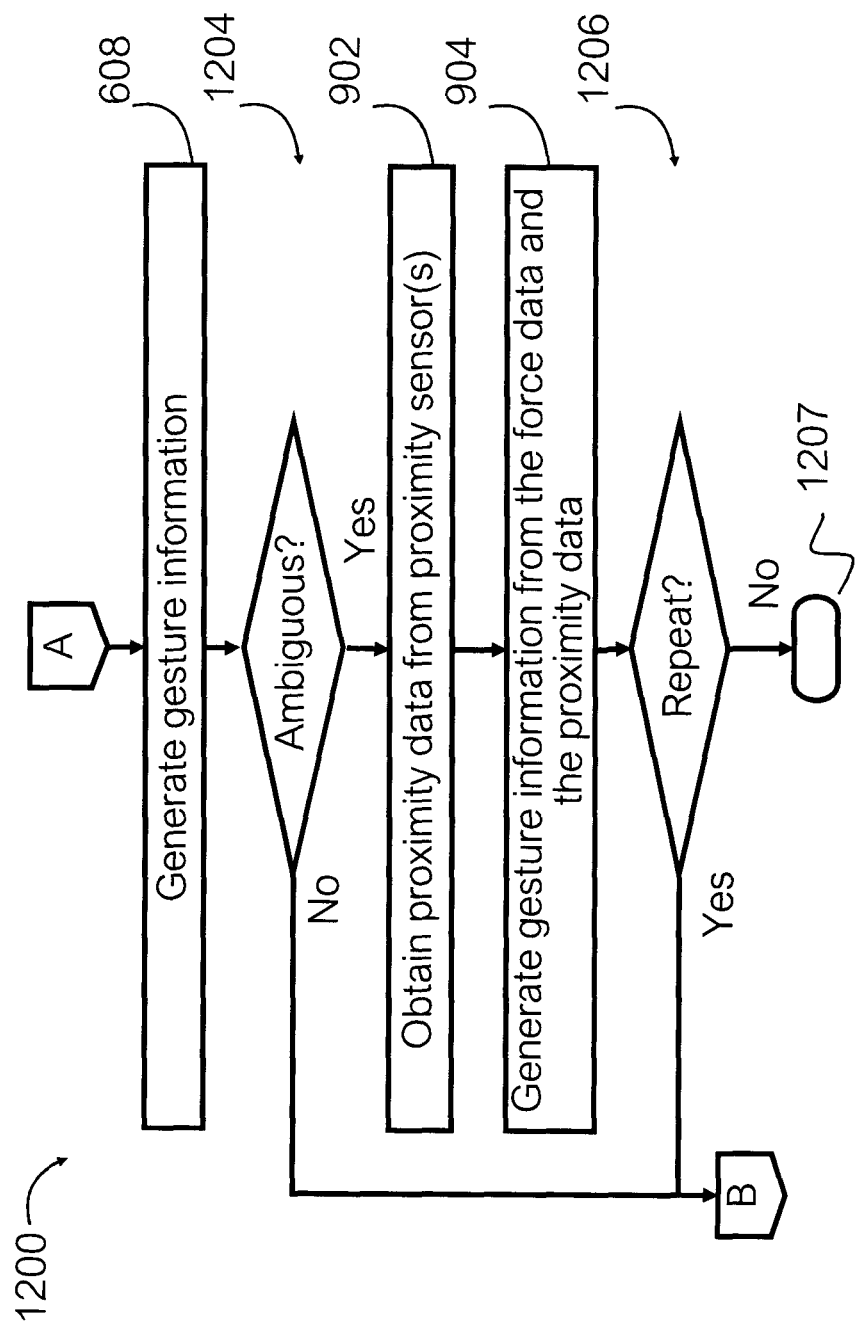

FIGS. 12A and 12B, illustrates method 1200, an example of a method of operation for a wearable device, such as, peripheral device 150, wearable device 200. In method 1200, a controller generates gesture information from force data collected from a wearable device on a user's limb.

Method 1200 starts at 1201, e.g., after invocation by a controller.

At 602, the controller receives inertial measurement data from an inertial sensor included in a wearable device. At 604, the controller generates limb pose information from the inertial measurement data.

At 906, the controller updates a processor-readable storage device with the gesture information. For example, the controller updates the processor-readable storage device with processor-readable information that represents the gesture determined at 904.

At 1002, the controller checks if the limb associated with the wearable device is within a predetermined range of poses. If the limb is not within a predetermined range of poses, 1002-No, then method 1200 continues at 602 after 1201.

If the limb is within a predetermined range of poses, 1002-Yes, then, at 606, the controller receives force data from the plurality of force sensors.

At 1102, after the controller has received force data, the controller checks for at least one change in the force data. If the controller does not detect at least one change in the force data, 1102-No, then method 1200 continues at 602 after 1201. If the controller detects at least one change in the force data, 1102-Yes, at 1202, the controller receives further force data from the plurality of force sensors. The further force data is data associated with a time different from (e.g., after, before) the force data received at 606 in method 1200.

The description of method 1200 continues in relation to FIG. 12B.

In FIG. 12B at 802, the controller generates extremity pose information from the force data received at 606 or 1202. In some implementations, method 1200 includes act 1004 in place of act 802.

At 1204, the controller checks if a gesture may be unambiguously identified from the force data. That is, at 1204, the controller checks if the gesture information is ambiguous. For example, two or more gestures may have a probability above a predetermined threshold. If the gesture information is not ambiguous, 1204-No, then method 1200 continues at 602 after 1201 and may include act 610 prior to act 602 (not explicitly illustrated to avoid crowding FIGS. 12A and 12B).

If the gesture information is ambiguous, 1204-Yes, then at 902, the controller receives proximity data from one or more proximity sensors. At 904, the controller generates gesture information from the force data and the proximity data.

At 1206, the controller checks if method 1200 is to repeat. If the method 1200 is to repeat, 1206-Yes, then method 1200 continues at 602 after 1201 and may include act 610 prior to act 602 (not explicitly illustrated to avoid crowding FIGS. 12A and 12B). If 1206-No, method 1200 terminates at 1207 until invoked again.

Figure 13:
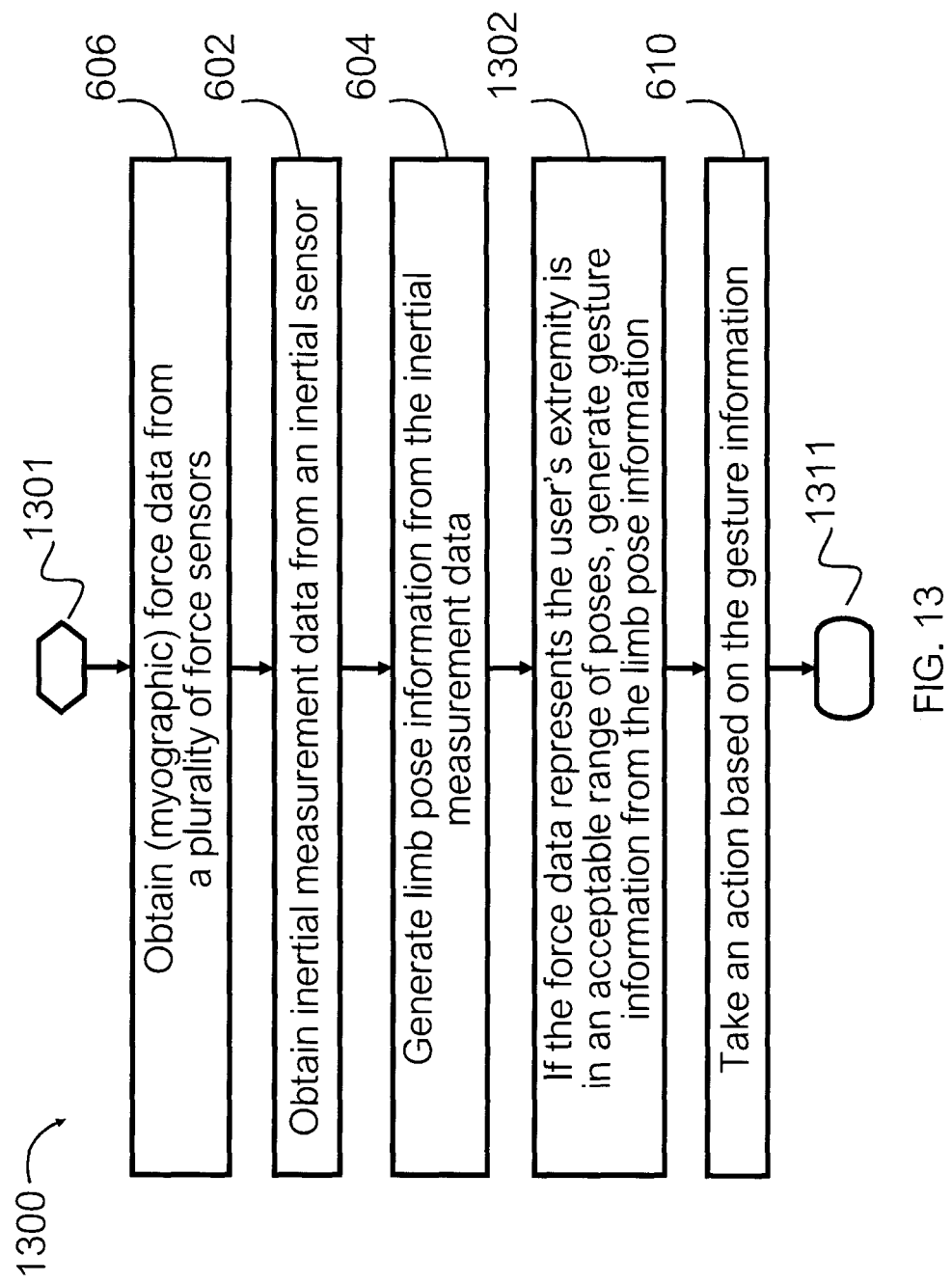

FIG. 13 illustrates method 1300, an example of a method of operation for a wearable device. In method 1300, a controller obtains inertial measurement data and generates gesture information based, in part, on the inertial measurement data.

Method 1300 may (at act 1301) begin after invocation by a controller. Method 1300 may begin after one or more acts including those described in FIG. 6.

At 606, the controller obtains force data from the plurality of force sensors. At 602, the controller obtains inertial measurement data from one or more inertial sensors. At 606, the controller generates limb pose information from the inertial measurement data. For example, the controller invokes one or more acts shown in method 800.

At 1302, if the force data represents the user's extremity is in an acceptable range of poses, the controller generates gesture information from the limb pose information. For example, the controller may wait until the user makes a fist as measured on the force data then track the pose of the limb as a gesture. Further examples of poses of a limb as gestures are described herein at, at least, FIG. 5B. In some implementations, the controller generates gesture information from inertial measurement data.

At 610, the controller takes an action, or causes and action to be taken, based on the gesture information. At 1311, method 1300 ends until invoked again. Examples of a controller actions are described herein, at least, in relation to FIG. 14.

Figure 14:
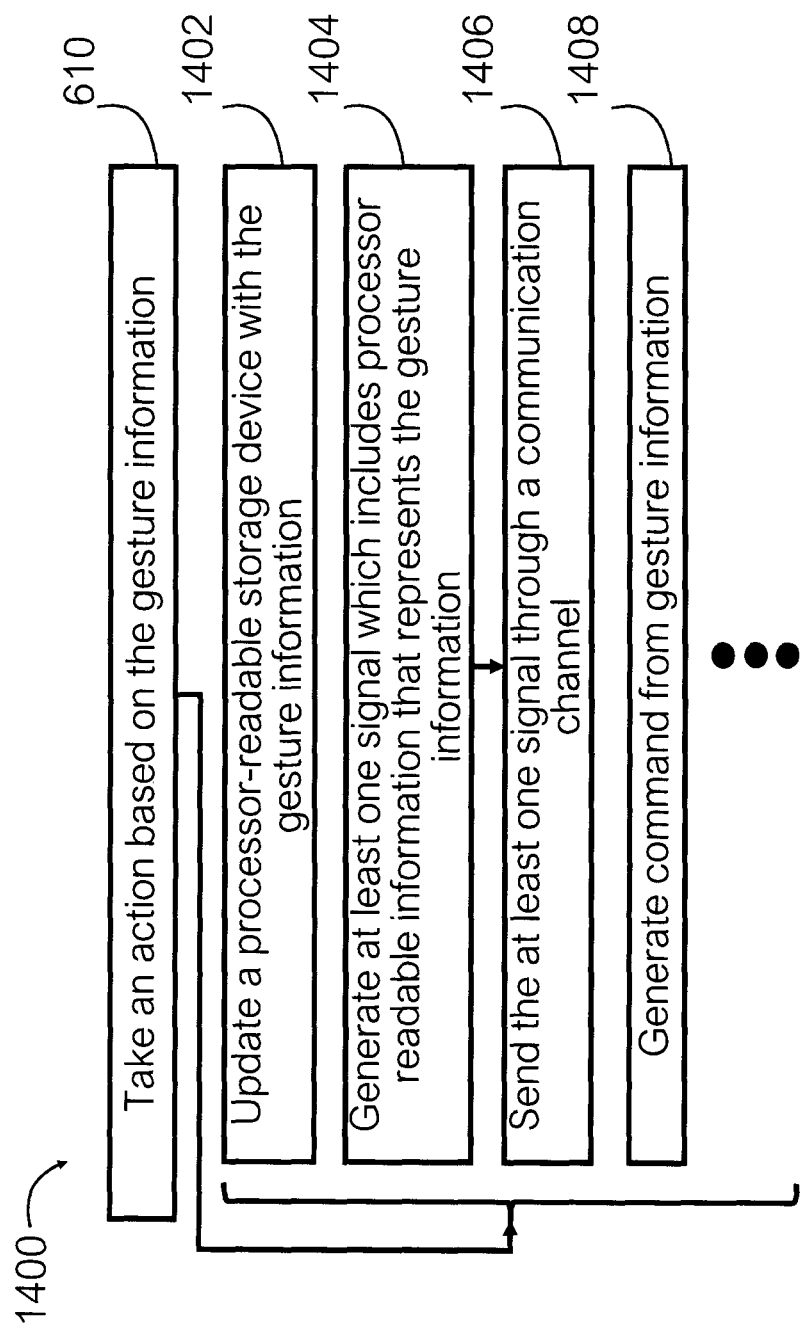

FIG. 14 illustrates method 1400 being an example of acts that may be included in one or more implementations of act 610. The acts shown indented under act 610 are alternatives and two or more such acts, e.g., act 1402, 1404, may occur in the same implementation of act 610.

Method 1400 begins after invocation by a controller. Method 1400 may begin after one or more acts including those described in FIGS. 6, 9A through 9C, 10, 11, 12A, and 12B. Methods 600, 900, 1000, 1100, 1200, and 1300 may include or more instances of acts 610, 1402, 1404, 1406, and 1408.

At 610, the controller takes an action, or causes an action to be taken, based on the gesture information. Exemplary actions are described herein including in act 1402 through 1408 (even numbers, inclusive).

At 1402, the controller updates a processor-readable storage device with gesture information. For example, the processor-readable storage device with one or more sets of gesture information generated in method 900. In some implementations, the controller updates the processor-readable storage device with at least one of inertial measurement data, force data, proximity data, limb pose information, extremity pose information, and gesture information.

At 1404, the controller generates at least one signal which includes processor readable information that represents the gesture information. At 1406, the controller may send, or cause to be sent, the at least one signal through a communication channel, such as, communication channel 148.

At 1408, the controller generates one or more commands from gesture information. The one or more commands are processor-executable instructions. The controller or another processor may execute the one or more commands (not explicitly illustrated). For example, the controller generates a command for a processor-based device from the gesture information generated in method 1100. The wearable device may have a profile as a different user interface device. For example, a profile under a BLUETOOTH LOW ENERGY protocol. As such, a gesture may be mapped, in act 1408, to an input associated with the device profile. For example, a down gesture may be mapped to a button such as down arrow, page down, space, or the like. In some other examples, down gesture may be mapped to commands like lower the volume, slow down, dim the lights, or the like. The controller may generate one or more commands from gesture information where the command includes a variable quantity and the value of the variable quantity is proportional to action of a user, e.g., change in pose. For example, the user may provide a change in poses that he controller uses to lower the volume on a speaker, move a character in virtual world faster, or the like. Further information regarding the quality of the gesture may be derived from the sensors (e.g., force sensors, proximity sensors, inertial sensors). For example, engaging in a simulation like bowling or throwing a dart. The pose of limb and extremity as determined by the controller may aid the simulation. For example, if the controller tracks the user's limb while user's extremity holds a virtual item (e.g., ball or dart) the controller may calculate when the user releases the virtual item (from force and proximity sensors, intensity (from accelerometer in inertial sensor) and rotational trajectory (from accelerometer and gyroscope). Examples of data used to calculate the quality of a gesture are described in relation to, at least, FIG. 5B.

FIG. 15A schematically illustrates a portion of a measurement circuit 1500 including one or more sensors. Measurement circuit 1500, a voltage divider, includes a voltage input 1502 from a voltage source (e.g., battery, power source) (not explicitly illustrated) and is communicatively coupled (e.g., galvanically connected, electrically coupled) to a first resistor 1504, $R_1$. Measurement circuit 1500 includes an output 1506 disposed between the first resistor 1504 and a second resistor 1508, $R_2$. In various implementations, the second resistor 1508 is a variable resistor such as, a force sensitive resistor, or a bend sensor. In various implementations, the first resistor 1504 is a variable resistor (further examples include a potentiometer or digital potentiometer) that may be used to tune measurement circuit 1500.

FIG. 15B schematically illustrates a portion of a measurement circuit 1520 including one or more sensors. Measurement circuit 1520, a voltage divider, includes a voltage input 1512 from a voltage source (e.g., oscillating source) and is communicatively coupled to a forward biased tunnel diode 1514 with resistance $r_t$. Measurement circuit 1520 includes an output 1516 disposed between the tunnel diode 1514 and a resistor 1518, $R_2$. In various implementations, the resistor 1518 is a variable resistor, such as, a force sensitive resistor, or a bend sensor. The tunnel diode 1514, has negative resistance, and thus may amplify the oscillating voltages at voltage input 1512 to create an amplified oscillating output at output 1516.

FIG. 15C schematically illustrates a portion of a measurement circuit 1530 including one or more sensors. Measurement circuit 1530, a Wheatstone bridge, includes a voltage input 1532 from a voltage source and is communicatively a network of resistors including an unknown, e.g., variable, resistor, such as, resistor 1534. Measurement circuit 1530 measures an unknown electrical resistance by balancing two legs of a bridge circuit where one leg of which includes the unknown component. For example, leg 1536 includes a variable resistor and leg 1538 includes resistors with known value.

FIG. 15D schematically illustrates a portion of a measurement circuit 1540 including one or more amplifiers. Measurement circuit 1540, an inverting amplifier, includes a voltage input 1542 from a voltage source and is communicatively a network of resistors and an operational amplifier. Resistor 1544, $R_1$, is coupled to the inverting input of the amplifier while the non-inverting input is connected to ground. Also connected to the inverting input is a feedback circuit including variable resistor 1546, $R_E$. Such feedback circuit may be tuned based upon device pose. Measurement circuit 1540 amplifies the input voltage to a value at output 1548 that is the negative of the ratio of $R_1$ over $R_E$.

FIG. 16A illustrates an exemplary semi-rigid web 1600. The semi-rigid web 1600 may be included in the wearable device 200, e.g., semi-rigid web 1600 is an example of frame 212 shown in FIGS. 2A and 2B. The semi-rigid web 1600 includes a first part 1602 which may be shaped to obtain a user's limb (e.g., wrist, ankle). Such shaping may be custom shape built for a specific user, via methods such as 3D printing or thermoplastic splinting, and may also provide passive support to the intended limb. For example, the first part 1602 may be crescent shaped and may partially enclose a user's wrist. The semi-rigid web 1600 may include a second part 1604 that may be sized and shaped to accommodate (e.g., receive, partially house, provide a rest for) electronics and power source(s) included in a wearable device, such as, wearable device 200. The semi-rigid web 1600 may include a gusset 1606, a structural body (e.g., knee, plate) disposed between the first part 1602 and the second part 1604. The gusset 1606 may add rigidity to the semi-rigid web 1600 at the interface of the first part 1602 and the second part 1604. The gusset 1606 may further shape the semi-rigid web 1600 to form to a user's limb.

The semi-rigid web 1600 may include a pair of edges (e.g., edge 1608) and may extend to a pair of ends (e.g., first end 1610). Semi-rigid web 1600 includes an inner face or side 1612 that orients toward the user's limb. For example, the inner side 1612 is shaped to match, receive, or accommodate a part of a user's limb (e.g., arm at wrist, leg at ankle). In some implementations, a plurality of force sensor sensors or a flexible web underlies the inner side 1612.

The web 1600 may be semi-rigid (e.g., resilient, solid, stiff but not inflexible). The semi-rigid web 1600 may include a semi-rigid material such as Acrylonitrile Butadiene Styrene (ABS), nylon (polyamide), polycarbonate, low density polyethylene, Poly-Lactic Acid (PLA), (copolymer) polypropylene, or polystyrene. The semi-rigid material included in semi-rigid web 1600 may have a Shore Hardness, D scale, of 80. The semi-rigid material may have a Shore Hardness, D scale, of between 60 and 95. The semi-rigid web 600 may have sufficient hardness (e.g., rigidity, stiffness) such that it may exert a normal force (e.g., detectable, material, or significant amount of normal force) to the force transmitted from an overlying layer. In other words, the rigidity of semi-rigid web 1600 causes an overlying layer to be squeezed between the semi-rigid web 1600 and a user's limb. If the overlying layer includes force/pressure sensors the sensors will detect volumetric changes in the user's limb. Material selection as indicated above beneficially allows force sensors, EMG sensors, and other applicable sensors, to be sandwiched between layers where material seams may be joined without the need for overmolding of the sensors, which could subject the sensors to heat and pressure that could cause sensor damage.

The semi-rigid web 1600 may extend to a second end 1614 disposed at or near the second part 1604. The second part 1604 may include (e.g., have defined within) one or more apertures, passages, or voids such as void 1616. One or more connectors, traces, or wires may pass through void 1616. Void 1616 may, in some implementations, receive one or more parts of a body in an interference fit, e.g., a housing including a tang may mate with a void, like void 1616.

The semi-rigid web 1600 may extend in at least a first direction 1618. Direction 1618 may align with the major axis of semi-rigid web 1600. Semi-rigid web 1600 may extend in a second direction 1620 which may be orthogonal to the first direction 1618, e.g., transverse to the major axis of semi-rigid web 1600.

FIG. 16B illustrates the semi-rigid web 1600 from a different point than for FIG. 16A showing at least the underside of the second part 1604. The second part 1604 is truncated at cutting line A-A' shown in FIG. 16A. FIG. 16B illustrates partial assembly 1630 including semi-rigid web 1600 and a flexible web or substrate 1632. Flexible substrate 1632 may include one or more plastics such as, polyether ether ketone, polyethylene terephthalate, and polyimide. Carried in or on the flexible substrate 1632 are one or more conductive traces placed there by photolithography, lamination, or the like. In some implementations, flexible substrate 1632 carries one or more parts of circuit elements, e.g., resistive material, piezo-electric ink, or the like. Flexible substrate 1632 may include one or more force sensors (not explicitly illustrated; for examples see, at least, FIGS. 1 and 17). A portion of flexible substrate 1632 may underlie a portion of semi-rigid web 1600, e.g., underlie inner side 1612. A portion of flexible substrate 1632, including zero, one, or more conductive traces may pass through one or more voids included in semi-rigid web 1600, e.g., void 1616.

Partial assembly 1630 may include a printed circuit board (PCB) 1634 (e.g., rigid PCB, flexible PCB) comprising one of more electronic components. Exemplary components include microcontrollers, measurement circuits, sensors, input devices, output devices, and the like, and includes components described herein in relation to, at least, FIGS. 1, 2A, 2B, 15A through 15D and 17A through 17D; and the like. Partial assembly 1630 may include power source 1636, such as, a battery.

FIG. 16C is an elevation view of partial assembly 1650 including the semi-rigid web 1600 and cap 1652. Cap 1652 may mate with the second part 1604 of the semi-rigid web 1600 to at least partially enclose one or more components, e.g., printed circuit board 1634, power source 1636.

FIG. 16C also illustrates how the semi-rigid web 1600 is shaped to encircle a part of a user's limb. For example, inner side 1612 faces a part of the user's arm, e.g., at the wrist. The semi-rigid web 1600 may be sized and shaped to receive the user's limb. The semi-rigid web 1600 may include an outer face 1654. The semi-rigid web 1600 may extend in the first direction 1618 which, as illustrated, may be a curve. The semi-rigid web 1600 may bend or flex to have a shape like curve 1656. Semi-rigid web 1600 may be coupled to a bend sensor that detects deflection or deformation of semi-rigid web 1600. For example, a bend sensor may be coupled to (e.g., connected to, temporarily coupled to) the semi-rigid web 1600 and oriented with respect to the first direction 1618 (e.g., a spatial extent), and in response to deviation from the first direction 1618 generates a bend signal (e.g., change in resistance).

FIG. 17A schematically illustrates an exemplary spatial arrangement 1700 for a plurality of force sensors included in the flexible substrate 1632. In FIG. 17B, the flexible substrate 1632 has been uncurled and flattened against plane of drawing sheet. The first direction 1618 is shown correspondingly flattened. A plurality of force sensors (e.g., force sensors 154) may be distributed over at least a part of the first direction 1618. A plurality of location marks 1710 show an exemplary plurality of locations of the plurality of force sensors. The plurality of location marks 1710 may be spaced regularly or irregularly. See, for example, location 1710-1 and location 1710-2 versus location 1710-N–2, location 1710-N–1, and location 1710-N.

In the exemplary spatial arrangement 1700, a plurality of locations 1710 may be closely space along the first direction 1618, e.g., group 1712. Force sensors at group 1712 may detect (e.g., capture, measure, record) normal force exerted by musculotendinous complex in the user's limb while being less effected by bend forces. Bend forces include forces detected in relation to bending of or more sensors due to the curvature of the user's limb. For example, force sensors at group 1712 includes locations 1710 closely spaced along the first direction 1618 to reduce the bend capture.

The force sensors carried in or on flexible web 1632 are responsive to forces (e.g., bending, normal force, torsion) applied to them. The locations 1710 are subject to conflicting constraints of increased spatial area (e.g., extent along first direction 1618) to capture a sufficient amount of the normal force exerted by the musculotendinous complex. As well, locations 1710 may be selected to minimize the capture of bending or torsion as these forces are often uncorrelated to extremity pose, gesture, etc. Increased spatial extent increases capture of bend and torsion. By placing a subset of force sensors at a group like group 1712, e.g., closely spaced along first direction 1618, the conflicting constraints are addressed. In some implementations, the force sensors are wired in parallel. A parallel arrangement of force sensors (e.g., sensors carried in or on flexible substrate 1632) reduces the capture of the bending while retaining good spatial coverage.

FIG. 17B is an elevation view illustrating a flexible web 1720 that may underlie at least a part of the semi-rigid web 1600. The flexible web 1720 may be shaped as a band, belt, or strap. Flexible web 1720 may underlie a part of flexible substrate 1632. Flexible web 1720 includes an inner face 1722 that may rest against a user's limb. Flexible web 1720 may include a thermoplastic that softens when heated and firms when cooled. Flexible web 1720 may include a Thermoplastic Elastomer (TPE) such as a Thermoplastic Olefin (TPO) or Thermoplastic Urethane (TPU). Flexible web 1720 may include a thermoset material like silicone. As well, fabrics or leathers may be utilized so long as such may be stitched at the seams. In some implementations the flexible web 1720 include a material with Shore Hardness A 40 (D 8) comparable to that of an eraser or inner tube. Additional materials may be selected which are flexible enough to allow for conformance to a user's arm (e.g., wrap, at least in part, around user's limb) while still being sufficiently stiff to transmit forces. Material selection as indicated above beneficially allows force sensors, EMG sensors, and other applicable sensors, to be sandwiched between layers where material seams may be joined without the need for over-molding of the sensors, which could subject the sensors to heat and pressure that could cause sensor damage.

As shown in FIG. 17B, the flexible web 1720 at inner face 1722 may include a plurality of locations (e.g., locations 1726, 1727, and 1728) for a plurality of force sensors with a different sensitivity than sensors at other locations, e.g., some of the plurality of locations 1710. The sensitivity of force sensors at locations 1726, 1727, and 1728 may be different than at other locations and may vary with over locations 1726, 1727, and 1728. The sensitivity of force sensors at locations 1726, 1727, and 1728 may be more sensitive than at other location on inner face 1722. It should be understood therefore that choosing sensors of different sensitivity and at different locations enables optimization relative to the amount of tendon/muscle force expected at that given location. Moreover, adding sensors that are mechanically isolated at different locations enables optimization relative to the amount of tendon/muscle force expected at that given location. Optimization includes finding an improvement, local optimum, global optimum, and the like.

In some implementations, a wearable input device, e.g., wearable device 200, includes a spring coupled to the semi-rigid web 1600 and biases the inner face 1612 of the semi-rigid web 1600 around the part of the user's limb. In some implementations, the wearable input device principally includes a bistable spring. A spring may overly the flexible web 1720 that contacts the user's limb.

In some implementations, flexible web 1720 underlies semi-rigid web 1600. In some implementations, the flexible web 1720 underlies a plurality of force sensors, e.g., force sensors carried in or on flexible substrate 1632. Flexible web 1720 may be bonded (e.g., glued together, parts given solidity as a whole) to semi-rigid web 1600. Flexible web 1720 may encapsulate one or more sensors in a plurality of sensors, e.g., encapsulate sensors in or carried upon flexible substrate 1632. The flexible substrate 1632 may be bonded to semi-rigid web 1600 or flexible web 1720.

In some implementations, flexible substrate 1632 includes a reference force sensor which is mechanically isolated from normal forces exerted by the user's limb (e.g., myographic forces). The reference force sensor may be isolated by one or more feature (e.g., a physical element such as a bump or void) in or on semi-rigid web 1600 or flexible web 1720 otherwise as shown in FIG. 17C. Each physical element may be oriented within the wearable device such that sensors face either inwards or outwards relative to the user—i.e., the sensors will be sandwiched within band materials but have their sensing areas directed inwards or outwards. The reference force sensor is subjected to torsion or bending but not normal force and may be used to calibrate adjacent force sensors not mechanically isolated.

In the manufacturing process, the flexible web 1720 may overlie one or more force sensors in a plurality of force sensors, and the semi-rigid web 1600. In operation, the flexible web 1720 may underlie one or more force sensors in a plurality of force sensors, and the semi-rigid web 1600. That is the notion of up depends on the context. Herein, as a default, inward toward the body of a user is associated with down and outward with up but in sometimes contexts or express statements will alter this convention.

In some implementations a bend sensor, e.g., bend sensor 164, is coupled to (e.g., connected to, temporarily coupled to) the flexible web 1720 and oriented with respect to the principal axis of the flexible web 1720 (e.g., a first direction 618), and in response to deviation from the principal axis of the flexible web 1720 generates a bend signal (e.g., change in resistance). In some implementations, one or more components of a bend sensor are carried on or in flexible substrate 632. The bend sensor, during operation, is subjected to torsion or bending but to a lesser degree a normal force. This absence of normal force may be used to calibrate adjacent force sensors.

FIG. 17C schematically illustrates a plurality of features that may be included in or proximate to semi-rigid web 1600 or the flexible web 1720. One or more bumps 1732 may be disposed between semi-rigid web 1600 and flexible substrate 1632 (not explicitly illustrated) or between flexible substrate 1632 and flexible web 720 (shown). In some implementations, a respective bump (not called out) in bumps 1732 isolates transmission of forces to a single force sensor included in flexible substrate 1632. The bumps may be made of a rigid, semi-rigid, or flexible material including materials described herein. In some implementations, a respective bump provides a mechanically isolated frame or rest that acts as a counter force to myographic forces applied one or more force sensors included in flexible substrate 1632.

In some implementations, flexible web 1720 includes a plurality of features, such as, bumps 1734 or voids 1736. A bump, as used herein, is a physical element that includes any projection, protrusion, ridge, dot, and other mass sitting proud of a surface. A bump may be formed from the same material as an underlying or overlying body. A bump may be of the same type of material or a different type material and placed on the underlying or overlying body at different stage in manufacturing. Void, as used herein, includes aperture, mayal, channel, duct, gap, passage, or the like within the bulk of a material or as part of a surface of the material. The voids may provide strain relief for the surrounding material or structure. For example, a void in voids 736 may stop strain created by bending from being transmitted to a force sensor.

In some implementations, semi-rigid web 1600 includes a plurality of features, such as, void 1738 and bump 1740. Voids like void 1738 may be a thin area of semi-rigid web 1600 to increase flexibility or mechanically isolate a part of semi-rigid web 1600. Bumps underlying or formed on the underside of semi-rigid web 1600 may provide a back or rest to squeeze one or more force sensors carried in or on flexible web 1632.

FIG. 17D is an elevation view illustrating a wrist band 1750 which includes flexible web 1720 and the semi-rigid web 1600. In some implementations, the semi-rigid web 1600 has a link like structure. The web 1600 includes a plurality of regions 1752-1 through 1752-4 which include a semi-rigid or rigid (e.g., non-deformable) material. The regions 1752-1 through 1752-4 may be joined together by rotatable joints (e.g., pins, thinner pieces of web 1600). The regions 1752-1 through 1752-4 may align with locations 1710 shown in FIG. 17A.

The wrist band 1750 may include one or more actuators that a controller may cause to constrict or loosen around the limb of a user. The controller may adjust the relative pose of wrist band 1750 to the user. Examples of actuators and operation of actuators are described herein at, at least, FIGS. 1 and 22.

FIG. 18 illustrates an example method 1800 (including, for example, acts 1802, 1804, etc.) of operation of a wearable device, such as, peripheral device 150, or wearable device 200. For method 1800, as with other methods taught herein, the various acts may be performed in a different order than that illustrated and described. As well, the acts may be performed in parallel or overlapping sequential operation by different circuitry, e.g., parallel processors. Additionally, the methods may omit some acts, and/or employ additional acts. One or more acts of method 1800 may be performed by or via one or more circuits, for instance, one or more hardware processors. In some implementations, method 1800 is performed by a controller, e.g., control subsystem 104 of apparatus 100, controller 156 of peripheral device 150.

Method 1800 may begin at 1801 by invocation from a controller. At 1802, the controller initializes an input device including a plurality of sensors. The plurality of sensors may include a plurality of force sensors and an additional sensor, e.g., bend sensor, blood sensor. For example, controller 156 initializes peripheral device 150 including measurement circuits, such as, circuits shown and described in FIG. 15.

At 1804, the controller obtains (e.g., accesses, gets, receives) at least one value from the plurality of sensors. The plurality sensors may include a photoplethysmograph (e.g., as part of blood sensor 162). The controller may obtain photoplethysmographic data from the photoplethysmograph. The plurality sensors may include a bend sensor. A bend sensor is responsive to deviation (e.g., bend, deflection) of the sensor or a body the bend sensor is coupled to (e.g., attached, connected, sliding engagement). The controller may obtain force data from the plurality of force sensors. Examples of sensors and acts in which the controller obtains at least one value from the exemplary sensors are shown and described herein in relation to at least FIGS. 1, 15, 16, and 19.

At 1806, the controller estimates a device pose for the input device relative to the user. For example, the controller estimates the donning position of wearable device 200 on a user's limb, e.g., ankle. The controller, at 1806, may estimate the tightness of a band, e.g., band (collectively 204A and 204B) relative to a user's wrist. At 1806, the controller may calculate the device pose for the input device based on data obtained from the plurality of sensors.

At 1808, the controller selects a mode of operation based on the device pose. The controller may classify the device pose as tight, medium, or loose; and/or proximal or distal.

Based on the classification the controller may select a measurement method or parameters appropriate for the device pose. A collection of measure methods and parameters may be provided in a look-up table which the controller may reference at 1808.

At 1810, the controller obtains force myographic data from a plurality of force sensors included in the plurality of sensors. The controller may obtain a plurality of values. The plurality of values may have a temporal and spatial extent. For example, a plurality of time periods and a plurality of locations, e.g., locations 1710.

At 1812, the controller determines volumetric changes in a user's limb based on the force myographic data and the mode of operation. For additional details on volumetric changes in a user's limb see, at least, FIGS. 3, 6, 8, 20, and 21.

At 1813, method 1800 ends until invoked again. In some implementations, method 1800 repeats until termination. Further examples of methods of operation are shown and described herein in relation to, at least, FIGS. 19 through 22. Acts shown and described in method 1800, or another method, may be included in other methods with appropriate changes unless the context dictates otherwise.

Figure 19:
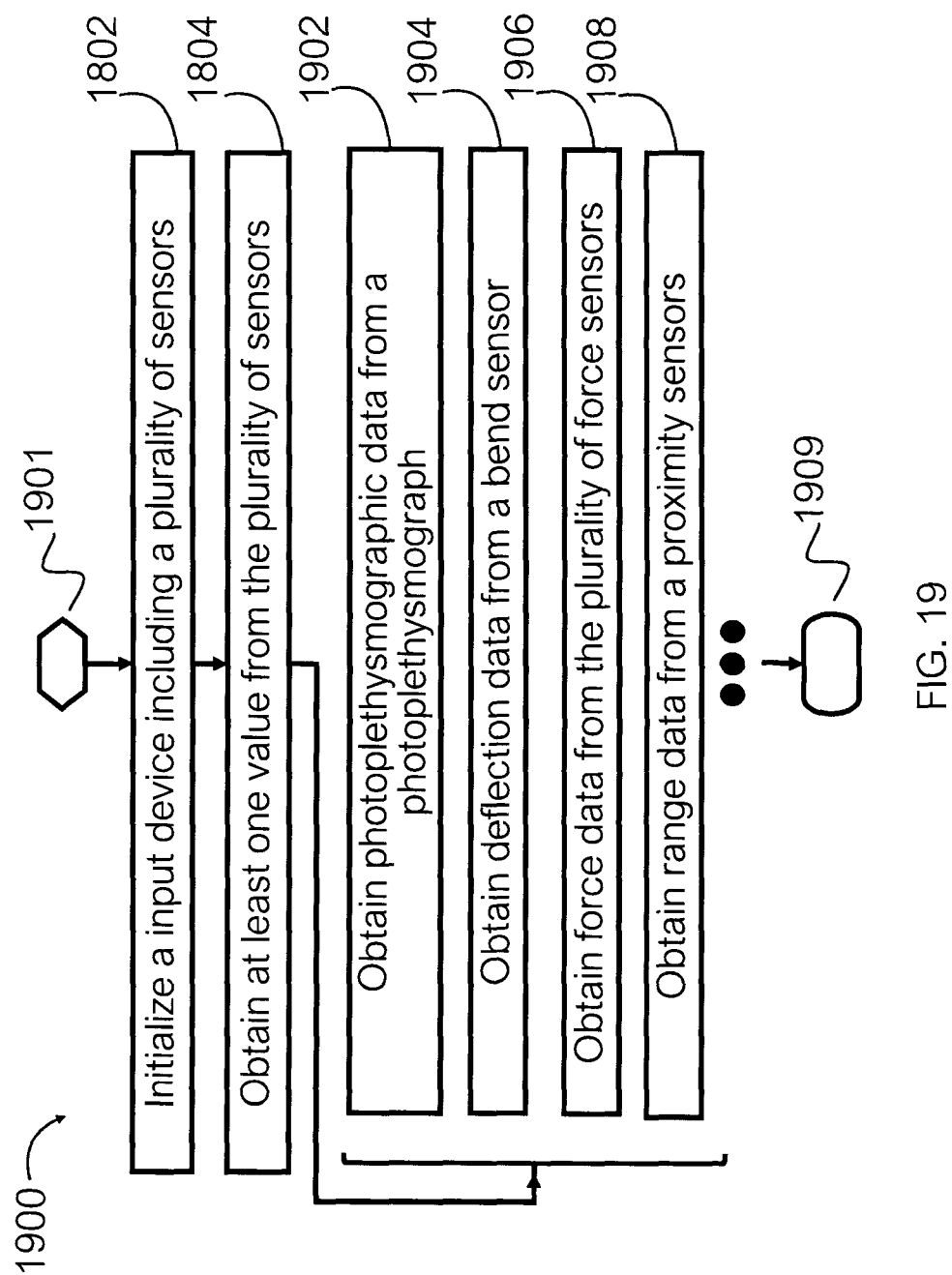

FIG. 19 illustrates an example method 1900 (including, for example, acts 1902, 1904, etc.) in accordance with the disclosure including a plurality of sensors. The plurality sensors may include one or more of a photoplethysmograph, a bend sensor, and a plurality of force sensors.

Method 1900 may begin at 1901 by invocation from a controller. At 1802, the controller initializes an input device including a plurality of sensors. At 1804, the controller obtains at least one value from the plurality of sensors. Act 1804 may include one or more further acts, such as, act 1902, act 1904, act 1906, act 1908, and the like.

At 1902, the controller obtains photoplethysmographic data from a photoplethysmograph. For example, the photoplethysmograph may be pulse oximeter. Components and method of operation of a photoplethysmograph are described herein at, at least, FIG. 1.

At 1904, the controller obtains deflection data from a bend sensor. A bend sensor is responsive to deviation (e.g., bend, deflection) of the sensor or a body the bend sensor is coupled to (e.g., attached, connected, sliding engagement). Components and method of operation of a bend sensor are described herein at, at least, FIGS. 1, 15, and 16.

At 1906, the controller obtains force data from the plurality of force sensors. At 906, the controller may aggregate (e.g., average, sum) the force data. Components and method of operation of force sensor are described herein at, at least, FIGS. 1, 2, and 15 through 17.

At 1908, the controller obtains range data from a proximity sensor, e.g., a proximity sensor communicatively coupled to the controller. Components and method of operation of proximity sensors are described herein at, at least, FIGS. 1 and 5 through 14.

Act 1804, may include one or more further acts such as the controller obtains environmental data from an environmental sensor. For example, device 200 may include an environmental sensor(s). The environmental sensor(s) may measure moisture, temperature, or the like. The environmental data may indicate if the user is sweating. The environmental sensor(s) may also measure the state/position of the band or user's limb in the real world. This may be used to detect gestures—for instance, is the user close to a particular object (determined by external cameras), or may be used to make the gesture recognition more accurate.

At 1909, method 1900 ends until invoked again. In some implementations, method 1900 repeats until termination, for instance, to detect changes in device pose, that then triggers re-estimation and reselection of mode of operation.

Further examples of methods of operation are shown and described herein in relation to, at least, FIGS. 18 and 20 through 22.

Figure 20:
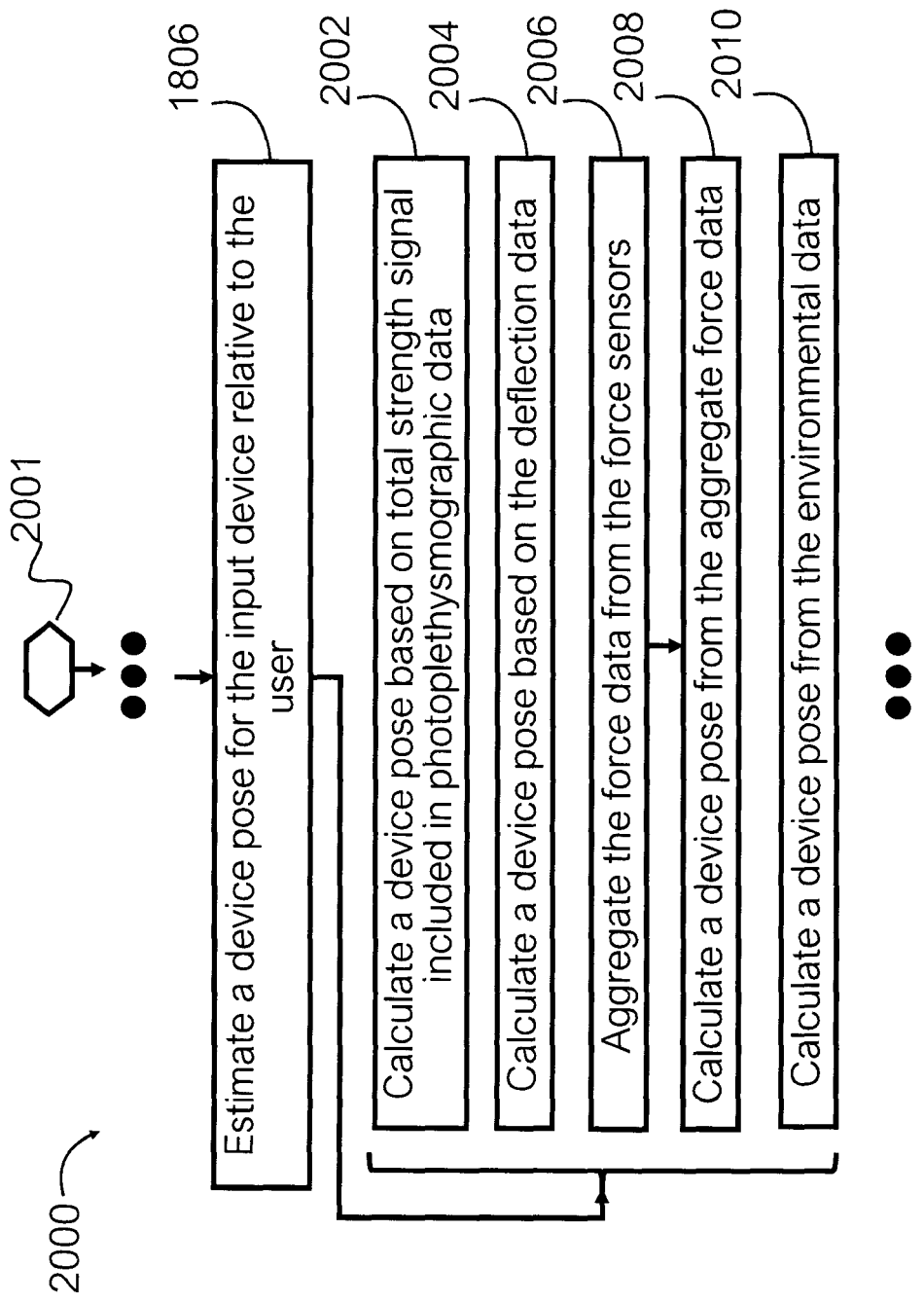

FIG. 20 illustrates an example method 2000 (including, for example, acts 2002, 2004, etc.) in accordance with the invention including a plurality of sensors. The plurality sensors may include one or more of a photoplethysmograph, a bend sensor, and a plurality of force sensors.

Method 2000 may start at 2001 by invocation from a controller. At 1806, the controller estimates a device pose for the input device relative to the user. Act 1806 may include one or more further acts, such as, act 2002, act 2004, act 2006, act 2008, act 2010, and the like.

At 2002, the controller estimates a device pose for the input device relative to the user from the photoplethysmographic data obtained at 1902 in FIG. 19. The photoplethysmographic data may include processor information that represents total signal strength. The total signal strength may, in value, be proportional to a distance between the photoplethysmograph and a user's limb, may alternatively be proportional/or related to rotational placement of photoplethysmograph (and hence device) on limb). At 2002, the controller may classify the photoplethysmographic data as part of making an estimate of the device pose, e.g., strong equated to tight, weak to lose.

At 2004, the controller estimates a device pose for the input device relative to the user from the deflection data obtained at 1904 in FIG. 19. A bend sensor is responsive to deviation of the sensor or a body the bend sensor is coupled to. The deflection data, processor-readable information, may indicate the curvature of the semi-rigid web 1600. At 2004, the controller may classify the deflection data as part of making an estimate of the device pose. Deflection may also be indicative of the size of the wrist of the user, and hence be used to process the FMG signal.

At 2006, the controller aggregates (e.g., average, sum) the myographic force data obtained at 1906 in FIG. 19. At 2008, the controller estimates a device pose of the wearable device on a user's limb from the aggregate of the myographic force data. The aggregate of the myographic force data will be proportional to the tightness, or looseness, of the wearable device. At 2008, the controller may classify the aggregation of the myographic force data as part of making an estimate of the device pose, e.g., strong equated to tight, weak to lose.

Act 1806 may include one or more further acts, such as, the controller estimates a device pose for the input device relative to the user from the range data obtained at 1906 in FIG. 19. A proximity sensors sensor is responsive to distance of objects in view of the sensor. The range data, processor-readable information, may indicate the distance from the device to a user's limb. At 1806, the controller may classify the range data as part of making an estimate of the device pose.

At 2010, the controller estimates a device pose for the input device relative to the user from environmental data obtained at 1804 in FIG. 18 or FIG. 19. The environmental data, processor-readable data, may quantify moisture, temperature, or the like, and indicate, if the user is sweating. A controller may infer at least two things from this. One, the wearable device may more easily slip in distal-proximal direction or rotate on limb. Two, tendons and muscles in the limb "bulk-up" (e.g. because of presence of lactic acid) with associated effect on volume changes. At 2010, the controller may classify the environmental data as part of making an estimate of the device pose.

Method 2000 continues with zero or more acts. Method 2000 ends until invoked again. In some implementations, method 2000 repeats until termination, for instance, to detect changes in device pose, that then triggers re-estimation and reselection of mode of operation. Further examples of methods of operation are shown and described herein in relation to, at least, FIGS. 18, 19, 21, and 22.

Figure 21:
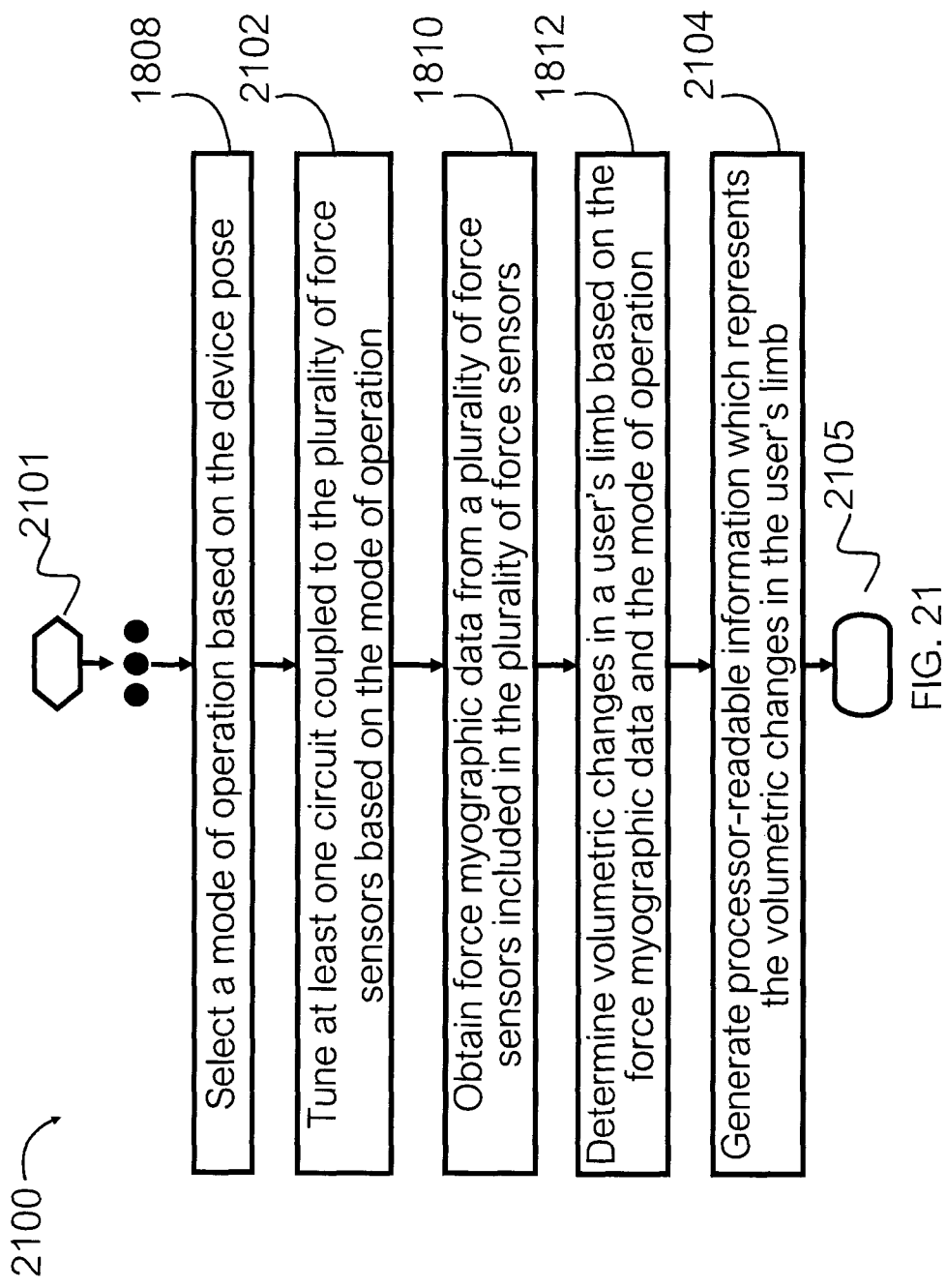

FIG. 21 illustrates an example method 2000 of operation of a device including a plurality of force sensors. The plurality of force sensors may include force sensitive resistors.

Method 2100 starts at 2101 by invocation from a controller. At 1808, the controller selects a mode of operation based on the device pose.

At 2102, the controller tunes at least one circuit coupled to the plurality of force sensors based on the mode of operation. Examples of circuits which may be coupled to the plurality of force sensors are shown in FIG. 1 and FIG. 15. At 2102, the controller may select a plurality of parameters to use in a set of processor-executable instructions for use. At 2102, the controller may select a set of processor-executable instructions for use in further acts. At 2102, the controller may set a digipotentiometer, throw a switch, or the like.

At 1810, the controller obtains myographic force data from the plurality of force sensors. The myographic force data may indicate changes in total volume of the limb. The myographic force data may indicate localized forces exerted by one or more tendons, muscles, or combinations.

At 1812, the controller determines volumetric changes in a user's limb based on the force myographic data and the mode of operation.

At 2104, the controller generates processor-readable information which represents the volumetric changes in the user's limb. At 2104, the controller may classify volumetric changes in the limb of the user into a category wherein the category is associated with at least one gesture made by the user wearing the input device. At 2104, the controller may cause a processor- and computer-readable storage device (e.g., storage device 108) to store the processor-readable information which represents the volumetric changes in the user's limb. At 2104, the controller may send the processor-readable information which represents the volumetric changes in the user's limb through a communication channel, e.g., communication channel 148.

At 2105, method 2100 ends until invoked again. In some implementations, method 2100 repeats until termination. Further examples of methods of operation are shown and described herein in relation to, at least, FIGS. 18 through 20 and 22.

Figure 22:
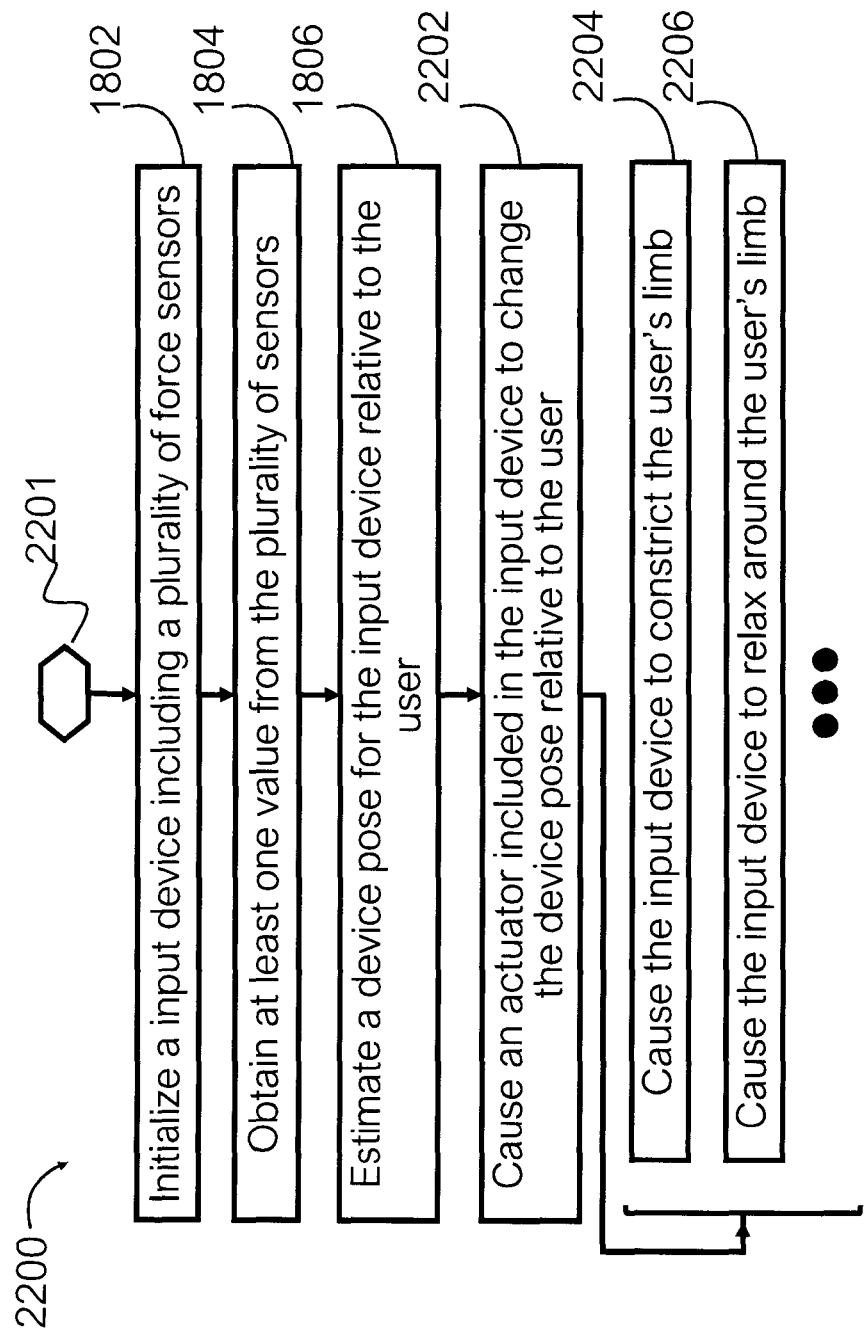

FIG. 22 illustrates an example method 2200 of operation of a device including a plurality of force sensors and an actuator. The actuator may include an electro activated polymer, a prismatic actuator, a rotatory actuator, or the like.

Method 2200 may start at 2201 by invocation from a controller. At 1802, the controller initializes an input device including a plurality of sensors which may be force sensors as indicated or any suitable sensor. At 1804, the controller obtains at least one value from the plurality of sensors. At 1806, the controller estimates a device pose for the input device relative to the user.

Figure 23:
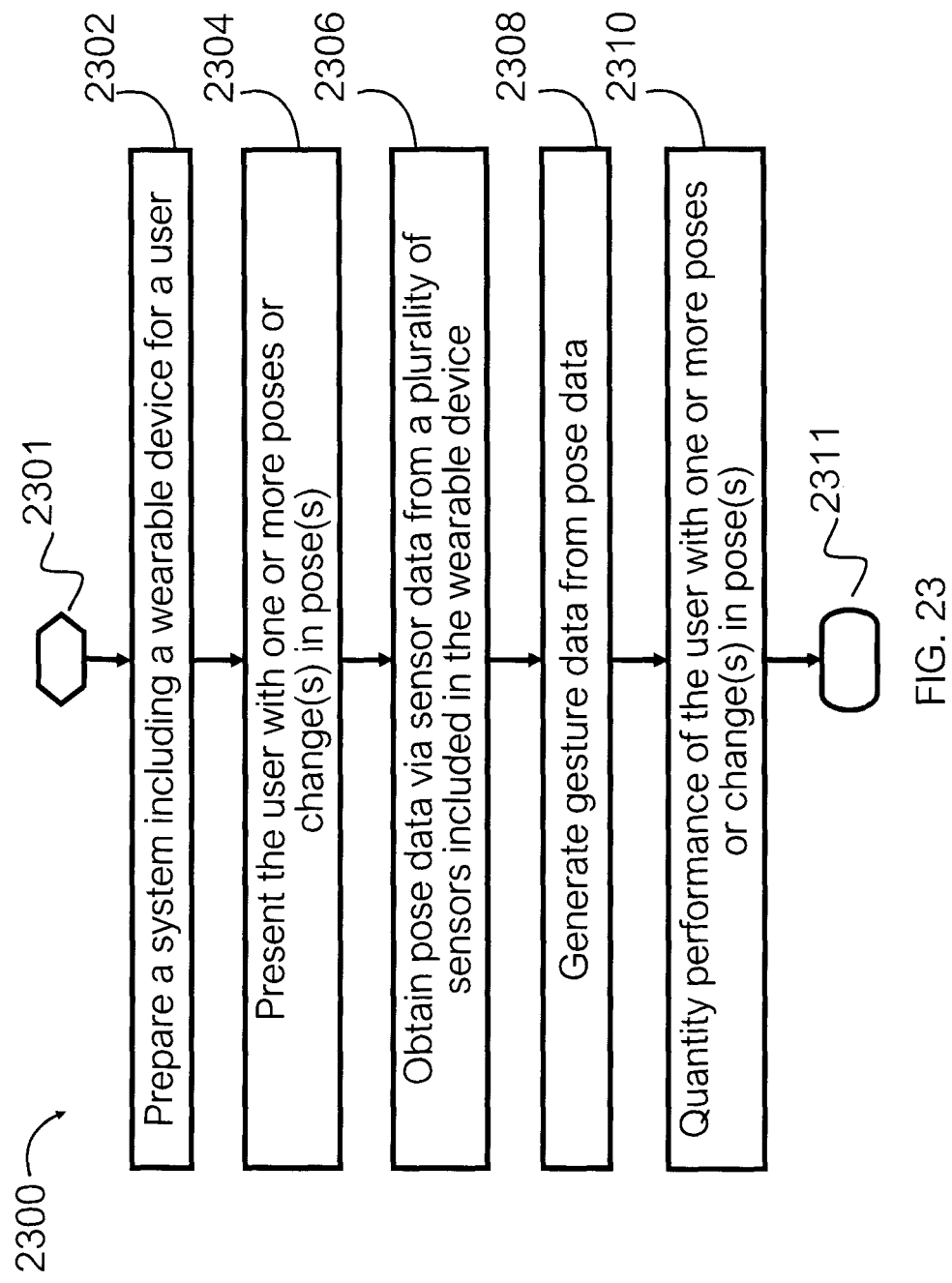
FIG. 23 is an alternative method in accordance with the present invention.

At 2202, the controller causes an actuator included in the wearable input device to change the device pose relative to the user. For example, at 2204, the controller causes the actuator to constrict the input device about the user's limb. For example, at 2206, the controller causes the actuator to relax the input device about the user's limb. The controller at 2202 may cause the wearable input device to assume a device pose in a range acceptable device poses, e.g., poses previously used for force myography, poses shown in testing to produce good results. FIG. 23 illustrates an example method 2300 of operation for an apparatus including a wearable device, such as, peripheral device 150, or wearable device 200. For method 2300, as with other methods taught herein, the various acts may be performed in a different order than that illustrated and described. As well, the acts may be performed in different parts of a distributed system, e.g., tele-rehabilitation. Indeed, in tele-rehabilitation use-cases, the present device or methods may be utilized to gamify rehabilitation—e.g., a patient may have to move a wrist past a target angle of flexion for the gesture to be communicated to an audiovisual game. For example, such acts may be performed via communication channel 148 between well separated instances of apparatus 100 and peripheral device 150. One or more acts of method 2300 may be performed by or via one or more circuits, for instance, one or more hardware processors in different locations. In some implementations, method 2300 is performed by a controller, e.g., control subsystem 104 of apparatus 100, controller 156 of peripheral device 150.

Method 2300 may begin at 2301 by invocation from a controller. At 2302, the controller prepares an apparatus including a wearable device for a user, e.g., a first user. The wearable device includes a plurality of sensors, e.g., force sensors, proximity sensors, and inertial sensors. The wearable when worn by the user is disposed near a join. At 2302, the controller may associate a wearable device, to a record of user, and a series of tasks for the user to perform. The series of tasks for the user to perform may be included in direction information provided by a second user. It should be understood that the second user is effectively a diagnostic-user that may be a technician, clinician, or any other individual providing directives to the subject-user.

At 2304, the controller presents the user with one or more poses or change(s) in pose(s), e.g., direction information, which are instructions to the subject-user corresponding to target poses. The poses or changes in pose may be part of a task pipeline designed to assess one or more aspects of the user, e.g., functional capabilities of user's extremities, joint, or limb; sobriety; ability to follow directions; or the like, as specified by a second user. In some instances, the second user (e.g., therapist) may guide, assist or maneuver the first user's extremities, joint, or limb (i.e., patient's extremities, joints, or limbs) into the poses or changes in poses per the target poses, with or without voluntary movement from the first user. The one or more poses or change(s) in pose(s) are processor-readable information that may be presented to the user in a rehabilitation setting, e.g., tele-rehabilitation, gamification. For example, at 2304, the controller may cause information that represents one or more poses or one or more change in poses to be presented to the first or second users.

At 2306, the controller obtains (e.g., accesses, gets, receives) pose data for the joint. At 2306, the controller may obtain data from one or more sensors in the wearable device or ancillary sensors. The controller may convert or combine data from one or more sensor types as described herein. At 2306, the controller may obtain pose data for the extremity or limb proximate to the location were the user wears the wearable device. At 2308, the controller may generate gesture data from the pose data. The gesture data may include detection of a motion, quantification of a motion, quantification of a pose, or a combination of motion and pose for one or more limb, joint, and/or extremity configuration.

At 2310, the controller may quantify performance of the first user at the one or more poses or one or more change in poses for the joint. The controller may quantify (e.g., assess, compare to standard) the performance of the user at performing the one or more poses or change(s) in pose(s). Optionally the controller may generate processor-readable achieve data which represents the user's success at performing the one or more poses or change(s) in pose(s). The control may take an action, or causes and action to be taken, based on the gesture information (not show). The controller may send processor-readable data (e.g., the pose data, gesture data, achievement) to a storage device or through a communication channel that represents the gesture information.

The controller may also advantageously compare the signals from the device for the same target pose, between individuals. Illustrative implementations may include: monitoring ergonomics whereby Person A may flex their wrist more than Person B to achieve the same pose, which may lead to injury; and monitoring biomechanics whereby Person A may exert more tendon tension when lifting a weight (external loading) when compared to Person B, not because the weight has changed, but perhaps because Person A uses a different grip style, more grip force, or simply has different biomechanical properties. In both of these illustrative implementations, the differences in limb and extremity use and biomechanics would be detected and quantified, which may detect or predict injury. In some instances, Person A may be provided with coaching, feedback, training, more frequent breaks, ergonomic support or different tools in order to reduce the differences and prevent injury or facilitate recovery.

At 2311, method 2300 ends until invoked again. In some implementations, method 2300 repeats until termination. Method 2300 may be employed in different contexts for the same user, e.g., benchmark the user's baseline impairment, progress through a rehabilitation program.

Figure 24:
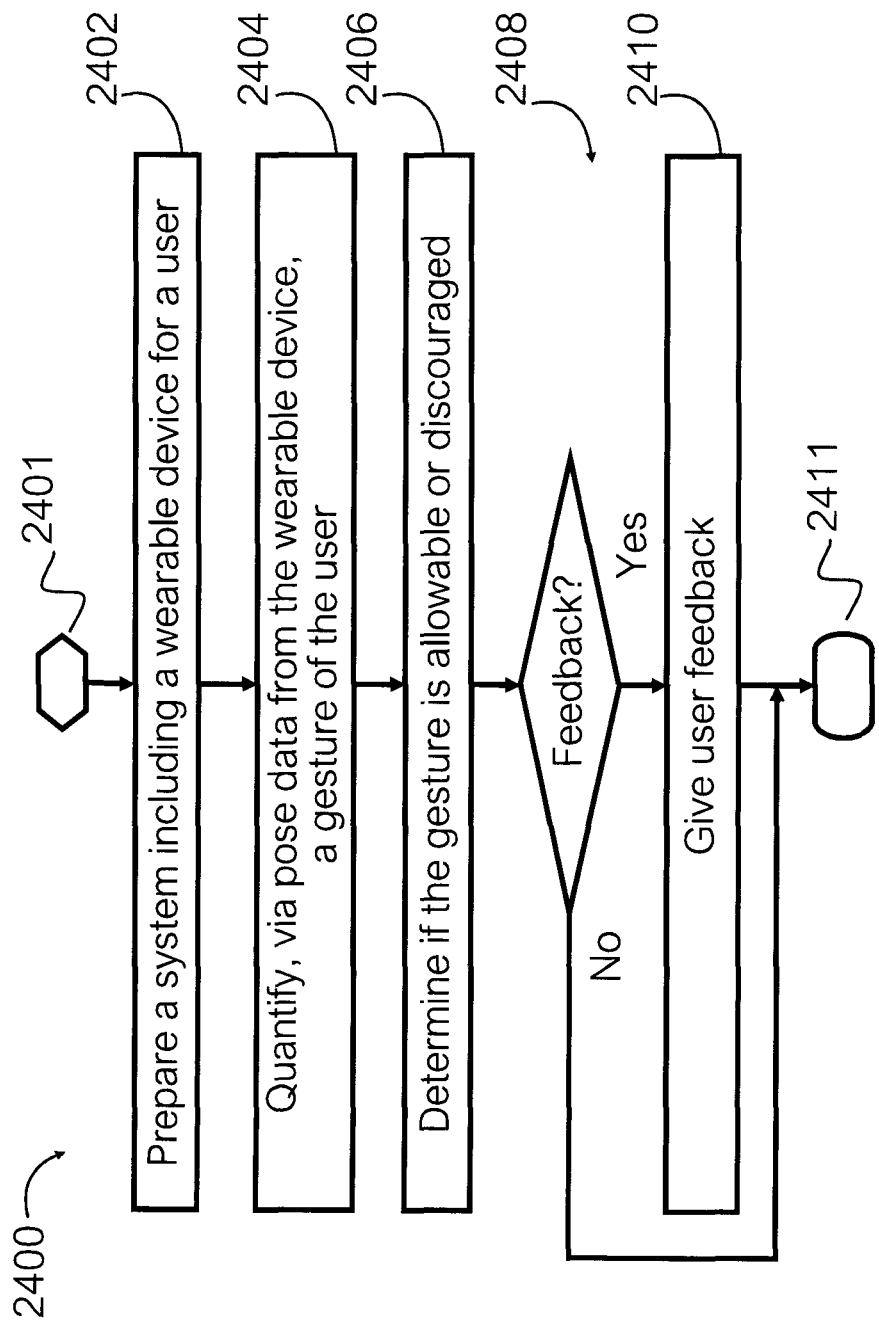
FIG. 24 is an alternative method in accordance with the present invention.

FIG. 24 illustrates an example method 2400 of operation for an apparatus including a wearable device. Method 2400 may be implemented by a distributed system, e.g., parts of apparatus 100 are separated and in communication with each other or at least communicatively coupled. Method 2400 is described with a singular wearable device on one user but may be practiced including two or more wearable devices worn by one user, two or more users. Method 2400 may be part of a method to give feedback to a user on movement of an extremity, joint, or limb (e.g., hand, wrist and forearm) as part of a rehabilitation program for injuries (e.g., neuro-injuries, orthopedic-injuries) or training (e.g., posture correction, a performance training program for elite sport).

Method 2400 may begin at 2401 by invocation from a controller. At 2402, the controller prepares an apparatus including a wearable device for a user. For example, the controller associates a wearable device, and a prescribed series of allowable and discouraged gestures (e.g., pose, change in pose, combinations), associated feedback thresholds, or the like. The feedback thresholds may be positive and associated with a first signal type to inform or reward the user. The feedback thresholds may be negative and associated with a second signal type to warn or alert the user.

At 2404, the controller detects a gesture of the user, e.g., pose, change(s) in pose(s), or combination. The poses or changes in pose may be part of a task the user is performing as part of their daily tasks, e.g., in context of home, commute, work, or school. At 2406, the controller, determines if the gesture is an allowable gesture or a discouraged gesture. The gesture may be allowable, for example, in some implementations, the controller may determine if the user is achieving sufficient joint angle, grip strength, pose duration or sufficient use or exercise within a day for an exercise to be effective. The gesture may be discouraged, for example, in some implementations, the controller may determine if the user is at or past a prescribed threshold, for example, safe limit for angles, duration, or force. Any threshold (e.g., target or limit) may be associated with a pose or change in pose, number of times joint moved, duration, the ratio between opposing movements (e.g., flexion versus extension). It should be readily apparent therefore that the present invention may also be used to encourage and ensure compliance with a rehabilitation exercise program or a strength training program. For example, to avoid ailments one may set thresholds related for even or balanced opposing movements (e.g., flexion versus extension).

At 2408, the controller determines if feedback should be given to the user. The controller, at 2408, may determine if a threshold has been reached or exceeded. For example, the user may have achieved a positive milestone, e.g., target angle, number of repetitions, pose duration. The feedback may include a first signal, such as, an alert or alarm to warn of risk of injury or possible injury, e.g., over-use, injurious use, non-advisable use. The feedback may include a second signal, such as, an alert or alarm to alert user of achievement. If feedback is not needed, 2408-No, processing continues at after 2410. If feedback is needed, 2408-Yes, processing continues at 2410.

At 2410, the controller takes an action, or causes an action to be taken, to provide feedback to the user. In some implementations, the controller may cause the wearable device to vibrate or beep when a threshold (e.g., target or limit) is reached. The type or degree of the feedback may vary with the nature of gesture. For example, for allowable gestures and feedback is needed (e.g., target reached, personal best) a first signal may be sent to the wearable device. For example, for discouraged gesture (e.g., limit reached) and feedback is needed a second signal may be sent to the wearable device.

At 2411, method 2400 ends until invoked again. In some implementations, method 2400 repeats until termination.

Having thus described the inventive apparatus and several methods related thereto, it should be readily apparent that many useful implementations may be provided within areas beyond merely gesture recognition. As mentioned, the present invention may be utilized in many different practical applications including those implementations within the medical arts.

For example, a combination of the gesture recognition and muscle/tendon monitoring aspects of the present invention provides for a useful method and apparatus for detecting a subject-user's hand grip strength. See, for example, FIGS. 1, 20, and 24. In particular, it has been shown that FMG is correlated to the grip strength of a user. The inventive apparatus as a wrist band implementation will capture signals that represent the state of hand, wrist, forearm, while processing differences within the signal. As described herein with at least FIGS. 1 and 6 through 14, to better obtain information on grip strength, the impact of wrist flexion/extension, radial/ulnar deviation and forearm pronation/supination needs to be removed or otherwise reduced from the FMG signal which may be achieved by using proximity sensors to obtain the true position of the wrist, as described above, to remove any related impact on the FMG signal.

Additionally, at least one IMU sensor obtains the true position of the of forearm (e.g., pronation/supination) in order to remove any related impact on the FMG signal. As well, movement/position of fingers would also need to be disambiguated. Once the FMG signal has been disambiguated, such signal will then be proportional to the grip strength for that particular grip style. The signal may then be used in a workflow that allows for the grip style to analyzed, as described below in the context of monitoring tendons.

In terms of the monitoring of tendons by way of the present invention, FMG methods and apparatus capture the pressure (e.g., force, impact) which the subject-user's tendons and muscles exert on the given force sensors. This signal consists of multiple components. As the user changes their wrist, forearm, and hand position, the tendons and muscles change volume and position and hence exert a different pressure. However, this is further confounded by the fact that the wrist band of the present invention itself shifts or tightens/slackens due to the change in morphology of the wrist. See herein at, at least, FIGS. 1, 18, and 20. In a given consistent wrist action, forearm and hand position, the FMG signal would detect changes in the tension within the tendon—which would be proportional to either changes in the grip force exerted by the hand, or other loading on the limb (for example, holding a dumbbell).

Accordingly, one may monitor the state of the tendons and muscles by controlling for band tightness, slackness or donning position. See herein at, at least, FIGS. 1, 18, and 20.

Alternatively, if interested in grip-strength or external loading monitoring may be achieved by using a workflow where the inventive band is calibrated for a particular wrist, forearm and hand positions with neutral/normal grip strength, whereby any additional tendon tension, over and above the calibrated amounts, would be proportional to the grip force exerted or external loading. Monitoring in such instance may also be achieved by using a workflow where the inventive band is calibrated for multiple wrist, forearm and hand positions with neutral/normal grip strength. Monitoring may include detecting if the user is in one of any valid wrist, forearm and hand position. Any additional tendon tension over and above the calibrated amounts would be proportional to the grip force exerted or external loading. See FIGS. 1, 3, and 17.

Another alternative, if interested in monitoring overall use/state of the tendons and muscles may involve localized tendon and muscle movement which may be measured and compared to a nominal data-base. For example, in ailments such as Carpal Tunnel Syndrome, which may result from constant loading of the hand tendons passing through the wrist, the inventive apparatus may be utilized to prompt the user when they have been exerting specific tendons or muscles for more than a certain period. By further example, in ailments such as Golfer's and Tennis Elbow, which may result from unequal use of the extender/flexor tendons of the wrist, the inventive apparatus may be utilized as a timer or repetition counter to estimate the unequal loading period during the activity and to warn the user about overexertion. See herein at, at least, FIG. 24. The inventive apparatus may also be utilized for post-session therapy to encourage the use of the complimentary tendons. By still further example, the inventive apparatus may be used to provide grip quality metrics in conjunction with the estimation of grip strength, and tendon tension profile for a wrist of a healthy individual. By yet still a further example, for workers performing repetitive motion, the inventive apparatus may be utilized to compare tension loading between individuals who do and do not suffer from injuries, encouraging the afflicted individuals to perform repetitive actions like their healthier counterparts, or less healthy individual may also be asked to take breaks, or could be given different tools to improve ergonomics, or could be given more frequent breaks when compared to healthier counterpart, or could rotate jobs with healthier counterpart. By yet another example, for stroke patients, the inventive apparatus may be utilized to check for tension in tendons which may not be imperative to the task. Such event may occur from erroneous engagement of a muscle group, but the apparatus may be used to measure the progress of an individual in being able to relax unnecessary muscle groups during the given task.

Further implementations are summarized in the following examples.

Example 1: An article of manufacture including a semi-rigid first web including a first spatial extent and a first inner side, wherein the semi-rigid first web is shaped to receive a part of a user's limb at the first inner side. The article of manufacture further including a plurality of force sensors distributed over at least a part of the first spatial extent and positioned proximate to the inner side of the semi-rigid first web; and a flexible second web underlying the first inner side of the semi-rigid first web and the plurality of force sensors.

Example 2: The article of example 1 wherein the flexible second web is bonded to the semi-rigid first web.

Example 3: The article of example 1 wherein the plurality of force sensors is bonded to the semi-rigid first web or the flexible second web.

Example 4: The article of examples 1, 2, or 3 wherein the flexible second web encapsulates at least one force sensor included in the plurality of force sensors.

Example 5: The article of example 1 further including a bend sensor coupled to the semi-rigid first web, oriented with respect to the first spatial extent, wherein the bend sensor in response to deviation from the first spatial extent generates a bend signal.

Example 6: The article of example 1 wherein the semi-rigid first web further comprises at least one bump or at least one void.

Example 7: The article of example 1 wherein the flexible second web further comprises a plurality of features.

Example 8: The article of example 7 wherein the flexible second web includes a second inner side and the plurality of features comprises at least one bump defined on the second inner side included in the flexible second web.

Example 9: The article of example 7 wherein the flexible second web includes a first outer side and the plurality of features comprises at least one bump defined on the first outer side included in the flexible second web.

Example 10: The article of example 7 wherein the plurality of features comprises:
at least one void defined in the flexible second web.

Example 11: The article of example 1 further including:
a plurality of bodies which underlie the plurality of force sensors, wherein a respective body in the plurality of bodies underlies a respective force sensor in the plurality of force sensors.

Example 12: The article of example 1 further including:
at least one processor communicatively coupled to the plurality of force sensors.

Example 13: The article of example 12 further including a photoplethysmograph communicatively coupled to the least one processor.

Example 14: The article of example 1 further including:
a proximity sensor communicatively coupled to the at least one processor.

Example 15: The article of example 1 further including: an environmental sensor communicatively coupled to the at least one processor.

Example 16: The article of example 1 further including at least one voltage divider circuit communicatively coupled to the plurality of force sensors.

Example 17: The article of example 1 wherein the plurality of force sensors further comprises: at least a first subset of force sensors closely spaced along the first extent.

Example 18: The article of example 1 further including: at least a first part of a fastener coupled to the semi-rigid first web.

Example 19: The article of example 1 further including a spring coupled to the semi-rigid first web which biases the inner face of the semi-rigid first web around the part of the user's limb.

Example 20: The article of example 1 further including an actuator coupled to the semi-rigid first web which when activated constricts the inner face of the semi-rigid first web around the part of the user's limb.

Example 21: A system including a wearable device including a plurality of sensors, and wherein, when worn by a first user, is disposed near a joint; at least one processor communicatively coupled to the wearable device; and at least one tangible computer-readable storage device communicatively coupled to the at least one processor. The at least one tangible computer-readable storage device stores processor-executable instructions which, when executed by the at least one processor, cause the at least one processor to: cause the first user to be presented with direction information that represents one or more poses or one or more change in poses for the joint; obtain, via the plurality of sensors, joint pose data for the joint; generate gesture data from the joint pose data; and quantify performance of the first user at the one or more poses or one or more change in poses for the joint.

Example 22: The system of example 21 wherein, when executed, the processor-executable instructions further cause the at least one processor to: obtain from a second user the direction information that represents one or more poses or one or more change in poses for the joint.

Example 23: The system of example 22 wherein, when executed, the processor-executable instructions further cause the at least one processor to wherein, when executed, the processor-executable instructions further cause the at least one processor to: generate performance data which quantifies performance of the first user at the one or more poses or one or more change in poses; and share the performance data with the first user or a second user.

Example 24: A system including a wearable device including a plurality of sensors, and wherein, when worn by a first user, is disposed near a joint; at least one processor communicatively coupled to the wearable device; and at least one tangible computer-readable storage device communicatively coupled to the at least one processor. The at least one tangible computer-readable storage device stores processor-executable instructions which, when executed by the at least one processor, cause the at least one processor to: obtain, via the plurality of sensors, joint pose data for the joint; generate gesture data from the joint pose data; quantify a gesture for the user; obtain feedback threshold data; determine if feedback should be provided to user per the feedback threshold data; and if feedback should be provided, cause a feedback signal to be sent to the wearable device.

Example 25: The system of example 24 wherein, when executed, the processor-executable instructions further cause the at least one processor to: process the feedback signal; and generate an output to be noticed by the user at the wearable device.

Unless otherwise specified herein, or unless the context clearly dictates otherwise the term about modifying a numerical quantity means plus or minus ten (10) percent. Unless otherwise specified, or unless the context dictates otherwise, between two numerical values is to be read as between and including the two numerical values.

In the above description, some specific details are included to provide an understanding of various disclosed implementations. One skilled in the relevant art, however, will recognize that implementations may be practiced without one or more of these specific details, parts of a method, components, materials, etc. In some instances, well-known structures associated with input-devices and/or processor-based devices and/or wearable devices and/or information processing, such as straps, Velcro®, buckles, wires, traces, jumpers, resistors, capacitors, inductors, processor-executable instructions (e.g., BIOS, drivers), have not been shown or described in detail to avoid unnecessarily obscuring descriptions of the disclosed implementations.

In this specification and appended claims "a", "an", "one", or "another" applied to "embodiment", "example", or "implementation" is used in the sense that a particular referent feature, structure, or characteristic described in connection with the embodiment, example, or implementation is included in at least one embodiment, example, or implementation. Thus, phrases like "in one embodiment", "in an embodiment", or "another embodiment" are not necessarily all referring to the same embodiment. Furthermore, the particular features, structures, or characteristics may be combined in any suitable manner in one or more embodiments, examples, or implementations.

As used in this specification and the appended claims, the singular forms of articles, such as "a", "an", and "the", include plural referents unless the context mandates otherwise. It should also be noted that the term "or" is generally employed in its sense including "and/or" unless the context mandates otherwise.

Unless the context requires otherwise, throughout this specification and appended claims, the word "comprise" and variations thereof, such as, "comprises" and "comprising" are to be interpreted in an open, inclusive sense, that is, as "including, but not limited to".

All of the US patents, US patent application publications, US patent applications, foreign patents, foreign patent applications, and non-patent publications referred to in this specification, or referred to on any application data sheet, including, but not limited to U.S. provisional applications 62/585,709 and 62/607,223 are incorporated by reference in their entireties for all purposes herein.

While certain features of the described embodiments and implementations have been described herein, many modifications, substitutions, changes and equivalents will now occur to those skilled in the art. It is, therefore, to be understood that the appended claims are intended to cover all such modifications and changes as fall within the scope of the described embodiments and implementations.

The invention claimed is:

1. An apparatus comprising:
at least one peripheral device worn by a subject-user and having a plurality of sensors, wherein the plurality of sensors comprises 1) a first sensor group comprising one or both of a proximity sensor or an inertial sensor, and 2) a second sensor group comprising one or more myographic sensors;

at least one processor for receiving and processing data from said plurality of sensors;

a peripheral device interface communicatively coupling said at least one peripheral device with said at least one processor; and at least one tangible computer-readable storage device communicatively coupled to said at least one processor and which stores processor-executable instructions which, when executed by said at least one processor, cause said at least one processor to use data generated by the first sensor group to monitor a limb pose comprising one or more angular positions of a limb, and to use data generated by the second sensor group to measure muscle and tendon activity, and combine the data generated by the first sensor group and second sensor group to determine extremity pose.

2. The apparatus as claimed in claim 1, wherein said plurality of sensors are mechanically isolated from one another.

3. The apparatus as claimed in claim 2, wherein said mechanical isolation enables said at least one peripheral device to isolate localized transmission of forces to a given sensor of said plurality of sensors.

4. The apparatus as claimed in claim 1, comprising said proximity sensor, wherein the data generated by the first sensor group comprises proximity data from said proximity sensor.

5. The apparatus as claimed in claim 4, wherein said proximity sensor is selected from a group consisting of: a time of flight sensor, a camera, and a capacitive sensor.

6. The apparatus as claimed in claim 1, comprising said inertial sensor, wherein the data generated by the first sensor group comprises inertial measurement data.

7. The apparatus as claimed in claim 6, wherein, when executed, said processor-executable instructions further cause said at least one processor to generate limb pose information from said inertial measurement data, wherein said limb pose information represents the limb pose of said user, such that said at least one processor generates gesture information from said extremity pose information and limb pose information.

8. The apparatus as claimed in claim 7, wherein said inertial sensor is selected from a group consisting of: an altitude sensor, an accelerometer, a compass, a gyroscope, a magnetometer, and a pressure sensor.

9. The apparatus as claimed in claim 1, wherein said at least one peripheral device further comprises a spring biasing a surface of said at least one peripheral device towards an extremity of said subject-user.

10. The apparatus as claimed in claim 1, wherein said at least one processor determines a device pose using data received from one or both of 1) one or more of said plurality of sensors, and/or or 2) one or more peripheral sensors disposed upon said at least one peripheral device, wherein the device pose represents a pose of the at least one peripheral device relative to the user's body.

11. The apparatus as claimed in claim 1, wherein said one or more myographic sensors is selected from a group consisting of: a force sensor, a strain sensor, a pressure sensor; a piezo-resistive sensor, a piezo-electric sensor, an electromyographic sensor, and a capacitive sensor.

12. The apparatus as claimed in claim 1, wherein, when executed, said processor-executable instructions further cause said at least one processor to generate and monitor information relating to tendon use for an identified extremity pose.

13. The apparatus as claimed in claim 1, further comprising one or more ancillary sensors spaced apart from said at least one peripheral device.

14. An apparatus comprising:

at least one peripheral device worn by a subject-user and having a plurality of sensors, wherein the plurality of sensors comprises 1) a first sensor group comprising one or both of a proximity sensor or an inertial sensor, and 2) a second sensor group comprising one or more myographic sensors;

at least one processor for receiving and processing data from said plurality of sensors;

a peripheral device interface communicatively coupling said at least one peripheral device with said at least one processor; and at least one tangible computer-readable storage device communicatively coupled to said at least one processor and which stores processor-executable instructions which, when executed by said at least one processor, cause said at least one processor to use data generated by the first sensor group to monitor a limb pose, and to use data generated by the second sensor group to measure muscle and tendon activity, and combine the data generated by the first sensor group and second sensor group to determine extremity pose information, wherein, when executed, said processor-executable instructions further causes said at least one processor to generate grip strength information.

15. The apparatus as claimed in claim 14, wherein said at least one processor compares the grip strength information with a calibrated grip strength for a particular wrist, forearm and hand position.

16. The apparatus as claimed in claim 15, wherein said at least one processor provides a feedback signal to said user based on said grip strength information.

17. The apparatus as claimed in claim 14, wherein said plurality of sensors are mechanically isolated from one another.

18. The apparatus as claimed in claim 17, wherein said mechanical isolation enables said at least one peripheral device to isolate localized transmission of forces to a given sensor of said plurality of sensors.

19. The apparatus as claimed in claim 14, comprising said proximity sensor, wherein the data generated by the first sensor group comprises proximity data from said proximity sensor.

20. The apparatus as claimed in claim 19, wherein said proximity sensor is selected from a group consisting of: a time of flight sensor, a camera, and a capacitive sensor.

21. The apparatus as claimed in claim 14, comprising said inertial sensor, wherein the data generated by the first sensor group comprises inertial measurement data.

22. The apparatus as claimed in claim 21, wherein, when executed, said processor-executable instructions further cause said at least one processor to generate limb pose information from said inertial measurement data, wherein said limb pose information represents the limb pose of said user, such that said at least one processor generates gesture information from said extremity pose information and limb pose information.

23. The apparatus as claimed in claim 22, wherein said inertial sensor is selected from a group consisting of: an altitude sensor, an accelerometer, a compass, a gyroscope, a magnetometer, and a pressure sensor.

24. The apparatus as claimed in claim 14, wherein said at least one peripheral device further comprises a spring biasing a surface of said at least one peripheral device towards an extremity of said subject-user.

25. The apparatus as claimed in claim 14, wherein said at least one processor determines a device pose using data received from one or both of 1) one or more of said plurality of sensors, or 2) one or more peripheral sensors disposed upon said at least one peripheral device, wherein the device pose represents a pose of the at least one peripheral device relative to the user's body.

26. The apparatus as claimed in claim 14, wherein said one or more myographic sensors is selected from a group consisting of: a force sensor, a strain sensor, a pressure sensor; a piezo-resistive sensor, a piezo-electric sensor, an electromyographic sensor, and a capacitive sensor.

27. The apparatus as claimed in claim 14, further comprising one or more ancillary sensors spaced apart from said at least one peripheral device.

28. An apparatus comprising:
    at least one peripheral device worn by a subject-user and having a plurality of sensors, wherein the plurality of sensors comprises 1) a first sensor group comprising one or both of a proximity sensor or an inertial sensor, and 2) a second sensor group comprising one or more myographic sensors;
    at least one processor for receiving and processing data from said plurality of sensors;
    a peripheral device interface communicatively coupling said at least one peripheral device with said at least one processor; and
    at least one tangible computer-readable storage device communicatively coupled to said at least one processor and which stores processor-executable instructions which, when executed by said at least one processor, cause said at least one processor to use data generated by the first sensor group to monitor a limb pose, and to use data generated by the second sensor group to measure muscle and tendon activity, and combine the data generated by the first sensor group and second sensor group to determine extremity pose information, wherein, when executed, said processor-executable instructions further cause said at least one processor to generate and monitor information relating to muscle and tendon activity for an identified extremity pose, wherein the muscle and tendon activity comprises a length of time a specific tendon has been exerted, a number of times a specific tendon has been exerted, a load exerted on a specific tendon (i.e. tension), unequal use of tendons, or combinations thereof.

29. The apparatus as claimed in claim 28, wherein said plurality of sensors are mechanically isolated from one another.

30. The apparatus as claimed in claim 29, wherein said mechanical isolation enables said at least one peripheral device to isolate localized transmission of forces to a given sensor of said plurality of sensors.

31. The apparatus as claimed in claim 30, comprising said proximity sensor, wherein the data generated by the first sensor group comprises proximity data from said proximity sensor.

32. The apparatus as claimed in claim 31, wherein said proximity sensor is selected from a group consisting of: a time of flight sensor, a camera, and a capacitive sensor.

33. The apparatus as claimed in claim 28, comprising said inertial sensor, wherein the data generated by the first sensor group comprises inertial measurement data.

34. The apparatus as claimed in claim 33, wherein, when executed, said processor-executable instructions further cause said at least one processor to generate limb pose information from said inertial measurement data, wherein said limb pose information represents the limb pose of said user, such that said at least one processor generates gesture information from said extremity pose information and limb pose information.

35. The apparatus as claimed in claim 34, wherein said inertial sensor is selected from a group consisting of: an altitude sensor, an accelerometer, a compass, a gyroscope, a magnetometer, and a pressure sensor.

36. The apparatus as claimed in claim 28, wherein said at least one peripheral device further comprises a spring biasing a surface of said at least one peripheral device towards an extremity of said subject-user.

37. The apparatus as claimed in claim 28, wherein said at least one processor determines a device pose using data received from one or both of 1) one or more of said plurality of sensors, or 2) one or more peripheral sensors disposed upon said at least one peripheral device, wherein the device pose represents a pose of the at least one peripheral device relative to the user's body.

38. The apparatus as claimed in claim 28, wherein said one or more myographic sensors is selected from a group consisting of: a force sensor, a strain sensor, a pressure sensor; a piezo-resistive sensor, a piezo-electric sensor, an electromyographic sensor, and a capacitive sensor.

39. The apparatus as claimed in claim 28, further comprising one or more ancillary sensors spaced apart from said at least one peripheral device.

40. An apparatus comprising:
    at least one peripheral device worn by a subject-user and having a plurality of sensors, wherein the plurality of sensors comprises 1) a first sensor group comprising one or both of a proximity sensor or an inertial sensor, and 2) a second sensor group comprising one or more myographic sensors;
    at least one processor for receiving and processing data from said plurality of sensors;
    a peripheral device interface communicatively coupling said at least one peripheral device with said at least one processor; and
    at least one tangible computer-readable storage device communicatively coupled to said at least one processor and which stores processor-executable instructions which, when executed by said at least one processor, cause said at least one processor to use data generated by the first sensor group to monitor a limb pose, and to use data generated by the second sensor group to measure muscle and tendon activity, and combine the data generated by the first sensor group and second sensor group to determine extremity pose information, and wherein said at least one processor determines a device pose using data received from one or more peripheral sensors disposed upon said at least one peripheral device, wherein the device pose represents a pose of the at least one peripheral device relative to the user's body, wherein the one or more peripheral sensors is selected from the group consisting of: a photoplethysmograph, a bend sensor, and an environmental sensor.

41. The apparatus as claimed in claim 40, wherein said plurality of sensors are mechanically isolated from one another.

42. The apparatus as claimed in claim 41, wherein said mechanical isolation enables said at least one peripheral device to isolate localized transmission of forces to a given sensor of said plurality of sensors.

43. The apparatus as claimed in claim 40 comprising said proximity sensor, wherein the data generated by the first sensor group comprises proximity data from said proximity sensor.

44. The apparatus as claimed in claim 43, wherein said proximity sensor is selected from a group consisting of: a time of flight sensor, a camera, and a capacitive sensor.

45. The apparatus as claimed in claim 40, comprising said inertial sensor, wherein the data generated by the first sensor group comprises inertial measurement data.

46. The apparatus as claimed in claim 45, wherein, when executed, said processor-executable instructions further cause said at least one processor to generate limb pose information from said inertial measurement data, wherein said limb pose information represents the limb pose of said user, such that said at least one processor generates gesture information from said extremity pose information and limb pose information.

47. The apparatus as claimed in claim 46, wherein said inertial sensor is selected from a group consisting of: an altitude sensor, an accelerometer, a compass, a gyroscope, a magnetometer, and a pressure sensor.

48. The apparatus as claimed in claim 40, wherein said at least one peripheral device further comprises a spring biasing a surface of said at least one peripheral device towards an extremity of said subject-user.

49. The apparatus as claimed in claim 40, wherein said one or more myographic sensors is selected from a group consisting of: a force sensor, a strain sensor, a pressure sensor; a piezo-resistive sensor, a piezo-electric sensor, an electromyographic sensor, and a capacitive sensor.

50. The apparatus as claimed in claim 40, further comprising one or more ancillary sensors spaced apart from said at least one peripheral device.

51. An apparatus comprising:
at least one peripheral device worn by a subject-user and having a plurality of sensors, wherein the plurality of sensors comprises 1) a first sensor group comprising one or both of a proximity sensor or an inertial sensor, and 2) a second sensor group comprising one or more myographic sensors;
at least one processor for receiving and processing data from said plurality of sensors;
a peripheral device interface communicatively coupling said at least one peripheral device with said at least one processor; and
at least one tangible computer-readable storage device communicatively coupled to said at least one processor and which stores processor-executable instructions which, when executed by said at least one processor, cause said at least one processor to use data generated by the first sensor group to monitor a limb pose, and to use data generated by the second sensor group to measure muscle and tendon activity, and combine the data generated by the first sensor group and second sensor group to determine extremity pose information, and wherein said at least one processor determines a device pose using data received from one or more peripheral sensors disposed upon said at least one peripheral device, wherein the device pose represents a pose of the at least one peripheral device relative to the user's body, wherein said at least one peripheral device comprises an actuator in operative communication with said at least one processor, such that said actuator changes the device pose based on said data received by said at least one processor.

* * * * *